(12) United States Patent
Frohberg et al.

(10) Patent No.: US 9,365,861 B2
(45) Date of Patent: Jun. 14, 2016

(54) TRUNCATED ALTERNAN SUCRASE CODING NUCLEIC ACID MOLECULES

(75) Inventors: Claus Frohberg, Kleinmachnow (DE); Rosalinde Van Lipzip, Heusden (BE)

(73) Assignee: BAYER INTELLECTUALPROPERTY GMBH, Monheim am Rhein (DE)

( * ) Notice: Subject to any disclaimer, the term of this patent is extended or adjusted under 35 U.S.C. 154(b) by 1018 days.

(21) Appl. No.: 12/527,173

(22) PCT Filed: Feb. 13, 2008

(86) PCT No.: PCT/EP2008/051760
§ 371 (c)(1),
(2), (4) Date: Aug. 13, 2009

(87) PCT Pub. No.: WO2008/098975
PCT Pub. Date: Aug. 21, 2008

(65) Prior Publication Data
US 2010/0122378 A1    May 13, 2010

Related U.S. Application Data

(60) Provisional application No. 60/901,532, filed on Feb. 15, 2007.

(30) Foreign Application Priority Data

Feb. 14, 2007  (EP) .................................. 07090022

(51) Int. Cl.
*A01H 5/00*     (2006.01)
*A01H 5/10*     (2006.01)
*C12N 15/82*    (2006.01)
*C12N 9/10*     (2006.01)
*C12N 15/05*    (2006.01)
*C07B 37/02*    (2006.01)
*C08B 37/00*    (2006.01)

(52) U.S. Cl.
CPC ........ *C12N 15/8246* (2013.01); *C08B 37/0009* (2013.01); *C12N 9/1051* (2013.01); *C12Y 204/0114* (2013.01)

(58) Field of Classification Search
None
See application file for complete search history.

(56) References Cited

U.S. PATENT DOCUMENTS

| 6,479,275 B1 | 11/2002 | Leathers et al. |
| 2006/0127328 A1* | 6/2006 | Monsan et al. ................. 424/50 |

FOREIGN PATENT DOCUMENTS

| WO | WO 00/47727 | * | 8/2000 | ............... C12N 9/10 |
| WO | WO 0047727 | * | 8/2000 | |
| WO | WO 03/010177 | | 2/2003 | |
| WO | WO 2004/023891 | | 3/2004 | |

OTHER PUBLICATIONS

Joucla et al, Construction of a fully active truncated alternansucrase partially deleted of it carboxy-terminal domain, 2006, FEBS Letters 580:763-768.*
Aruguello-Morales et al, Sequence analysis of the gene encoding alternan sucrase, a sucrose glucosyltansferase from Leuconostoc mesenteroides 2000, FEMS Microbiology Letters 182:81-85.*
Joucla et al (FEBS Letters 580:763-768, published online Jan. 9, 2006).*
Joucla et al (FEBS Letters 580.763-768, published online Jan. 9, 2006).*
Cote, G., "Low-Viscosity α-D-Glucan Fractions Derived from Sucrose Which are Resistant to Enzymatic Digestion", Carbohydrate Polymers, vol. 19, pp. 249-252, Apr. 1992.
Leathers, T. et al., "Characterization of a Novel Modified Alternan", Carbohydrate Polymers, vol. 54, pp. 107-113, May 2003.
Lopez, A. et al., "Production and Purification of Leuconostoc Mesenteroides NRRL B-1355 Alternansucrase", Annals New York Academy of Sciences, vol. 15, pp. 717-722, (1993).
International Search Report for International Application No. PCT/EP2008/051760 mailed Jul. 21, 2008.
Written Opinion for International Application No. PCT/EP2008/051760 mailed Jul. 21, 2008.

* cited by examiner

*Primary Examiner* — Lee A Visone
(74) *Attorney, Agent, or Firm* — Arent Fox LLP

(57) ABSTRACT

The present invention relates to nucleic acid molecules which code for a truncated alternan sucrase. The invention further relates to truncated alternan sucrases, to vectors, to host cells and to plant cells transformed with the nucleic acid molecules described, and to plants comprising these cells. The present invention furthermore relates to novel alternan polymers with advantageous properties and to methods for their production.

27 Claims, 4 Drawing Sheets

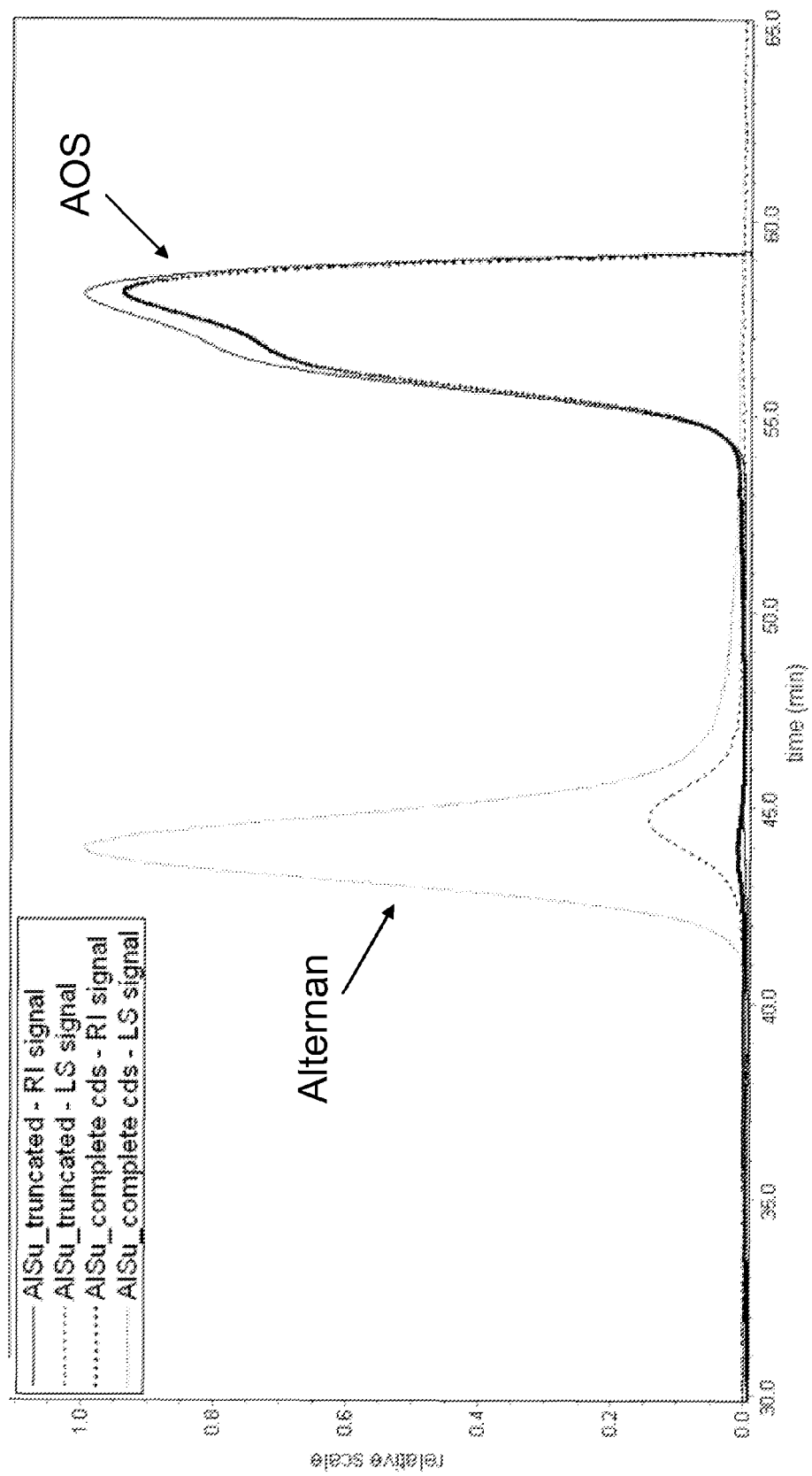

TRUNCATED ALTERNAN SUCRASE CODING NUCLEIC ACID MOLECULES

CROSS-REFERENCE TO RELATED APPLICATIONS

This application is the U.S. National Stage filing of International Application No. PCT/EP2008/051760, filed Feb. 13, 2008, which claims priority to European Patent Application No. EP 070 90 022.0, filed Feb. 14, 2007, and U.S. Provisional Application No. 60/901,532, filed Feb. 15, 2007, the disclosures of which are hereby incorporated in their entirety by reference.

The present invention relates to nucleic acid molecules which code for a truncated alternan sucrase. The invention further relates to truncated alternan sucrases, to vectors, to host cells and to plant cells transformed with the nucleic acid molecules described, and to plants comprising these cells. The present invention furthermore relates to novel alternan polymers with advantageous properties and to methods for their production.

Alternan is a polysaccharide composed of glucose units. The glucose units are linked with one another via $\alpha$-1,3 and $\alpha$-1,6-glycosidic bonds, with these two types of bond predominantly alternating (Miasaki et al., Carbo. Res., 84:273-285 (1980)). In addition, alternan may comprise branchings (Seymour et al., Carbohydrate Research 74, (1979); 41-62). Native alternan has a mean molecular weight Mw of $10^6$-$10^7$ (WO 03/010177).

Owing to its physical-chemical properties, possible uses for alternan have been discussed, not only in the pharmaceutical industry, for example as excipient for active ingredients in medicaments, but also as additive in the textile, the cosmetics and the food industry (Lopez-Munguia et al., Enzyme Microb. Technol. 15, (1993), 77-85; Leathers et al., Journal of Industrial Microbiology & Biotechnology 18, (1997), 278-283). Another potential use is as a substitute for gum arabic (Cote, Carbohydate Polymers 19, (1992), 249-252).

Alternan can be produced enzymatically using enzymes with the biological activity of alternan sucrases. Alternan sucrases belong to the group of the glucosyl transferases which, starting from sucrose, are capable of catalyzing the formation of glucan and fructose. Naturally occurring strains will, as a rule, also produce dextran in addition to alternan. The production of alternan sucrase from the natural strains is disadvantageous because it has not been possible to obtain the enzyme in its pure form, despite attempts to perform complicated purification procedures; see, for example, the overview in the introduction of WO 00/4772.

A large number of attempts have been made in the past to provide ultrapure alternan sucrase via alternative routes.

WO 00/47727 describes nucleic acid molecules which code for an alternan sucrase. Furthermore, WO 00/47727 relates to vectors, to host cells and to plant cells transformed with the described nucleic acid molecules and to plants comprising these cells. With the aid of the nucleic acid molecules of WO 00/47727, it is possible to generate host cells which produce recombinant alternan sucrase protein in high purity and/or in sufficient amounts, and to generate genetically modified plants with an activity of these enzymes, whereby alternan is formed in planta.

The patent application US20060127328A1 describes nucleic acid sequences of truncated or mutated alternan sucrases and vectors and transformed host cells. Ultrapure, truncated alternan sucrases which retain their catalytic activity are obtained. Furthermore, it is claimed that truncated alternan sucrases are expressed better and degraded less rapidly.

BRIEF DESCRIPTION OF VARIOUS EMBODIMENTS OF THE INVENTION

It is an object of the present invention in the light of the prior art to provide alternan sucrases with even better properties.

In particular, it was an object of the invention to provide nucleic acid molecules which are particularly well expressed in plant cells in order to achieve an efficient production of alternan sucrase in planta.

A further object was to provide an alternan sucrase which brings about an alternan production in a transgenic plant in high yield.

Furthermore, it was an object of the invention to provide an alternan sucrase with the aid of which an alternan with particularly advantageous properties can be prepared.

These objects are achieved by providing the use forms characterized in the patent claims.

Thus, the present invention relates to a nucleic acid molecule coding for a protein with the enzymatic activity of an alternan sucrase, where the nucleic acid molecule is selected among a) a nucleic acid molecule with a sequence from the nucleotide at position 118 up to and including to the nucleotide at position 4140 of the nucleic acid sequence shown in SEQ ID NO 1 or SEQ ID NO 3, b) a nucleic acid molecule which codes for a protein whose amino acid sequence has at least 70%, preferably at least 80%, more preferably at least 90%, even more preferably at least 95% and most preferably at least 98% identity with the sequence from the amino acid at position 40 up to and including to the amino acid at position 1380 of SEQ ID NO 2, c) a nucleic acid molecule with a sequence from the nucleotide at position 118 up to and including the nucleotide at position 3945 of the nucleic acid sequence shown in SEQ ID NO 1 or SEQ ID NO 3, d) a nucleic acid molecule which codes for a protein whose amino acid sequence has at least 70%, preferably at least 80%, more preferably at least 90%, even more preferably at least 95% and most preferably at least 98% identity with the sequence from the amino acid at position 40 up to and including to the amino acid at position 1315 of SEQ ID NO 2, e) a nucleic acid molecule with a sequence from the nucleotide at position 118 up to and including the nucleotide at position 4518 of the nucleic acid sequence shown in SEQ ID NO 1 or SEQ ID NO 3, f) a nucleic acid molecule which codes for a protein whose amino acid sequence has at least 70%, preferably at least 80%, more preferably at least 90%, even more preferably at least 95% and most preferably at least 98% identity with the sequence from the amino acid at position 40 up to and including to the amino acid at position 1506 of SEQ ID NO 2, g) a nucleic acid molecule whose sequence has at least 70%, preferably at least 80%, more preferably at least 90%, even more preferably at least 95% and most preferably at least 98% identity with the sequence of a), c) or e), where said sequence has the same number of nucleotides as the sequence of a), c) or e), h) a nucleic acid molecule whose nucleic acid sequence, as the result of the degeneracy of the genetic code, deviates from the sequence of the nucleic acid molecules of a), b), c), d), e), f) or g), i) a nucleic acid molecule whose nucleic acid sequence is complementary to the full-length sequence of one of the nucleic acid molecules of a), b), c), d), e), f), g) or h), where the complementary sequence has the same number of nucleotides as the nucleic acid molecules of a), b), c), d), e), f), g) or h).

BRIEF DESCRIPTION OF THE DRAWINGS

FIG. 4: Isomaltulose elugrams (RI and Light scattering— LS—signals).

DETAILED DESCRIPTION OF PREFERRED EMOBIDMENTS OF THE INVENTION

Figure 1:
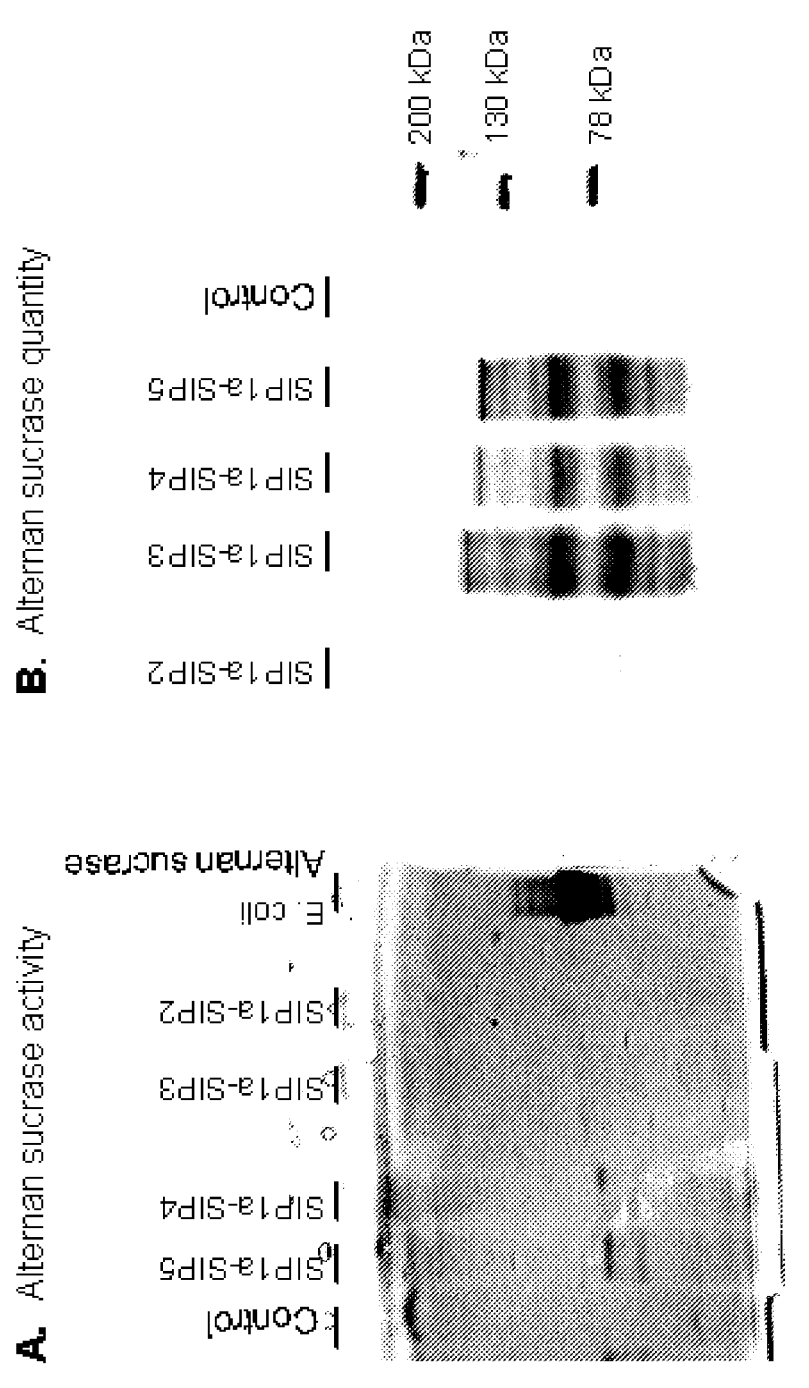
FIG. 1: Expression and quantity of alternan in wheat germ extract. A) shows alternan sucrose activity in wheat germ, and B) shows amount of alternan sucrose production in whaet germ extract.

The present invention has in particular the following advantages:

With the aid of the nucleic acid molecules according to the invention, it is possible to prepare proteins with the enzymatic activity of an alternan sucrase which, in comparison with the full-length alternan sucrase (for example of wild-type origin), have a truncated amino acid sequence.

In the present invention, "full-length alternan sucrase" refers to the protein which has an amino acid sequence from amino acid 40-2057 of SEQ ID NO 2. The full-length alternan sucrase in accordance with the above definition differs from the alternan sucrase as described in the literature (for example US20060127328A1) by the fact that it lacks the signal peptide of amino acid 1-39 of SEQ ID NO 2.

The proteins according to the invention with the enzymatic activity of an alternan sucrase are hereinbelow also referred to as "truncated alternan sucrase" or "truncated enzyme". The term "truncated" means a truncation at the N- and/or C-terminal end of the amino acid sequence of a full-length alternan sucrase, or at the 5' or 3' end of the nucleic acid sequence in question. The truncation can be carried out by means of restriction enzymes, proteolytic enzymes in the case of proteins, by complete synthesis (for example Merrifield) or, preferably, as described in the examples of this invention. For example, the nucleic acid molecules encoded by claim 1 and its preferred embodiments comprise truncated alternan sucrases in accordance with the present invention.

The nucleic acid molecules according to the invention preferably take the form of isolated nucleic acid molecules.

The truncated alternan sucrases of the present invention have a higher activity in plant cells than full-length enzymes.

Moreover, the truncated alternan sucrases of the present invention are expressed very well.

The truncated alternan sucrases can be introduced more readily into a plant vacuole or other plant compartments such as plastids or apoplast than the native full-length enzyme. This is advantageous for the production of alternan in planta since, depending on the plant species, the starting material sucrose is concentrated in the vacuole. It is frequently advantageous to express polymer-synthesizing enzymes in compartments other than the cytosol.

The present invention furthermore demonstrated that an alternan with advantageous properties can be obtained with the aid of truncated alternan sucrases encoded by the above nucleic acid molecules.

It can also be shown that truncated alternansucrase enzyme produces less alternan polymer as a by-product in alternan-oligosaccharide production than full-length alternansucrase. Alternan-oligosaccharides are produced by an alternansucrase enzyme catalyzed reaction of sucrose with various acceptor sugars and have been described as prebiotics for controlling enteric bacterial pathogens. By using truncated alternansucrase enzyme in the production of alternan-oligosaccharides, a higher yield of desired oligosaccharide product is obtained. Moreover, membrane purification of the oligosaccharide is facilitated since polymeric alternan may lead to membrane fouling.

Finally, the present invention also provides truncated alternan sucrases in high purity which retain their catalytic activity. It is possible with the aid of the nucleic acid molecules according to the invention to generate hose cells which produce a recombinant truncated alternan sucrase of high purity and/or in relative large amounts, and also to generate genetically modified plants with an activity of these enzymes, whereby the formation of alternan in planta results: in the context of the present invention, the term "high purity" means that the protein in accordance with the invention has a degree of purity of at least 80%, preferably of at least 90% and even more preferably of at least 95%.

Preferably excepted from the present invention are the nucleic acid molecules and truncated nucleic acid molecules described in the published patent application US20060127328A1.

Preferably excepted from the present invention are the nucleic acid molecules described in paragraphs [0062], [0065] and [0094] of US20060127328A1. In accordance with the numbering of SEQ ID NO 1, these are the following nucleic acid molecules:

1. from the nucleotide at position 1 up to and including the nucleotide at position 4275 of SEQ ID NO 1 (=nucleic acid 195-4469 in accordance with the numbering of US20060127328A1)
2. from the nucleotide at position 1 up to and including the nucleotide at position 4047 of SEQ ID NO 1 (=nucleic acid 195-4241 in accordance with the numbering of US20060127328A1)
3. from the nucleotide at position 1024 up to and including the nucleotide at position 4275 of SEQ ID NO 1 (=nucleic acid 1218-4469 in accordance with the numbering of US20060127328A1)
4. from the nucleotide at position 1 up to and including the nucleotide at position 3870 of SEQ ID NO 1 (=nucleic acid 195-4064 in accordance with the numbering of US20060127328A1)
5. from the nucleotide at position 1024 up to and including the nucleotide at position 3870 of SEQ ID NO 1 (=nucleic acid 1218-4064 in accordance with the numbering of US20060127328A1)

Preferably likewise excepted from the present invention are nucleic acid molecules which are mentioned in the specification WO00/47727 and which code for an alternan sucrase.

In contrast, further advantageous nucleic acid molecules of the present invention which code for a protein with the enzymatic activity of an alternan sucrase are:

1. a nucleic acid molecule with a sequence from the nucleotide at position 502 up to and including to the nucleotide at position 3945 of the nucleic acid sequence shown in SEQ ID NO 1 or SEQ ID NO 3, 2. a nucleic acid molecule which codes for a protein whose amino acid sequence has at least 70%, preferably at least 80%, more preferably at least 90%, even more preferably at least 95% and most preferably at least 98% identity with the sequence from the amino acid at position 168 up to and including to the amino acid at position 1315 of SEQ ID NO 2,
3. a nucleic acid molecule with a sequence from the nucleotide at position 1024 up to and including to the nucleotide at position 4047 of the nucleic acid sequence shown in SEQ ID NO 1 or SEQ ID NO 3,
4. a nucleic acid molecule which codes for a protein whose amino acid sequence has at least 70%, preferably at least 80%, more preferably at least 90%, even more preferably at least 95% and most preferably at least 98% identity with the sequence from the amino acid at position 342 up to and including to the amino acid at position 1349 of SEQ ID NO 2,
5. a nucleic acid molecule with a sequence from the nucleotide at position 1024 up to and including to the nucleotide at position 3945 of the nucleic acid sequence shown in SEQ ID NO 1 or SEQ ID NO 3, and
6. a nucleic acid molecule which codes for a protein whose amino acid sequence has at least 70%, preferably at least 80%, more preferably at least 90%, even more preferably at least 95% and most preferably at least 98% identity with the sequence from the amino acid at position 342 up to and including to the amino acid at position 1315 of SEQ ID NO 2.

Also encompassed by the invention are in each case nucleic acid molecules whose nucleic acid sequence deviates from the sequence of one of the above-specified nucleic acid molecules owing to the degeneracy of the genetic code. Likewise comprised are nucleic acid molecules whose sequence has at least 70%, preferably at least 80%, more preferably at least 90%, even more preferably at least 95% and most preferably at least 98% identity with one of the above-specified sequences. The term "identity" is defined somewhere else in the present disclosure, and a method of identifying the identity is detailed. Furthermore comprised by the present invention are nucleic acid molecules whose nucleic acid sequence is complementary to the full-length sequence of one of the abovementioned nucleic acid molecules, where the complementary sequence preferably has the same number of nucleotides as the abovementioned nucleic acid molecules.

Figure 2:
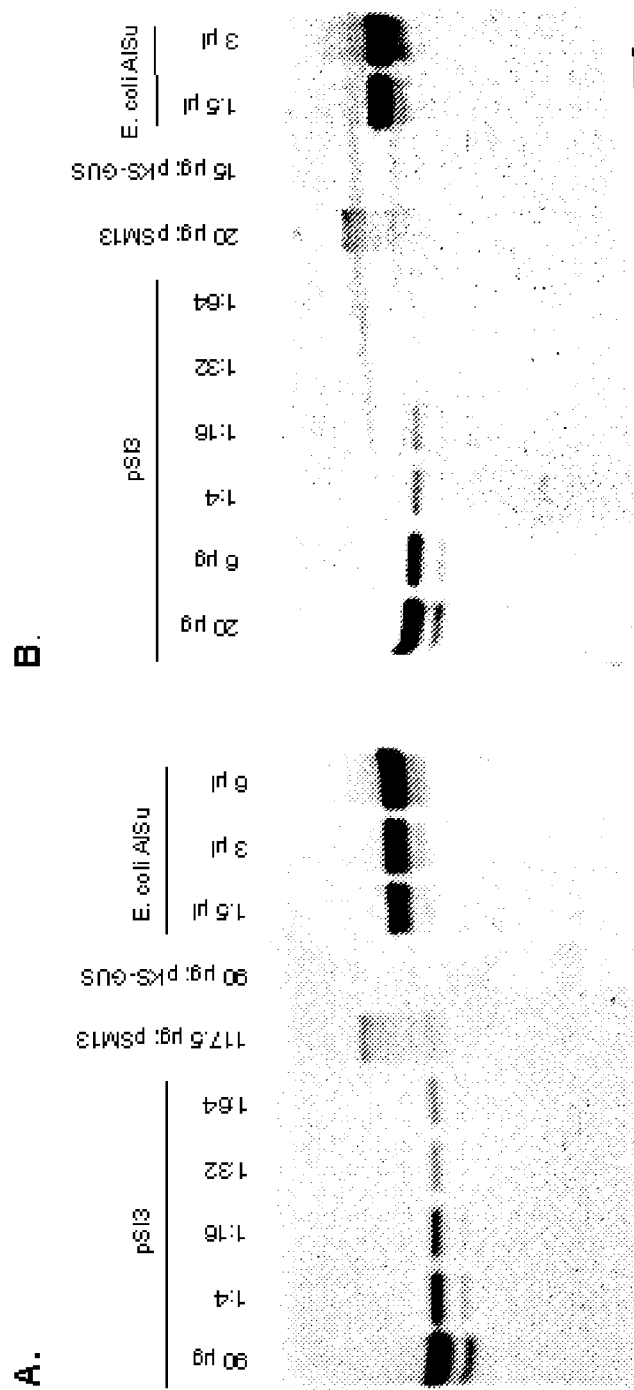
FIG. 2: Activity of protein encoded by pSI3.

Suggestions regarding the position of the nucleotide sequence or amino acid sequence where modifications may be accomplished while the encoded protein, or the protein with the amino acid sequence, still retains the enzymatic activity of an alternan sucrase can be found by the skilled worker in the literature. G. Joucla et al., FEBS Letters 580 (2006) 763-768 and US 2006/0127328A1 describe various domains of an alternan sucrase enzyme, see, for example, FIG. 2 in Joucla et al. and FIGS. 3A and 3B in US 2006/0127328A1. Firstly, this reference discloses an N-terminal, variable region in the range from amino acid 40 to 341 of the protein, which corresponds to the nucleotides 118 to 1023 of a suitable coding sequence, such as, for example, the nucleotides 118 to 1023 of SEQ ID NO 1 or 3 of the present invention. The N-terminal variable region is followed by a highly conserved catalytic domain from amino acid 342 to 1290 of the protein, corresponding to the nucleotides 1024 to 3870 of a corresponding coding sequence, for example with the SEQ ID NO 1 or 3 (G. Joucla et al, p. 763, left hand column). Departing from this disclosure, a skilled worker would expect that modifications of nucleotides/amino acids in the variable region would retain the enzymatic activity of an alternan sucrase rather than modifications in the highly conserved catalytic domain. Thus, the skilled worker would first perform modifications in the section of the nucleic acid molecule which codes for the variable region of an alternan sucrase proteins (nucleotides 118-1023 of SEQ ID 1 or 3) in order to generate a nucleic acid molecule whose sequence has at least 70%, preferably at least 80%, more preferably at least 90%, even more preferably at least 95% and most preferably at least 98% identity with the sequence of claim 1 a), c) or e) and which still codes for a protein with alternan sucrase activity. The same applies to a modification of the amino acid sequence in order to obtain a nucleic acid molecule in accordance with claim 1 b), d) or f), which the skilled worker would preferably perform in the region of amino acids 40-341 of SEQ ID NO 2.

Furthermore, G. Joucla et al., FEBS Letters 580 (2006) 763-768 and US 2006/0127328A1 detail a C-terminal domain (glucan binding domain, GBD) consisting of 709 amino acids and therefore comprising the amino acids 1348-2057 of an alternan sucrase enzyme. The C-terminal domain contains what are known as CW repeats and APY repeats. G. Joucla et al. explain that an alternan which is synthesized by an alternan sucrase which lacks the APY repeats (amino acid 1507-2057) is identical to an alternan obtained with native alternan sucrase. Thus, the APY motives are not involved in the polymerase activity of the enzyme (Joucla et al., p. 767, left hand side column). Moreover, the truncated alternan sucrase studied by Joucla et al. (referred to as "ASR C-APY-del") still contains only 4 of the original 7 CW repeats (Joucla et al. p. 765, left hand side column), without this affecting the polymerase activity of the enzyme. Thus, removal of the amino acids from position 1426-1481, which corresponds approximately to the CW units 5 to 7 (see. Joucla et al., FIG. 1) does not destroy the activity of the alternan sucrase either, as confirmed by the results of Joucla et al. Departing from a nucleic acid molecule in accordance with claim 1 e), a skilled worker would therefore preferably carry out modifications in the section from nucleotides 4276-4518 of SEQ ID NO 1 or 3, which codes for the amino acids 1426-1506 of an alternan sucrase in accordance with SEQ ID NO 2, in order to generate a nucleic acid molecule whose sequence has at least 70%, preferably at least 80%, more preferably at least 90%, even more preferably at least 95% and most preferably at least 98% identity with the sequence of claim 1 e). The same applies to a modification of the amino acid sequence in order to obtain a nucleic acid molecule in accordance with claim 1 f), which the skilled worker would preferably perform in the region of the amino acids 1426-1506 of SEQ ID NO 2.

However, what has been said above in no way rules out modifications in other regions of the nucleic acid/amino acid sequences according to the invention, with the enzymatic activity of an alternan sucrase still being retained. Modifications in other sections than those designated above are therefore expressly comprised by the scope of the present invention.

In the prior art of G. Joucla et al., it is maintained that removal of all of the C-terminal domain is unfavorable for protein expression (p. 765, right hand side column), where, according to Joucla, the C-terminal domain consists of 709 amino acids and thus comprises the amino acids 1348-2057 of an alternan sucrase (Joucla, p. 763, right hand side column). However, it was surprisingly demonstrated in the present invention that a truncated alternan sucrase which comprises the amino acids 40-1315 of SEQ ID NO 2 is expressed and is catalytically active, which was not to be expected in the light of the teaching of Joucla et al.

In a further aspect, the present invention relates to a nucleic acid molecule which codes for a protein with alternan sucrase activity selected from the group consisting of a) a nucleic acid molecule which comprises the nucleotide sequence shown in SEQ ID NO 3,
b) a nucleic acid molecule whose sequence has at least 70%, preferably at least 80%, more preferably at least 90%, even more preferably at least 95% and most preferably at least 98% identity with the sequence shown in SEQ ID NO 3,
c) a nucleic acid molecule whose nucleic acid sequence deviates from the sequence of the nucleic acid molecules of a) or b) owing to the degeneracy of the genetic code,
d) a nucleic acid molecule whose nucleic acid sequence is complementary to the sequence of one of the nucleic acid molecules of a), b), c) or part thereof,
e) nucleic acid molecules which are fragments, allelic variants and/or derivatives of the nucleic acid molecules mentioned in a), b), c) or d).

As the result of their codon-optimized sequence, the nucleic acid molecules based on SEQ ID NO 3 and designated in the above paragraph show improved expression in plant cells in comparison with the nucleic acid molecules of SEQ ID NO 1. The codons are modified in the sense that they are adapted to the frequency of the use of the codons of the plant cell or the plant into whose genome they are integrated or will be integrated. The codon usage of SEQ ID NO 3 was optimized specifically for maize and sugarcane.

Owing to the degeneracy of the genetic code, amino acids can be encoded by one or more codons. Different organisms use the codons, each of which encodes an amino acid, with different frequency. Adapting the codons of a coding nucleic acid sequence to the frequency of their use in the plant cell or in the plant into whose genome the sequence to be expressed is to be integrated may contribute to an increased amount of translated protein and/or to the stability of the respective mRNA in the plant cells or plants in question. The skilled worker can determine the frequency of the use of codons in plant cells or plants in question by studying the largest possible number of coding nucleic acid sequences of the organism in question for the frequency at which certain codons are used for encoding a certain amino acid. The frequency of the use of codons of certain organisms is known to the skilled worker and can be carried out simply and rapidly with the aid of computer programs. Suitable computer programs are publicly available and are freely available inter alia from the internet (for example http://gcua.schoedl.de/; http://www.kazusa.or.jp/codon/; http://www.entelechon.com/eng/cutanalysis.html).

Adapting the codons of a coding nucleic acid sequence to the frequency of its usage in the plant cell or in the plant into whose genome the sequence to be expressed is to be integrated can be effected by in-vitro mutagenesis or, preferably, by de-novo synthesis of the gene sequence. Methods for the de-novo synthesis of nucleic acid sequences are known to the skilled worker. A de-novo synthesis can be effected for example by first synthesizing individual nucleic acid oligonucleotides, hybridizing them with complementary oligonucleotides so that they form a DNA double strand, and then ligating the individual double-stranded oligonucleotides with one another in such a manner that the desired nucleic acid sequence is obtained. The de-novo synthesis of nucleic acid sequences including the adaptation of the frequency of the usage of the codons to a specific target organism may also be commissioned from companies offering such a service (for example Entelechon GmbH, Regensburg, Germany).

Preferably excepted from the present invention are also, among the previously described nucleic acid molecules with codon-optimized sequence, those nucleic acid molecules which are described in the specification WO 00/47727.

In the context of the present invention, the term "derivative" means that the sequences of these molecules differ from the sequences of the above-described nucleic acid molecules at one or more positions and that they have a high degree of identity with these sequences. The deviations from the above-described nucleic acid molecules may have originated for example as the result of deletion, addition, substitution, insertion or recombination. The allelic variants may take the form of naturally occurring variants or else of synthetically generated variants or variants which have been generated by recombinant DNA technologies.

Preferably, the nucleic acid triplet ATG is attached upstream of the 5' end of the nucleic acid molecules according to the invention described hereinabove and hereinbelow, unless such a triplet is already present at the 5' end of the sequence. In this preferred embodiment, ATG thus forms the new 5' end of the sequence. ATG acts as the start codon in the translation of the nucleic acid. The ATG triplet can be attached to the 5' end of a nucleic acid molecule according to the invention by methods known to the skilled worker. A widely used method is PCR with the use of specifically adapted primers, as described in the examples appended.

Preferably, a nucleic acid triplet selected among TAA, TAG or TGA is attached downstream of the 3' end of the nucleic acid molecules according to the invention described hereinabove and hereinbelow, unless such a triplet is already present at the 3' end of the sequence. In this preferred embodiment, TAA, TAG or TGA thus form the new 3' end of the sequence. The triplets mentioned act as stop codons in the transcription/translation of the nucleic acid molecules. A TAA, TAG or TGA triplet can be attached to the 3' end of a nucleic acid molecule according to the invention by methods known to the skilled worker. A widely used method is PCR with the use of specifically adapted primers, as described in the examples appended.

The proteins encoded by the nucleic acid molecules according to the invention are expressed very well in plant cells and in bacterial expression systems.

The nucleic acid molecules according to the invention may take the form of DNA molecules, in particular genomic molecules. The nucleic acid molecules according to the invention may furthermore be RNA molecules.

Nucleic acid molecules according to the invention which code for a truncated alternan sucrase may have been prepared synthetically or by recombinant techniques. To this end, it is possible for example to synthetically prepare a nucleic acid molecule with a codon-optimized sequence according to SEQ ID NO 3 which codes for a full-length alternan sucrase, as already described above. Then, the nucleic acid molecule with the sequence of SEQ ID NO 3 is used for preparing the nucleic acid molecules according to the invention, preferably by means of PCR technique using suitably adapted primers, which nucleic acid molecules code for a truncated alternan sucrase. The PCR method and suitable primers are detailed in the examples and in the appended sequence listings.

Nucleic acid molecules which code for a full-length alternan sucrase may also originate from a natural source, preferably from microorganisms, more preferably from bacteria, even more preferably from Gram-positive bacteria and most preferably from bacteria of the species *Leuconostoc*, in particular *Leuconostoc mesenteroides*. Nucleic acid molecules which code for a full-length alternan sucrase from *Leuconostoc mesenteroides* and which have a sequence as shown in SEQ ID NO 1 are described in WO 00/47727 whose disclosure is herewith incorporated by reference. The skilled worker can therefore consult the disclosure of WO 00/47727 to obtain a nucleic acid molecule as shown in SEQ ID NO 1. A nucleic acid molecule with the SEQ ID NO 1, in turn, can be used for preparing the nucleic acid molecules according to the invention which code for a truncated alternan sucrase. The preparation of the nucleic acid molecules according to the invention from nucleic acid molecules with a sequence as shown in SEQ ID NO 1 is preferably accomplished by means of PCR technique. Nucleic acid molecules according to the invention can also be prepared from a nucleic acid molecule with the SEQ ID NO 3 by means of PCR, analogously to the preparation of the nucleic acid molecules according to the invention from a nucleic acid molecule with the SEQ ID NO 1 as described in the examples. The preparation of the suitably adapted primers is within the competence of one skilled in the art.

A protein or enzyme with enzymatic or biological activity of an alternan sucrase (E.C. 2.4.1.140) is understood as meaning an enzyme which catalyzes the conversion of sucrose into alternan and fructose. This conversion may take place either in the presence or else in the absence of external acceptors (for example maltose, isomaltose, isomaltotriose and the like). In the absence of external acceptors, alternan sucrases will, starting from sucrose, catalyze the liberation of fructose and high-molecular-weight alternan, a polysaccharide composed of glucose units, whose backbone consists of glucose units which are linked with one another preferably alternately by α-1,3- and α-1,6-glycosidic bonds, where the structure may also contain branchings. In the presence of external acceptors such as, for example, maltose, isomaltose, isomaltotriose and methyl-alpha-D-glucan, alternan sucrase may catalyze, at those polysaccharide acceptors, the synthesis of alpha-D-glucan chains in which the glucose residues are predominantly alternately alpha-1,6- and alpha-1,3-glycosidically bonded, and of fructose. Depending on the acceptor employed, the products obtained have different structures. The enzymatic activity of an alternan sucrase can be detected for example as described by Lopez-Munguia (Annals New York Academy of Sciences 613 (1990), 717-722) or in the examples of the present application. One activity unit (1 u) may be defined as the amount of enzyme which, within one minute, leads to the liberation of 1 μmol fructose.

In the context of the present invention, the term "identity" means a sequence identity over the entire length of a nucleotide sequence or a sequence identity over the entire length of an amino acid sequence of at least 60%, preferably at least 70%, more preferably at least 80%, in particular at least 90%, even more preferably at least 95% and most preferably at least 98%. The present invention thus also comprises all those modifications of all nucleic acid or amino acid sequences according to the invention which are described herein which have the abovementioned percentage identity.

In connection with the present invention, the term "identity" is understood as meaning the number of agreeing amino acids/nucleotides (identity) with other proteins/nucleic acids, expressed in percent. The identity between two relevant amino acid sequences or between two relevant nucleic acid sequences is preferably determined with the aid of computer programs. If sequences which are compared with one another are different in length, the identity is to be determined in such a way that the number of amino acids which the shorter sequence shares with the longer sequence determines the percentage identity. Preferably, the identity is determined by means of the known and publicly available computer program ClustalW (Thompson et al., Nucleic Acids Research 22 (1994), 4673-4680). The definition of identity in the program ClustalW and the methods of determining it, which are publicly available, are expressly incorporated by reference. ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from various internet pages, inter alia the IGBMC (Institut de Génétique et de Biologie Moléculaire et Cellulaire, B.P.163, 67404 Illkirch Cedex, France; ftp://ftp-igbmc.u-strasbg.fr/pub/) and the EBI (ftp://ftp.ebi.ac.uk/pub/software/) and all mirrored EBI internet pages (European Bioinformatics Institute, Wellcome Trust Genome Campus, Hinxton, Cambridge CB10 1SD, UK).

Preferably, one uses the ClustalW computer program Version 1.8 to determine the identity between proteins described within the scope of the present invention and other proteins. In this context, the following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP. Preferably, one uses the computer program ClustalW Version 1.8 to determine the identity between for example the nucleotide sequence of the nucleic acid molecules described within the scope of the present invention and the nucleotide sequence of other nucleic acid molecules. In this context, the following parameters are to be set: KTUPLE=2, TOPDIAGS=4, PAIRGAP=5, DNAMATRIX: IUB, GAPOPEN=10, GAPEXT=5, MAXDIV=40, TRANSITIONS: unweighted.

In the present invention, the comparison sequence and the modified sequence (i.e. the compared sequences) preferably have the same number of nucleotides or amino acids. Still more preferably, the modified nucleic acid- or amino acid sequence is obtained by nucleotide- or amino acid-exchange in the comparison sequence. That is, the modified nucleic acid- or amino acid sequence is based on the same section of SEQ 1, 2 or 3 as the comparison sequence. For example, a modified nucleic acid molecule according to claim 1 g) whose sequence has at least 70%, preferably at least 80%, more preferably at least 90%, even more preferably at least 95% and most preferably at least 98% identity with the sequence of claim 1 a) is based on a nucleic acid molecule with a sequence from the nucleotide at position 118 up to and including to the nucleotide at position 4140 of the nucleic acid sequence shown in SEQ ID NO 1 or SEQ ID NO 3 (comparison sequence), but said nucleic acid molecule with a sequence from the nucleotide at position 118 up to and including to the nucleotide at position 4140 was modified by nucleotide exchange in order to obtain the modified sequence, wherein the number of nucleotides is maintained. The same principle may preferably be applied to all other herein described modified nucleic acid sequences or amino acid sequences which are defined by a certain percentage of identity in relation to a comparison sequence.

Also comprised by the invention is a nucleic acid molecule whose nucleic acid sequence differs from the sequence of one of the above-described nucleic acid molecules, in particular from a nucleic acid molecule as specified in claim 1, by one or more point mutation(s) within the nucleic acid sequence, with the enzymatic activity of an alternan sucrase being retained in the encoded protein.

It is possible to introduce the abovementioned mutations into the nucleic acid molecules by means of conventional molecular-biological techniques (see, for example, Sambrook et al., 2001, Molecular Cloning, A Laboratory Manual, 3rd edition, Cold Spring Harbor Laboratory Press, Cold Spring Harbor, N.Y.).

An example which is feasible is the introduction of point mutations at positions where a modification of the amino acid sequence has an effect for example on the enzyme activity or the regulation of the enzyme. In this manner, it is possible to generate for example mutants with a modified stereoselectivity and regioselectivity or an altered Km value, or which are no longer subject to the regulatory mechanisms which are normally present in the cell and which act via allosteric regulation or covalent modification. Such mutations, which may also be introduced into a nucleic acid molecule according to the invention, are described for example in the published patent application US 20060127328A1. Preferably excepted from the present invention are the nucleic acid molecules described in US20060127328A1, in particular in paragraphs [0063], [0064], [0066] and [0067]. Also preferably excepted from the present invention are the alternan sucrases of truncated length which are encoded by these nucleic acid molecules and which are described in particular in paragraph [0091] of US20060127328A1.

In order to subject prokaryotic cells to recombinant manipulation, the nucleic acid molecules according to the invention or parts of these molecules may be introduced into plasmids which permit a mutation or sequence modification by means of recombination of DNA sequences. Base exchanges may be carried out, or natural or synthetic sequences added, with the aid of standard methods (cf. Sambrook et al., 2001, Molecular Cloning: A laboratory manual, 3rd edition, Cold Spring Harbor Laboratory Press, NY, USA). To connect the DNA fragments with one another, adaptors or linkers may be added to the fragments. Furthermore, it is possible to employ manipulations which provide suitable restriction cleavage sites or which remove excess DNA or restriction cleavage sites. Where insertions, deletions or substitutions are suitable, in-vitro mutagenesis, "primer repair", restriction; PCR or ligation may be used (cf. Sambrook et al., 2001, Molecular Cloning: A laboratory manual, 3rd edition, Cold Spring Harbor Laboratory Press, NY, USA). Analytical methods which are generally carried out are sequence analysis, restrictions analysis and further biochemical/molecular-biological methods.

The invention also relates to nucleic acid molecules which hybridize under stringent conditions with the above-described nucleic acid molecules according to the invention, with the proviso that the encoded protein has the enzymatic activity of an alternan sucrase.

For the purposes of the present invention, the term "hybridization" means hybridization under conventional hybridization conditions, preferably under stringent conditions, as they are described for example in Sambrook et al., Molecular Cloning, A Laboratory Manual, 3rd edition, (2001) Cold Spring Harbor Laboratory Press, Cold Spring Harbor, N.Y. "Hybridization" particularly preferably means that a hybridization takes place under the following conditions: hybridization buffer: 2×SSC; 10×Denhardt's solution (Ficoll 400+ PEG+BSA; ratio 1:1:1); 0,1% SDS; 5 mM EDTA; 50 mM $Na_2HPO_4$; 250 µg/ml Herring sperm DNA; 50 µg/ml tRNA; or 0.25 M sodium phosphate buffer pH 7.2; 1 mM EDTA 7% SDS; T=65 to 68° C., wash buffer: 0.1×SSC; 0.1% SDS, wash temperature: T=65 to 68° C.

Nucleic acid molecules which hybridize with nucleic acid molecules according to the invention may originate from any desired organism; they can therefore originate from bacteria, fungi, animals, plants, or from viruses.

Nucleic acid molecules which hybridize with the abovementioned molecules can be isolated for example from genomic libraries or from cDNA libraries. The identification and isolation of such nucleic acid molecules can be effected using the abovementioned nucleic acid molecules or parts of these molecules, or the reverse complements of these molecules, for example by means of hybridization by standard methods (see, for example, Sambrook et al., 2001, Molecular Cloning, A Laboratory Manual, 3rd edition, Cold Spring Harbor Laboratory Press, Cold Spring Harbor, N.Y.), or by amplification by means of PCR.

The fragments used as hybridization probe can also take the form of synthetic fragments or oligonucleotides which have been prepared with the aid of the customary synthesis techniques and whose sequence agrees essentially with that of a nucleic acid molecule described within the scope of the present invention.

The molecules with hybridize with the nucleic acid molecules described within the scope of the present invention comprise in particular fragments, derivatives and allelic variants of the abovementioned nucleic acid molecules. In the context of the present invention, the term "derivative" means that the sequences of these molecules differ from the sequences of the above-described nucleic acid molecules at one or more positions and that they have a high degree of identity with these sequences. The deviations from the above-described nucleic acid molecules may have originated for example by deletion, addition, substitution, insertion or recombination.

The invention also relates to oligonucleotides which specifically hybridize with a nucleic acid molecule according to the invention. Such oligonucleotides preferably have a length of at least 10, in particular of at least 15 and particularly preferably of at least 50 nucleotides. They are characterized in that they specifically hybridize with nucleic acid molecules according to the invention, i.e. not, or only to a very low degree, with nucleic acid sequences which code for other proteins, in particular other glucosyl transferases. The oligonucleotides according to the invention can be used for example as primers for amplification techniques such as PCR reaction, or as hybridization probe for the isolation of related genes.

In a further preferred embodiment, the nucleic acid molecules according to the invention are linked to regulatory elements which ensure the transcription and synthesis of a translatable RNA in prokaryotic or eukaryotic cells. Such regulatory sequences are detailed in another part of the present disclosure, both for microorganisms and for plants.

The invention furthermore relates to vectors, in particular plasmids, cosmids, viruses, bacteriophages and other vectors conventionally used in genetic engineering, which comprise the above-described nucleic acid molecules according to the invention. In a preferred embodiment of the invention, the vectors according to the invention are suitable for the transformation of cells of microorganisms. Such vectors are preferably suitable for the transformation of plant cells. In a further preferred embodiment, these vectors permit integration, into the genome of the plant cell, of the nucleic acid molecules according to the invention, if appropriate together with flanking regulatory regions. Examples are binary vectors which can be employed in the *agrobacterium*-mediated gene transfer, some of which are already commercially available. Other vectors which can be used advantageously are those which comprise sequences which are integrated into the plant genome by means of direct gene delivery. An example of a reference on the direct gene delivery in sugarcane is: Bower R, Elliot A R, Potier B A M and Birch R G (1996) High efficiency, microprojectile-mediated cotransformation of sugarcane, using visible or selectable markers. Molecular Breeding 2: 239-249.

In one aspect of the present invention, the vectors are plasmids as described in US20060127328A1, paragraph [0076].

The expression of the nucleic acids of the present invention may take place in prokaryotic or eukaryotic cells. Examples of suitable cells are detailed in US20060127328A1, paragraph [0077].

Further preferred vectors are the vectors used in the appended use examples.

A particularly advantageous expression is the expression of the nucleic acid molecules according to the invention in prokaryotic or eukaryotic cells which are free from interfering enzymes, such as, for example, dextran sucrases or other polysaccharide-forming or -degrading enzymes.

In a further embodiment, the invention relates to host cells, in particular prokaryotic or eukaryotic cells, which are transformed with an above-described nucleic acid molecule according to the invention or a vector according to the invention, and to cells which are derived from such transformed cells and which comprise a nucleic acid molecule according to the invention or a vector according to the invention. The cell according to the invention is preferably an isolated host cell.

In a preferred embodiment, the host cells are cells of microorganisms. In the context of the present invention, the term "microorganism" comprises bacteria and all protists (for example fungi, in particular yeasts, algae) as defined in Schlegel "Allgemeine Mikrobiologie" (Georg Thieme Verlag, 1985, 1-2). In a preferred embodiment, the invention relates to cells of algae and host cells of the genera *Aspergillus, Bacillus*, in particular *Bacillus subtilis, Saccharomyces*, such as *Saccharomyces cerevisiae*, or *Pichia* (Rodriguez, Journal of Biotechnology 33 (1994), 135-146, Romanos, Vaccine, Vol. 9 (1991), 901 et seq.). Further suitable cells which can be used in the present invention are *Salmonella typhimurium*, strains originating from *Pseudomonas, Streptomyces* and *Staphylococcus*, parasites such as apicomplexan parasites (*Plasmodia, Toxoplasma, Cryptosporidia*), *Leishmania* or *Trypanosoma*. In a particularly preferred embodiment, the invention relates to *E. coli* cells.

It is particularly preferred that the truncated alternan sucrase is secreted from the host cell. The generation of such host cells for the production of a truncated alternan sucrase can be effected by methods known to the skilled worker. The secretion of proteins by microorganisms is normally mediated by N-terminal signal peptides (signal sequence, leader peptide, transit peptide). Proteins with this signal sequence are capable of penetrating the cell membrane of the microorganism. A secretion of proteins can be achieved by attaching the DNA sequence coding for the signal peptide to the corresponding, alternan sucrase encoding, region. Secretion is ensured by a signal sequence which comprises the first 39 N-terminal amino acid residues of SEQ ID NO 2.

In a preferred embodiment of the invention, the host cells according to the invention have no interfering enzyme activities, such as, for example, of polysaccharide-forming and/or -degrading enzymes.

An overview of the various expression systems is found, for example, in Methods in Enzymology 153 (1987), 385-516, in Bitter et al. (Methods in Enzymology 153 (1987), 516-544), and in Sawers et al. (Applied Microbiology and Biotechnology 46 (1996), 1-9), Billman-Jacobe (Current Opinion in Biotechnology 7 (1996), 500-4), Hockney (Trends in Biotechnology 12, (1994), 456-463), Griffiths et al., Methods in Molecular Biology 75 (1997), 427-440). An overview of yeast expression systems can be found for example in Hensing et al. (Antonie von Leuwenhoek 67 (1995), 261-279), Bussineau et al. (Developments in Biological Standardization 83 (1994), 13-19), Gellissen et al. (Antonie von Leuwenhoek 62 (1992), 79-93), Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors are described comprehensively in the literature. In addition to a selection marker gene and an origin of replication which ensures replication in the chosen host, they comprise, as a rule, a bacterial or viral promoter and in most cases a transcription termination signal. Between promoter and termination signal, there are located at least one restriction cleavage site or a polylinker, which elements make possible the insertion of a coding DNA sequence. An element which can be used as promoter sequence is the DNA sequence which naturally controls the transcription of the gene in question, as long as it is active in the chosen host organism. However, the other promoter sequences may also be substituted for this sequence. It is possible to use not only promoters which bring about a constitutive expression of the gene, but also inducible promoters, which permit a targeted regulation of the expression of the downstream gene. Bacterial and viral promoter sequences with these properties are described comprehensively in the literature. Regulatory sequences for expression in microorganisms (for example *E. coli, S. cerevisiae*) are described sufficiently in the literature.

Promoters which permit a particularly strong expression of the downstream gene are, for example, the T7 promoter (Studier et al., Methods in Enzymology 185 (1990), 60-89), lacuv5, trp, trp-lacUV5 (DeBoer et al., in Rodriguez and Chamberlin (Eds), Promotors, Structure and Function; Praeger, N.Y., (1982), 462-481; DeBoer et al. Proc. Natl. Acad. Sci. USA (1983), 21-25), 1p1, rac (Boros et al., Gene 42 (1986), 97-100). As a rule, the protein quantities reach their maximum from the middle to toward the end of the logarithmic phase of the microorganisms' growth cycle. The synthesis of proteins is therefore preferably carried out using inducible promoters. These frequently lead to higher protein yields than constitutive promoters. As a result of permanent transcription and translation of a cloned gene, the use of strong constitutive promoters frequently leads to the fact that energy is lost for other essential cell functions, whereby cell growth is slowed down (Bernard R. Glick/Jack J. Pasternak, Molekulare Biotechnologie (1995), Spektrum Akademischer Verlag GmbH, Heidelberg Berlin Oxford, p. 342.). To achieve an optimum amount of protein, one therefore frequently resorts to a two-step process. First, the host cells are cultured under optimal conditions until a relatively high cell density is reached. In the second step, transcription is then induced, depending on the type of promoter employed. A promoter which is particularly suitable in this context is a lactose- or IPTG-(=isopropyl-beta-D-thiogalactopyranoside) inducible tac promoter (deBoer et al., Proc. Natl. Acad. Sci. USA 80 (1983), 21-25). Transcription termination signals are likewise described in the literature (Young R A (1979) Transcription termination in the *Escherichia coli* ribosomal RNA operon rrnC, J Biol Chem. 254:12725-31; Lynn S P, Bauer C E, Chapman K, Gardner J F. (1985) Identification and characterization of mutants affecting transcription termination at the threonine operon attenuator. J Mol Biol. 183:529-41).

The transformation of the microbial host cell with the DNA which codes for a truncated alternan sucrase can, as a rule, be carried out by standard methods, such as, for example, those described in Sambrook et al. (Molecular Cloning: A Laboratory Course Manual, 3rd edition, (2001), Cold Spring Harbor Press, New York; Methods in Yeast Genetics, A Laboratory Course Manual, Cold Spring Harbor Laboratory Press, 1990). The host cell is cultured in nutrient media which meet the requirements of the particular host cell used in each case, in particular taking into consideration pH, temperature, salt concentration, aeration, antibiotics, vitamins, trace elements and the like.

The invention furthermore relates to proteins with the enzymatic activity of an alternan sucrase which are truncated in comparison with an abovedefined full-length alternan sucrase at the N- and/or C-terminal end of the amino acid sequence (hereinbelow also referred to as "truncated alternan sucrase") and which are encoded by nucleic acid molecules according to the invention with the corresponding sequence.

The invention particularly relates to the following proteins with the enzymatic activity of an alternan sucrase:

A protein with the enzymatic activity of an alternan sucrase, which protein is selected among
- a) a protein with an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1295 up to the amino acid at position 1345 of SEQ ID NO 2,
- b) a protein with an amino acid sequence which has at least 70%, preferably at least 80%, more preferably at least 90%, even more preferably at least 95% and most preferably at least 98% identity with an amino acid sequence of a), where the compared amino acid sequences preferably have the same number of amino acids,
- c) a protein with an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1355 up to the amino acid at position 1420 of SEQ ID NO 2,
- d) a protein with an amino acid sequence which has at least 70%, preferably at least 80%, more preferably at least 90%, even more preferably at least 95% and most preferably at least 98% identity with an amino acid sequence of c), where the compared amino acid sequences preferably have the same number of amino acids,
- e) a protein with an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1430 up to the amino acid at position 1520 of SEQ ID NO 2, or
- f) a protein with an amino acid sequence which has at least 70%, preferably at least 80%, more preferably at least 90%, even more preferably at least 95% and most preferably at least 98% identity with an amino acid sequence of e), where the compared amino acid sequences preferably have the same number of amino acids.

Even more preferably, the invention relates to a protein with the enzymatic activity of an alternan sucrase which protein is selected among
- a) a protein with an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1305 up to the amino acid at position 1325 of SEQ ID NO 2,
- b) a protein with an amino acid sequence which has at least 70%, preferably at least 80%, more preferably at least 90%, even more preferably at least 95% and most preferably at least 98% identity with an amino acid sequence of a), where the compared amino acid sequences preferably have the same number of amino acids,
- c) a protein with an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1370 up to the amino acid at position 1390 of SEQ ID NO 2,
- d) a protein with an amino acid sequence which has at least 70%, preferably at least 80%, more preferably at least 90%, even more preferably at least 95% and most preferably at least 98% identity with an amino acid sequence of c), where the compared amino acid sequences preferably have the same number of amino acids,
- e) a protein with an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1470 up to the amino acid at position 1520 of SEQ ID NO 2, or
- f) a protein with an amino acid sequence which has at least 70%, preferably at least 80%, more preferably at least 90%, even more preferably at least 95% and most preferably at least 98% identity with an amino acid sequence of a), where the compared amino acid sequences preferably have the same number of amino acids.

Most preferred are the following proteins with the enzymatic activity of an alternan sucrase
- a) a protein with a sequence from the amino acid at position 40 up to and including the amino acid at position 1380 of SEQ ID NO 2,
- b) a protein with a sequence from the amino acid at position 40 up to and including the amino acid at position 1315 of SEQ ID NO 2,
- c) a protein with a sequence from the amino acid at position 40 up to and including the amino acid at position 1506 of SEQ ID NO 2.

Equally comprised by the invention are the following proteins with the enzymatic activity of an alternan sucrase:
- d) a protein with a sequence from the amino acid at position 168 up to and including the amino acid at position 1315 of SEQ ID NO 2, e) a protein with a sequence from the amino acid at position 342 up to and including the amino acid at position 1349 of SEQ ID NO 2, f) a protein with a sequence from the amino acid at position 342 up to and including the amino acid at position 1315 of SEQ ID NO 2, Furthermore comprised by the invention are proteins with the enzymatic activity of an alternan sucrase whose amino acid sequences have at least 70%, more preferably at least 80%, in particular at least 90%, even more preferably at least 95% and most preferably at least 98% identity with the above-specified amino acid sequences, where the compared amino acid sequences preferably have the same number of amino acids. The term "identity" is defined as described above, and a method of identifying the identity has been described above.

In one embodiment of the invention, a methionine is located upstream of the N terminus of the proteins (or protein sequences) described hereinabove and hereinbelow which have the enzymatic activity of an alternan sucrase. In this preferred embodiment, methionine thus forms the N terminus of the amino acid sequence according to the invention. Such a methionine usually originates from the translation of the protein-encoding RNA, where it is encoded by the nucleic acid triplet ATG. Unless already present in the nucleic acid sequence, the ATG triplet can be attached to the 5' end of a nucleic acid molecule according to the invention by the method known to the skilled worker. An established method is PCR using specifically adapted primers, as described in the appended examples.

Preferably excepted from the present invention are the proteins with the enzymatic activity of an alternan sucrase described in US20060127328A1, in particular for the proteins described in paragraph [0089] and in FIGS. 3A and 3B of US20060127328A1. Preferably excepted from the present invention are thus the proteins from the amino acid at position 1 to 1425, position 1 to 1349, position 1 to 1290, position 342 to 1425 and position 342 to 1290, the positions being defined with reference to the appended SEQ ID NO 2.

The invention furthermore relates to a method of producing an above-described protein according to the invention with the enzymatic activity of an alternan sucrase, in which a host cell is transformed with a) a nucleic acid molecule whose sequence codes for the amino acid sequence of an above-described protein with the enzymatic activity of an alternan sucrase, where the nucleic acid molecule is obtainable from a nucleic acid molecule with a sequence shown in SEQ ID NO 1 or 3, or b) a vector or plasmid comprising a nucleic acid molecule as described in a), 2) the host cell is cultured in culture medium, and 3) the protein is isolated from the cultured cells and/or the culture medium.

The amino acid sequences of the proteins according to the invention with the enzymatic activity of an alternan sucrase are detailed further above and defined with reference to SEQ ID NO 2. Based on the amino acid sequences, the skilled worker can determine suitable coding nucleic acid sequences, which may differ from one another owing to the degeneracy of the genetic code. For example, from SEQ ID NO 1, comprising the amino acid sequence of a full-length alternan sucrase and a coding nucleotide sequence, it is possible to determine the respective nucleic acid sequence which codes for the protein according to the invention (truncated alternan sucrase). On the basis of the same nucleotide positions as in SEQ ID NO 1, which determine the beginning and end of the nucleotide sequence for the protein according to the invention which is desired in each case, it is also possible to determine, on the basis of SEQ ID NO 3, a nucleic acid sequence which codes for the protein. Likewise, it is possible to translate the nucleotide sequence in accordance with SEQ ID NO 3 into an amino acid sequence, and, with reference to the beginning and end of the amino acid sequence desired, as detailed for the proteins according to the invention, to determine the corresponding coding nucleotide sequence.

After the sequence has been determined, a nucleic acid molecule with this sequence can be generated from a nucleic acid molecule with a sequence in accordance with SEQ ID NO 1 or SEQ ID NO 3. The generation of a nucleic acid molecule whose sequence codes for the amino acid sequence of a protein according to the invention with the enzymatic activity of an alternan sucrase is preferably accomplished by means of a PCR technique, starting from nucleic acid molecules with a sequence in accordance with SEQ ID NO 1 or 3. Generating suitably adapted primers is within the knowledge of one skilled in the art.

It is also possible to employ, in the above-described process, all above-described nucleic acid molecules according to the invention which code for a protein with the enzymatic activity of an alternan sucrase and which is truncated at the N- and/or C-terminal end of the amino acid sequence in comparison with a full-length alternan sucrase. In particular, it is possible to employ the nucleic acid molecules defined in claim 1.

As regards the vectors and plasmids which can be employed in the above process, reference is made at another place to the disclosure in question. Furthermore, host cells and techniques for the transformation of microbial and plant host cells which can be employed in the above process are disclosed in detail in another place of the present description. Plant host cells or microbial host cells, for example *Escherichia coli* cells, are preferred.

The host cells are grown, i.e. cultured and propagated, in a suitable nutrient medium and under suitable culture conditions. Nutrient media and culture conditions for customary microbial and plant cells are known to the skilled worker and described in the specialist literature (for example Sambrook & Russell Molecular cloning: a laboratory manual (third edition) Cold Spring Harbor Laboratory Press, NY, USA (2001)).

Finally, the protein is isolated from the host cell and/or from the culture medium. To this end, the cell material produced is, as a rule, disrupted with the aid of suitable physical, chemical and/or enzymatic methods. The proteins with the enzymatic activity of an alternan sucrase can be isolated from the disrupted material.

The further purification of the proteins can be accomplished with the aid of customary methods known in the art. To obtain a crude extract, the solution obtained in the disruption procedure is treated for example with the aid of extraction methods, centrifugation methods and filtration methods. Precipitation of the proteins from the crude extract, and ultrafiltration methods, are efficient methods for concentrating proteins from a substantial amount of fluid. Suitable precipitating agents are, inter alia, inorganic salts, for example sodium sulfate and ammonium sulfate, organic solvents, for example alcohols, and polymers, for example polyethylene glycol. To remove the precipitating agent used, a dialysis process can subsequently be carried out. A further secondary purification can be accomplished with the aid of chromatographic methods and distribution methods, for example using aqueous phase systems. These methods include, inter alia, adsorption chromatography, ion-exchange chromatography, gel chromatography and affinity chromatography.

In a further aspect, the protein according to the invention with the enzymatic activity of an alternan sucrase can be synthesized by the Merrifield protein synthesis method. Thus, synthetically produced truncated alternan sucrases are a further aspect of the present invention.

In a further aspect, the protein according to the invention with the enzymatic activity of an alternan sucrase can also be prepared with cell-free in-vitro expression/translation systems. An in-vitro translation is possible for example in wheat germ extract. However, the in-vitro methods are in now way restricted, and any method known in the art may be used in principle.

In accordance with invention, it is possible to use host cells and vectors which permit production of the truncated alternan sucrase in the absence of sucrose so that an additional separation of the truncated alternan sucrase from polysaccharides is no longer required.

The purification of the truncated alternan sucrase produced by the host cells can be effected with the aid of traditional purification methods such as precipitation, ion-exchange chromatography, affinity chromatography, gel filtration, HPLC; reverse phase chromatography and the like.

As a result of the modification of the nucleic acid molecules according to the invention which are expressed in the host cells and which code for a truncated alternan sucrase, a polypeptide can be produced in the host cell which, as a result of certain characteristics, can be isolated more readily from the culture medium. Thus, it is possible to express the protein to be expressed as a fusion protein with a further polypeptide sequence (tag) whose specific binding properties make possible the isolation of the fusion protein via affinity chromatography (for example Hopp et al., Bio/Technology 6 (1988), 1204-1210; Sassenfeld, Trends Biotechnol. 8 (1990), 88-93). Conventionally used tags, are, for example, the Strep-tag, the His-tag, the FLAG-tag, the T7-tag, the S-tag.

Moreover, the nucleic acid sequences of the present invention may be modified at the 5' or 3' terminus by sequences which code for tags at the N or C terminus of the protein, for example also by those which are described in US20060127328A1 paragraph [0071].

By providing the nucleic acid molecules according to the invention, it is possible, with the aid of recombinant methods, to generate plant cells which express truncated alternan sucrase. The invention thus also relates to transgenic plant cells which have been transformed with a nucleic acid molecule according to the invention or a vector according to the invention or which are derived from such cells, where the nucleic acid molecule which codes for the protein with the enzymatic activity of an alternan sucrase is under the control of regulatory elements which initiate the transcription of a translatable mRNA in plant cells (promoters). These may take the form of homologous or heterologous promoters. The promoters may take the form of constitutive promoters, of tissue-specific promoters, of development-specific promoters or else of promoters which are regulated by external factors (for example after application of chemical substances, as a result of the effect of abiotic factors such as heat and/or cold, drought, incidence of disease and the like).

A promoter which is suitable for the expression of a foreign nucleic acid molecule is, in general, a promoter which is active in plant cells. Examples of suitable promoters are the 35S RNA promoter of the Cauliflower Mosaic Virus or the Ubiquitin promoter from maize or the Cestrum YLCV promoter (Yellow Leaf Curling Virus; WO 01 73087; Stavolone et al., 2003, Plant Mol. Biol. 53, 703-713) for constitutive expression, the Patatin gene promoter B33 (Rocha-Sosa et al., EMBO J. 8 (1989), 23-29) for a tuber-specific expression in potatoes, or a fruit-specific promoter for tomatoes such as, for example, the tomato polygalacturonase promoter (Montgomery et al., 1993, Plant Cell 5, 1049-1062) or the tomato E8 promoter (Metha et al., 2002, Nature Biotechnol. 20(6), 613-618) or the peach ACC oxidase promoter (Moon and Callahan, 2004, J. Experimental Botany 55 (402), 1519-1528), or a promoter which ensures expression only in photosynthetically active tissues, for example the ST-LS1 promoter (Stockhaus et al., Proc. Natl. Acad. Sci. USA 84 (1987), 7943-7947; Stockhaus et al., EMBO J. 8 (1989), 2445-2451), or, for endosperm-specific expression, the wheat HMWG promoter, the USP promoter, the phaseolin promoter, promoters from Zein genes from maize (Pedersen et al., Cell 29 (1982), 1015-1026; Quatroccio et al., Plant Mol. Biol. 15 (1990), 81-93), a glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218), a globulin promoter (Nakase et al., 1996, Gene 170(2), 223-226), a prolamine promoter (Qu and Takaiwa, 2004, Plant Biotechnology Journal 2(2), 113-125) or a Shrunken-1 promoter (Werr et al., EMBO J. 4 (1985), 1373-1380). However, it is also possible to use promoters which are only activated at a point in time which is determined by external factors (see, for example, WO 9307279). Of particular interest in this context may be promoters of heat-shock proteins, which permit simple induction. It is furthermore possible to use seed-specific promoters such as, for example, the USP promoter from *Vicia faba*, which ensures a seed-specific expression in *Vicia faba* and other plants (Fiedler et al., Plant Mol. Biol. 22 (1993), 669-679; Bäumlein et al., Mol. Gen. Genet. 225 (1991), 459-467).

The use of promoters which are found in the genome of viruses which infect algae are also suitable for the expression of nucleic acid sequences in plants (Mitra et al., 1994, Biochem. Biophys Res Commun 204(1), 187-194; Mitra and Higgins, 1994, Plant Mol Biol 26(1), 85-93, Van Etten et al., 2002, Arch Virol 147, 1479-1516).

In the context of the present invention, the term "tissue-specific" is understood as meaning the predominant limitation of an infestation (for example transcriptional initiation) to a specific tissue.

In the context of the present invention, the terms "tuber cell, fruit cell or endosperm cell" are to be understood as meaning all those cells which are present in a tuber, a fruit or in a seed.

In the context of the present invention, the term "homologous promoter" is understood as meaning a promoter which naturally occurs in plant cells or plants which have been used for the generation of genetically modified plant cells according to the invention or genetically modified plants according to the invention (homologous with regard to the plant cell or plant), or a promoter which regulates the regulation of the expression of a gene in the organism from which the respective foreign nucleic acid molecule which encodes a protein has been isolated (homologous with regard to the nucleic acid molecule to be expressed).

In the context of the present invention, the term "heterologous promoter" is understood as meaning a promoter which naturally does not occur in plant cells or plants which have been used for the generation of genetically modified plant cells according to the invention or genetically modified plants according to the invention (heterologous with regard to the plant cell or plant), or a promoter which naturally does not regulate the expression of said foreign nucleic acid molecule in the organism from which the respective foreign nucleic acid molecule which encodes a protein has been isolated (heterologous with regard to the nucleic acid molecule to be expressed).

It is also possible for a termination sequence (polyadenylation signal) to be present, which serves to add a poly-A tail to the transcript. The poly-A tail is assumed to exert a function in stabilizing the transcript. Such elements are described in the literature (cf. Gielen et al., EMBO J. 8 (1989), 23-29), and they can be substituted as desired.

The present disclosure also explicitly refers to the promoters and termination sequences which are described in WO 00/47727, pages 21/22.

It is also possible for intron sequences to be present between the promoter and the coding region of the foreign nucleic acid molecule. Such intron sequences may result in the stability of expression, and in an increased expression in plants (Callis et al., 1987, Genes Devel. 1, 1183-1200; Luehrsen, and Walbot, 1991, Mol. Gen. Genet. 225, 81-93; Rethmeier et al., 1997; Plant Journal 12(4), 895-899; Rose and Beliakoff, 2000, Plant Physiol. 122 (2), 535-542; Vasil et al., 1989, Plant Physiol. 91, 1575-1579; XU et al., 2003, Science in China Series C Vol. 46 No. 6, 561-569). Suitable intron sequences are, for example, the first intron of the maize sh1 gene, the first intron of the maize polyubiquitin gene 1, the first intron of the rice EPSPS gene, or one of the first two introns of the *Arabidopsis* PAT1 gene.

By introducing the activity of the proteins according to the invention, for example by expressing suitable nucleic acid molecules, it is possible to produce alternan in suitably genetically modified plant cells. This allows the expression of the nucleic acid molecules according to the invention in plant cells, whereby an additional activity of the alternan sucrase in question, which is not present in the wild type, may be introduced. It is furthermore possible to modify the nucleic acid molecules according to the invention by methods known to the skilled worker in order to obtain truncated alternan sucrases according to the invention with, for example, modified temperature dependencies, or substrate or product specificities. Such methods are described in greater detail in the patent application WO00/47727.

A multiplicity of techniques is available for the generation of plant cells according to the invention, or of plants which comprise plant cells according to the invention, for the (stable) integration of nucleic acid molecules into a plant host cell. These techniques comprise the transformation of plant cells with T-DNA using *Agrobacterium tumefaciens* or *Agrobacterium rhizogenes* as transformation agents, the fusion of protoplasts, the injection, the electroporation of DNA, the introduction of the DNA by means of biolistic approach, and other possibilities (review in "Transgenic Plants", Leandro ed., Humana Press 2004, ISBN 1-59259-827-7).

The use of the agrobacteria-mediated transformation of plant cells has been studied intensively and has been described sufficiently in EP 120516 and Hoekema, IN: The Binary Plant Vector System Offsetdrukkerij Kanters B. V. Alblasserdam (1985), Chapter V; Fraley et al., Crit. Rev. Plant Sci. 4, 1-46 and in An et al. EMBO J. 4, (1985), 277-287). For the transformation of potato, see, for example, Rocha-Sosa et al., EMBO J. 8, (1989), 29-33), for the transformation of tomato plants, see, for example, U.S. Pat. No. 5,565,347.

For the transformation of monocotyledonous plants by means of vectors based on *Agrobacterium* transformation have also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system for the transformation of monocotyledonous plants is the transformation by means of biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, the electroporation of partially permeabilized cells, the introduction of DNA by means of glass fibers. The transformation of maize, in particular, is described repeatedly in the literature (cf. for example, WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The transformation of other grasses, such as, for example, switchgrass (*Panicum virgatum*) have likewise been described (Richards et al., 2001, Plant Cell Reporters 20, 48-54).

The successful transformation of other cereal species has also been described, for example for barley (Wan and Lemaux, see above; Ritala et al., see above; Krens et al., Nature 296, (1982), 72-74) and for wheat (Nehra et al., Plant J. 5, (1994), 285-297; Becker et al., 1994, Plant Journal 5, 299-307). All the above methods are suitable for the purposes of the present invention.

Genetically modified plant cells and genetically modified plants which contain a foreign nucleic acid molecule can be distinguished from wild-type plant cells, or wild-type plants which do not comprise said foreign nucleic acid molecule inter alia by the fact that they comprise a foreign nucleic acid molecule which does not occur naturally in wild-type plant cells, or wild-type plants. The integration of a foreign nucleic acid molecule into a plant cell or plant can be detected by methods which are known to the skilled worker, such as, for example, Southern blot analysis, or by means of PCR.

The foreign nucleic acid molecule is preferably integrated into the genome; the foreign nucleic acid molecule is especially preferably stably integrated into the genome, of the plant cells according to the invention or plants according to the invention. In the context of the present invention, the term "stably integrated nucleic acid molecule" is understood as meaning the integration of a nucleic acid molecule into the genome of the plant. A stably integrated nucleic acid molecule is distinguished by the fact that it is replicated upon replication of the integration site in question together with the homologous nucleic acid sequences which flank the integration site so that the integration site in the replicated daughter DNA strand is surrounded by the same nucleic acid sequences as on the read parent strand, which acts as matrix for the replication.

The integration of a nucleic acid molecule into the genome of a plant cell or a plant can be detected by genetic and/or molecular-biological methods. A stable integration of a nucleic acid molecule into the genome of a plant cell or into the genome of a plant is distinguished by the fact that the stably integrated nucleic acid molecule is present in the same genomic environment in the progeny to which said nucleic acid molecule has been passed on as in the parenteral generation. For the presence of a stable integration of a nucleic acid sequence in the genome of a plant cell or in the genome of a plant can be detected by methods known to the skilled worker, inter alia with the aid of the Southern blot analysis, the RFLP analysis (restriction fragment length polymorphism) (Nam et al., 1989, The Plant Cell 1, 699-705; Leister and Dean, 1993, The Plant Journal 4 (4), 745-750), PCR-based methods such as, for example, the analysis of amplified fragment length polymorphisms (AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160), or the use of amplified fragments which have been cleaved with restriction endonucleases (Cleaved Amplified Polymorphic Sequences, CAPS) (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753).

In the context of the present invention, the term "genome" is understood as meaning all of the hereditary material which is present in a plant cell. The skilled worker knows that not only the nucleus, but other compartments too (for example plastids, mitochondria) comprise hereditary material. A nucleic acid molecule according to the invention may be integrated into the nuclear genome, but also into the genome of other compartments such as, for example, plastids.

Furthermore, the plant cells according to the invention can be distinguished from naturally occurring plant cells by preferably at least one of the following features: if the transgenic plant cells comprise transcripts of the nucleic acid molecules according to the invention which have been introduced, this can be verified for example by Northern blot analysis. Preferably, the plant cells according to the invention comprise a truncated alternan sucrase which is encoded by a nucleic acid molecule according to the invention which has been introduced. This can be detected for example by immunological methods, in particular by a Western blot analysis. If a plant cell or plant according to the invention comprises a truncated alternan sucrase, a plant cell or plant according to the invention can advantageously also be distinguished by the fact that it comprises an alternan sucrase activity in comparison with wild-type cells/wild-type plants. The enzymatic activity of an alternan sucrase can be measured as described for example in Lopez-Munguia et al. (Annals New York Academy of Sciences 613, (1990), 717-722) or as specified in the examples of the present invention.

In a further preferred embodiment, the plant cells are cells from potato, sugarcane, maize, tobacco, sugar beet, sugar sorghum, rice or wheat.

The transgenic plant cells can be regenerated by techniques known to the skilled worker to give intact plants.

The plants obtainable by regeneration of the transgenic plant cells according to the invention are a further subject matter of the present invention.

In most plants, the photoassimilates which have been formed within a plant during photosynthesis in the form of sugars are transported to the target organs in question, predominantly in the form of sucrose. Since sucrose is the substrate for the polymerization reaction of the truncated alternan sucrase according to the invention, it is possible to modify, in principle, all plants, both monocotyledonous and dicotyledonous plants, with the aid of the nucleic acid molecule according to the invention with regard to the expression of the truncated alternan sucrase.

The expression of the nucleic acid molecules according to the invention is particularly advantageous in those plant organs which have a higher sucrose content or which store sucrose. Such organs are, for example, the root of sugar beet, the stem of sugarcane, the stem of maize plants or the stem of sugar sorghum.

The site of sucrose biosynthesis in plant cells is the cytosol. In contrast, the site of storage is the vacuole. Upon transport into the storage tissue of the sugar beet or of the potato, or upon the transport into the endosperm of seeds, the sucrose must migrate across the apoplast. Thus, all three compartments are suitable for the expression of the nucleic acid molecules according to the invention for the synthesis of alternan, that is to say the cytosol, the vacuole and the apoplast. Moreover, the plastids are also suitable, as has been demonstrated for example by means of the amyloplastidial expression of bacterial fructosyl transferases. These fructosyl transferases, which likewise require sucrose as their substrate, have been able to mediate the formation of "amylofructan" in amyloplasts (Smeekens, Trends in Plant Science vol. 2, Nr. 8, (1997), 286-288). The publications WO2006/072603 and WO 2006/063862 relate to genetically modified plant cells and plants in which the genetic modification leads to the expression of mutan sucrase, or dextran sucras, respectively, in plastids.

In the case of starch-producing plants such as, for example, potato and maize, in which starch biosynthesis and starch storage normally takes place in the amyloplasts, an expression of the truncated alternan sucrase in the apoplast, in the cytosol or in the vacuole would lead to an additional synthesis of oligo- and/or polysaccharides in these compartments, which, in total, may mean that the yield is increased. This may also be the case with the plastids, since it is not ADP-glucose which is utilized here, but the plastidic sucrose.

Since it is possible in plants, in particular potato, to separate the starch synthesized in the amyloplasts from the alternan synthesized in the apoplast, in the cytosol or in the vacuole, the same plant may be used for obtaining starch and alternan.

Furthermore, transgenic potato and maize plants are known in which, as the result of the inhibition of the enzyme ADP-glucose pyrophosphorylase by an antisense construct, starch synthesis in the tubers or in the grains is completely inhibited. Instead, soluble sugars, in particular sucrose and glucose, are accumulated for example in the tubers in the case of potato (Müller-Röber et al., EMBO J. 11, (1992), 1229-1238). As the result of the expression of a truncated alternan sucrase which utilizes sucrose as its substrate, alternan can be produced in the cytosol, in the vacuole or in the apoplast of these plants.

This is where, in another embodiment of the invention, the plant cells or plants according to the invention have, in comparison with corresponding cells of wild-type plants, a reduced ADP-glucose pyrophosphorylase (AGPase) activity. DNA molecules which code for AGPase are well known to the skilled person and described, for example, in Müller-Röber et al. (Mol. Gen. Genet. 224 (1) (1990), 136-146). As a result of AGPase-encoding DNA molecules, it is possible to generate, using recombinant DNA techniques (for example an antisense, a ribozyme or a cosuppression approach), plants which have a reduced AGPase activity. Moreover, the person skilled in the art knows AGPase mutants, for example from maize (brittle-2 and shrunken-2) with a reduced AGPase activity. The term "reduced or diminished" preferably means a reduction in the AGPase activity of at least 10%, more preferably of at least 50% and even more preferably of at least 80% in comparison with the corresponding wild-type cells.

When expressing the nucleic acid molecules according to the invention in plants, it is possible in principle for the protein synthesized which has the enzymatic activity of an alternan sucrase to be located in any compartment of the plant cell (for example cytosol, plastids, vacuole, mitochondria) or the plant (for example apoplast). To achieve localization in a specific compartment, the coding region must, if appropriate, be linked with DNA sequences which ensure localization in the compartment in question. Such sequences are known (see, for example, Braun, EMBO J. 11 (1992), 3219-3227; Sonnewald, Plant J. 1 (1991), 95-106; Rocha-Sosa, EMBO J. 8 (1989), 23-29, Neuhaus and Rodgers, 1998, Plant Molecular Biology 38: 127-144) Linking the signal sequences with the coding region of the protein is accomplished in such a manner that the fused signal peptide nucleic acid sequences and those coding for the protein together form an open reading frame during transcription (translational fusion). This is why, after translation of the RNA, which is the result of the transcription of the fused nucleic acid sequences, a protein is formed which comprises a signal peptide in addition to the coding region of the protein.

A plastidic signal sequence which can be used is, in principle, any signal sequence which ensures the import of nuclear-encoded proteins into plastids. The skilled worker knows how to obtain plastidic signal sequences. Thus, it is possible for example to examine coding protein sequences with the aid of computer programs (1999, Emanuelsson et al., Protein Science 8, 978-984) for the presence of a plastidic signal sequence. Computer programs which perform such analyses are both commercially available and publicly available on the internet (for example http://www.cbs.dtu.dk/services/ChloroP/).

For example, it is possible to use the plastidic signal sequence of the ferrodoxin:NADP+oxidoreductase (FNR) from spinach. This sequence comprises the 5'-untranslated region and the flanking transit peptide sequence of the cDNA of the plastidic protein ferrodoxin:NADP+oxidoreductase from spinach (nucleotide −171 to +165; Jansen et al., Current Genetics 13 (1988), 517-522).

Another plastidic signal sequence which can be used is for example the transit peptide of the waxy protein from maize plus the first 34 amino acids of the mature waxy protein (Klösgen et al., Mol Gen Genet. 217 (1989), 155-161). Moreover, it is also possible to use the transit peptide of the waxy protein from maize (see above) without the first 34 amino acids of the mature waxy protein.

The use of the following plastidic signal sequences is also feasible: signal sequence of the ribulose bisphosphate carboxylase small subunit (Wolter et al., Proc. Natl. Acad. Sci. USA 85 (1988), 846-850; Nawrath et al., Proc. Natl. Acad. Sci. USA 91 (1994), 12760-12764); signal sequence of NADP-malate dehydrogenase (Gallardo et al., Planta 197 (1995), 324-332); signal sequence of glutathione reductase (Creissen et al., Plant J. 8 (1995), 167-175), EPSPS signal sequence (U.S. Pat. No. 5,188,642). It is preferred to use the signal sequence of the dul gene from rice.

The recombinant nucleic acid molecule may comprise one or more, preferably two, signal sequences. In this context, the signal sequences may be present in the direction of transcription directly one after the other, or else they may be separated from one another in each case by what is known as a spacer. Plastidic signal sequences which comprise two signal sequences are described for example in EP 0 508 909 and EP 0 924 299, U.S. Pat. No. 5,510,471.

In a particularly preferred embodiment, the nucleic acid molecules according to the invention are thus linked to a vacuolar targeting sequence in order to bring about the transport of the formed protein into the plant vacuole, where the synthesis of alternan can take place in particularly high yield owing to the sucrose concentration, which is high locally. To ensure localization in the vacuole, it is feasible to use one of the following transit proteins: the N-terminal sequence (146 amino acids) of the patatin protein (Sonnewald et al., Plant J. 1 (1991), 95-106) or the signal sequences which are described in Matsuoka and Neuhaus, Journal of Experimental Botany 50 (1999), 165-174; Chrispeels and Raikhel, Cell 68 (1992), 613-616; Matsuoka and Nakamura, Proc. Natl. Acad. Sci. USA 88 (1991), 834-838; Bednarek and Raikhel, Plant Cell 3 (1991), 1195-1206; Nakamura and Matsuoka; Plant Phys. 101 (1993), 1-5.

To ensure localization in the plastids, in the mitochondrion or in the apoplasts, it is also possible to use one of the transit peptides which are described in WO 00/47727 on page 25/26 and in U.S. Pat. No. 5,510,471 (OTP signal peptide for targeting to plastids).

The transgenic plants may, in principle, be plants of any plant species, i.e. both monocotyledonous and dicotyledonous plants. They are preferably useful plants, i.e. plants which are grown by man for food or else for technical, in particular industrial, purposes. They are preferably starch-storing plants, for example cereal species such as rye, barley, oats, wheat, millet/sorghum, sago and the like, rice, pea, marrowfat pea, cassava, potato, tomato, oilseed rape, soybean, hemp, flax, tobacco, sunflower, cowpea or arrowroot, fiber-forming plants such as, for example, flax, hemp, cotton, oil-storing plants such as, for example, oilseed rape, sunflower, soybean, and protein-storing plants such as, for example, leguminous plants, cereals, soybean. The invention also relates to fruit trees and palms. The invention furthermore relates to fodder plants such as, for example, fodder grasses and forage grasses (such as, for example, alfalfa, clover, rye grass), and vegetable plants, such as tomato, lettuce, chicory, and ornamentals such as, for example, tulips and hyacinths.

The plants according to the invention are most preferably sugarcane, sugar beet, sugar sorghum, potato plants, maize, rice, wheat or tobacco.

The invention also relates to a method of generating genetically modified plant cells and genetically modified plants which, in comparison with the not genetically modified wild-type cells/not genetically modified wild-type plants, synthesize alternan.

The method according to the invention comprises the following steps:
  a) introducing, into a plant cell, a nucleic acid molecule which codes for a truncated alternan sucrase or a vector which comprises such a nucleic acid molecule,
  b) regenerating a plant from plant cells obtained in step a), and
  c) if appropriate, the generation of further plants with the aid of the plants obtained in step b).

Nucleic acid molecules which code for a truncated alternan sucrase and vectors which comprise such a nucleic acid molecule have been described above.

As regards the introduction, into a plant cell, of foreign nucleic acid molecules in accordance with step a) of the method of generating a genetically modified plant this may, in principle, take the form of any type of introduction of nucleic acid molecules which is suitable for integrating a foreign nucleic acid molecule into a plant cell or plant. Such methods have already been described above and can be applied here analogously.

The regeneration of plants, depending on the methods of step b) and/or c) of the methods according to the invention, can be accomplished by methods which are known to the skilled worker (for example described in "Plant Cell Culture Protocols", 1999, edt. by R. D. Hall, Humana Press, ISBN 0-89603-549-2).

The generation of further plants depending on the method in accordance with step c) or d) of the methods according to the invention can be accomplished for example by vegetative propagation (for example via cuttings, tubers or via callus culture and regeneration of intact plants) or by generative propagation. In this context, generative propagation preferably takes place under controlled conditions, i.e. selected plants with specific properties are crossed with each other and propagated. The selection is preferably accomplished in such a way that the plants, dependent on the method in accordance with step b) or d), comprise the modifications introduced in step a).

The invention also relates to propagation material of the plants according to the invention which comprises plant cells according to the invention. In this context, the term "propagation material" comprises those components of the plant which are suitable for generating progeny via vegetative or generative route. Material which is suitable for vegetative propagation is, for example, cuttings, callus cultures, rhizomes or tubers. Other propagation material comprises for example fruits, seeds, seedlings, cell cultures and the like. The propagation material is preferably propagation material from sugarcane, sugar beet, sugar sorghum, potato plants, maize, rice, wheat or tobacco.

In a further aspect, the present invention relates to a method of producing a protein according to the invention with the enzymatic activity of an alternan sucrase, in which the protein is expressed in a plant according to the invention and, in a further step, extracted and isolated. To this end, the plant according to the invention can be grown and cultured under suitable growth conditions until, as the result of protein biosynthesis, the protein with the enzymatic activity of an alternan sucrase is formed in its cells, which comprise a nucleic acid molecule according to the invention. Thereafter, the protein according to the invention can be obtained, by means of customary methods, from the plant or from parts of the plant or from propagation material of the plant in which protein with the enzymatic activity of an alternan sucrase is present. Conventional method steps comprise for example comminuting the plant material and extracting and purifying the protein.

Preferably, the method of producing a protein with the enzymatic activity of an alternan sucrase, comprises the steps that
1) a plant cell is transformed with
   a) a nucleic acid molecule whose sequence codes for the amino acid sequence of an above-described protein with the enzymatic activity of an alternan sucrase, the nucleic acid molecule being obtainable from a nucleic acid molecule with a sequence shown in SEQ ID NO 1 or 3, or
   b) a vector or plasmid comprising a nucleic acid molecule in accordance with a),
2) a plant is regenerated from the plant cells obtained in step 1),
3) the protein is expressed in the plant and subsequently extracted and isolated.

The amino acid sequences of the proteins according to the invention with the enzymatic activity of an alternan sucrase are indicated further above and defined with reference to SEQ ID NO 2. Starting from the amino acid sequences, a person skilled in the art can determine suitable coding nucleic acid sequences which, owing to the degeneracy of the genetic code, may differ. Determining a coding nucleic acid sequence and generating such a nucleic acid sequence by means of PCR have already been described above in the method of producing the protein according to the invention from transformed host cells which are grown in culture medium. As regards the vectors and plasmids which may be employed in the above method, reference is made elsewhere to the disclosure in question. Furthermore, host cells and techniques for the transformation of plant host cells which can be employed in the above method are disclosed extensively elsewhere in the present description.

The invention also relates to plant parts of the above-described plants according to the invention which may be harvested, such as, for example, of fruits, seeds, tubers, leaves or root stocks or stems, where the harvestable plant parts comprise plant cells according to the invention.

In a further aspect, the present invention relates to an alternan with a weight average of the molecular weight Mw in the range of from 12 000 000 to 30 000 000 g/mol.

In the present invention, the term "alternan" refers to a polysaccharide composed of glucose units. The glucose units are linked with one another via α-1,3 and α-1,6-glycosidic bonds, where these two types of bonds predominantly alternate. In addition, the alternan according to the invention may comprise branches.

The alternan according to the invention preferably has a weight average of the molecular weight Mw in the range of from 14 000 000 to 28 000 000 g/mol, even more preferably 16 000 000 to 26 000 000 g/mol, more preferably 18 000 000 to 23 000 000 g/mol and most preferably 19 000 000 to 23 000 000 g/mol. The molecular weight is determined by means of the GPC-MALLS method, which is described in greater detail in the use examples.

Thus, the alternan according to the invention has a markedly higher average molecular weight than described for native alternan (Mw $10^6$-$10^7$, e.g. WO 03/010177) and also a markedly higher molecular weight than described in WO 2004/023891 and US 2006/0127328.

The present invention furthermore relates to various methods for the production of the alternan according to the invention.

Firstly, the present invention comprises a method for the production of the alternan according to the invention in which
1) a solution comprising sucrose is brought into contact with a protein with the enzymatic activity of an alternan sucrase, and
2) alternan is isolated from the solution, where, in the method, the protein
   a) has an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and ends in the region from the amino acid at position 1295 to the amino acid at position 1520 of SEQ ID NO 2, or
   b) has an amino acid sequence (modified sequence) with at least 70%, more preferably at least 80%, in particular at least 90%, even more preferably at least 95% and most preferably at least 98% identity with an amino acid sequence of a), where the modified amino acid sequence preferably has the same number of amino acids, as the sequence of a).

The invention thus relates to a method for the production of alternan in-vitro with the aid of a cell-free enzyme preparation. In comparison with the synthesis of alternan in a system which is not cell-free, this method has the advantage that the reaction conditions can be controlled better and that the reaction products are considerably purer and can be purified with greater ease.

The protein with the enzymatic activity of an alternan sucrase can be obtained for example by transforming a host cell with a vector according to the invention as described above and propagating the host cells under suitable conditions. The expressed protein can then be obtained from the host cells. A protein extract may be formed by destroying the host cells, for example using a French press, and this protein extract is employed in the method according to the invention. In principle, it is possible to use all known techniques for isolating protein from host cells. *E. coli* is very particularly preferred as the host cell.

In a further variant for obtaining the protein with the enzymatic activity of an alternan sucrase, microorganisms which secrete such a protein are cultured in a sucrose-free medium, which permits the formation of the protein, until the stationary phase has been reached. After the cells have been separated from the culture medium by centrifugation, the secreted enzyme can be obtained from the supernatant. The enzyme can subsequently be added to sucrose-comprising solutions in order to synthesize alternan.

A protein which is preferably used in the above-described method is a protein with the enzymatic activity of an alternan sucrase which a) has an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and preferably in the region from the amino acid 1 to 40 of SEQ ID NO 2 and which ends in the region from the amino acid at position 1300 up to the amino acid at position 1420 of SEQ ID NO 2, or which b) has an amino acid sequence (modified sequence) which has at least 70%, more preferably at least 80%, in particular at least 90%, even more preferably at least 95% and most preferably at least 98% identity with an amino acid sequence of a), where the modified sequence preferably has the same number of amino acids, as the sequence of a).

A protein which is even more preferably used in the above-described method is a protein with the enzymatic activity of an alternan sucrase which a) has an amino acid sequence which starts in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1300 up to the amino acid at position 1340 of SEQ ID NO 2, or which b) has an amino acid sequence (modified sequence) which has at least 70%, more preferably at least 80%, in particular at least 90%, even more preferably at least 95% and most preferably at least 98% identity with an amino acid sequence of a), where the modified sequence preferably has the same number of amino acids, as the sequence of a).

In a further advantageous embodiment, the above-described method employs a protein with the enzymatic activity of an alternan sucrase which a) has an amino acid sequence which starts at in the region from the amino acid at position 1 to the amino acid at position 350, preferably in the region from the amino acid 1 to 300, more preferably in the region from the amino acid 1 to 200, even more preferably in the region from the amino acid 1 to 100 and most preferably in the region from the amino acid 1 to 40 of SEQ ID NO 2 and which ends in the region from the amino acid at position 1310 up to the amino acid at position 1320 of SEQ ID NO 2, or which b) has an amino acid sequence (modified sequence) which has at least 70%, more preferably at least 80%, in particular at least 90%, even more preferably at least 95% and most preferably at least 98% identity with an amino acid sequence of a), where the modified sequence preferably has the same number of amino acids, as the sequence of a).

Most preferably, the protein with the enzymatic activity of an alternan sucrase, which protein is employed in the method according to the invention, has one of the following sequences:

a) a sequence from the amino acid at position 40 up to and including the amino acid at position 1380 of SEQ ID NO 2 b) a sequence from the amino acid at position 40 up to and including the amino acid at position 1315 of SEQ ID NO 2 c) a sequence from the amino acid at position 40 up to and including the amino acid at position 1506 of SEQ ID NO 2 d) a sequence (modified sequence) which has at least 70%, more preferably at least 80%, in particular at least 90%, even more preferably at least 95% and most preferably at least 98% identity with the sequence of a), b) or c) where the modified sequence preferably has the same number of amino acids, as the sequence of a).

Moreover, the above-described method may also employ all those above-described proteins with the enzymatic activity of an alternan sucrase which are truncated in comparison with an abovedefined full-length alternan sucrase of the N- and/or C-terminal end of the amino acid sequence ("truncated alternan sucrase") and which are encoded by nucleic acid molecules according to the invention with the corresponding sequence.

In one embodiment of the invention, a methionine is located upstream of the N terminus of the proteins described hereinabove and hereinbelow, with the enzymatic activity of an alternan sucrase, which proteins are employed in the method according to the invention. In this preferred embodiment, methionine thus forms the new N terminus of the protein employed in the method according to the invention. Such a methionine usually originates from the translation of the RNA which codes for the protein, and is encoded in the translation by the nucleic acid triplet ATG.

Preferably excepted by the method according to the invention are the truncated proteins with the enzymatic activity of an alternan sucrase which are described in US20060127328A1, in particular the proteins described in paragraph [0089] and in FIGS. 3A and 3B of US20060127328A1. Preferably excepted from the present invention are thus the proteins from the amino acid at position 1 to 1425, position 1 to 1349, position 1 to 290, position 342 to 1425 and position 342 to 1290, with the positions being defined with reference to the appended SEQ ID NO 2.

A preferred embodiment of the method according to the invention employs a purified protein with the enzymatic activity of an alternan sucrase. A purified protein is understood as meaning a protein which is largely free from cellular components of the cells in which the protein is synthesized, and/or lacks contamination with proteins which have polysaccharide-synthesizing activities (for example dextran sucrases) or polysaccharide-degrading activities and/or which comprise (polysaccharide) acceptors. Preferably, the term "purified protein with the enzymatic activity of an alternan sucrase" denotes a protein with a degree of purity of at least 70%, preferably of at least 85% and particularly preferably of at least 95%.

The use of a purified protein for the production of alternan has a variety of advantages. In comparison with methods employing partially purified protein extracts, the reaction medium of the method according to the invention comprises no remainders of the production strain (microorganism) which is used for genetically producing the protein.

Moreover, the use of the purified protein involves advantages for the use in the food and pharmaceuticals industries. As a result of the defined composition of the reaction medium, which composition has been freed from all unnecessary components, the product too is defined more precisely regarding its components. This leads to a considerably less complicated licensing procedure for these biotechnological products in the food and pharmaceuticals industries, in particular because these products should comprise no traces of a transgenic microorganism.

Moreover, it is possible, with the aid of this method according to the invention, to produce alternan in high yields, without losses as the result of, for example, the interfering secondary activity of other host cell enzymes which may form interfering secondary products.

In a further preferred embodiment of the method according to the invention, a recombinantly produced protein with the enzymatic activity of an alternan sucrase is used.

In yet a further preferred embodiment, the protein with the enzymatic activity of an alternan sucrase is immobilized on a support.

The immobilization of the protein according to the invention with the enzymatic activity of an alternan sucrase has the advantage that the enzyme, being a catalyst of the synthesis reaction, can be recovered in a simple manner from the reaction mixture and be reemployed. Since the purification of enzymes is, as a rule, expensive and time-consuming, an immobilization and recovery of the enzyme allows considerable savings to be made. A further advantage is the degree of purity of the reaction products, which comprise no residual protein.

A multiplicity of supports is available for the immobilization of proteins, their coupling to the support being possible via covalent or noncovalent bonds (for an overview see: Methods in Enzymology 135, 136, 137). Widely used supports are, for example, agarose, alginate, cellulose, polyacrylamide, silica or nylon.

The support may be for example an inert support, an electrically charged support, an inorganic support or an organic support. Suitable supports which may be used are inorganic materials such as porous glasses, silica gel, alumina, hydroxyepatite or various metal oxides, natural polymers, for example cellulose, starch, alginates, agarose or collagen, or synthetic polymers such as polyacrylamide, polyvinyl alcohol, methyl acrylate, nylon or oxirans. Immobilization is accomplished by physical binding forces such as, for example, Van-der-Waals forces, hydrophobic interactions and ionic bonds. The protein with the enzymatic activity of an alternan sucrase may, as mentioned above, also be immobilized on supports by means of covalent bond. To this end, the supports must display reactive groups, which are capable of forming homopolar bonds with amino acid side chains. Examples of suitable groups are carboxyl groups, hydroxyl groups and sulfide groups. For example, the surface of porous glasses can be activated by treatment with silanes and subsequently reacted with proteins. Hydroxyl groups of natural polymers may be activated with cyanogen bromide, and carboxyl groups with thionyl chloride, and subsequently coupled with enzymes. Another possibility of immobilizing the protein with the enzymatic activity of an alternan sucrase is its inclusion in three-dimensional networks. One advantage is that the enzymes are present in free, unbound form in the network. Pores of the surrounding matrix must be sufficiently small to retain the enzyme.

In a preferred embodiment of the above-described method according to the invention, the solution comprising sucrose is an aqueous solution with a sucrose concentration of at least 12% by weight, even more preferably at least 15% by weight, based on the weight of the water. The sucrose concentration is particularly preferably 15% by weight-40% by weight based on the weight of the water, more preferably 15% by weight-30% by weight and most preferably 18% by weight-25% by weight.

Method step 1), in which a solution comprising sucrose is brought into contact with a protein with the enzymatic activity of an alternan sucrase, is preferably carried at a temperature of from 35-45° C., even more preferably at 35-40° C.

The pH in the method according to the invention is preferably 5-6, even more preferably 5.0-5.3.

The reaction time in step 1 of the method amounts to preferably at least 12 hours, more preferably to at least 24 hours, even more preferably to at least 36 hours, particularly preferably to 40-60 hours.

In a further advantageous variant, the method is carried out without stirring.

In one variant of the above-described method, an acceptor molecule is added in method step 1). Within the context of the present invention, an acceptor molecule is understood as meaning a molecule on which a truncated alternan sucrase is capable of catalyzing a chain-elongation reaction, with an alternan chain forming on the acceptor molecule. The acceptor which may be added to the reaction mixture at the beginning of the reaction is preferably a carbohydrate or a carbohydrate derivative. The carbohydrate acceptor is preferably an oligo- or polysaccharide, in particular a branched polysaccharide such as for example, dextrin, glycogen or amylopectin, preferably a linear polysaccharide and particularly preferably a saccharide selected from the group consisting of maltose, isomaltose, isomaltotriose and methyl-alpha-D-glucan or gentobiose. If an alternan chain elongation takes place on these acceptors, this gives rise to products with a higher molecular weight in comparison to the starting material. When maltose, isomaltose, isomaltotriose and methyl-alpha-D-glucan are used, products are obtained which have a reduced molecular weight in comparison with the alternan which can be prepared in the absence of external carbohydrate acceptors, which products are here referred to as oligoalternans. The size of the molecular weight of the oligoalternans prepared depends on the sucrose:acceptor ratio employed. Thus, the degree of polymerization of the products increases with an increasing sucrose:acceptor ratio. Moreover, the sucrose:acceptor ratio affects the oligoalternan yield. Thus, in the case of isomaltose acceptor, the oligoalternan yield increases with a decreasing sucrose:isomaltose ratio.

In a further method, alternan is obtained by extracting alternan from a host cell according to the invention or a plant according to the invention or its propagation material or from above-described harvested plant parts, and, if appropriate, isolating it.

An advantageous embodiment provides that the alternan is isolated from plants according to the invention, in particular from their vacuoles, and purified. It is particularly preferred to isolate, and obtain, alternans from the storage organs of potato, maize, sugar beet, sugar sorghum or sugarcane plants. In one embodiment, the method comprises the mechanical comminution of larger plant cell biomass with the aid of a turbine mixer, for example a Waring blender, where comminution is preferably carried out in a large volume of aqueous medium at low temperatures, for example 4° C. Further disruption can be carried out with the aid of physical disruption methods, for example by means of ultrasound, a French press device, with mills or presses, with the aid of chemical disruption methods, for example lyophilization or using detergents or using changes in osmotic pressure, or with the aid of biological disruption methods, for example using enzymes which attack the cell wall, or by means of an acid/alkali treatment. In a particularly preferred embodiment, the alternan is obtained by producing an aqueous extract, in particular of the storage organs, and subsequent precipitation with alcohol, or at low temperatures, for example 4° C.

Further variants of the method of obtaining alternan by extraction/isolation from a host cell according to the invention, plant according to the invention or its propagation material or harvestable plant parts can be found by the skilled worker in the known specialist literature, such as, for example, Loncin, Marcel Grundlagen der Verfahrenstechnik in der Lebensmittelindustrie [Basics of method engineering in the food industry]. Frankfurt/Main: Verlag Sauerländer 1969; Tscheuschner, H. D. Grundzüge der Lebensmitteltechnik [Basics of food technology]. Hamburg: Behrs Verlag 2004; Kessler, H. G. Lebensmittel- und Bioverfahrenstechnik [Food and bioprocess technology]. Munich: Verlag A. Kessler 1996; Martin, A. M. Bioconversion of waste materials to industrial products. London, N.Y.: Blackie Academic&Professional 1998.

If the plant cell/plant according to the invention takes the form of a sugar-storing plant such as, for example, sugar beet or sugarcane, or propagation material or harvestable plant parts thereof, established extraction protocols for sugars are available to the skilled worker, such as those described for example in Belitz & Grosch. Lehrbuch der Lebensmittelchemie [Textbook of food chemistry], Berlin Heidelberg, Springer-Verlag 1992, p. 786.

The extraction and isolation of the alternan from a plant according to the invention or its propagation material can be performed by means of standard methods such as, for example, precipitation, extraction and chromatographic methods.

In yet a further method according to the present invention, a protein according to the invention with the enzymatic activity of an alternan sucrase, as described above (hereinbelow alternan sucrase), produced by a host cell according to the invention, preferably E-coli, is secreted into a culture medium comprising sucrose, and alternan is isolated from the culture medium.

Such a method is described in WO 00/47727. The relevant parts of the disclosure including the preferred embodiments, in particular p. 28, 3rd paragraph up to and including p. 31, 1st paragraph, of WO 00/47727 are expressly incorporated by reference, and the citations are part of the disclosure of the present invention.

The alternan of the present invention is a white dry powder which is clear to opaque in solution. It shows a high solubility and the solution has a low viscosity, as shown in the appended examples. Alternan of the present invention has no flavor and a clean taste. Moreover, alternan of the present invention is microbially inert, non-digestible, low to non-caloric, and has a very low glycemic index and glycemic response.

In one aspect, the present invention relates to the use of alternan according to the invention as addition to foodstuffs or dietary supplements. The term foodstuff includes according to the present invention both foodstuffs for humans and animal foodstuffs or animal feed. Moreover, the term foodstuff includes beverages. The dietary supplements include dietary supplements for humans and for animals.

In foodstuffs and dietary supplements, alternan according to the invention can particularly be used as an emulsifier, substitute for gum arabic, filler, bulking agent, decompacting agent, extender, prebiotic agent and/or dietary fiber. Preferred foodstuffs are, without limitation, beverages, such as carbonated beverages, juices, especially fruit juices, smoothies, lemonades, ice tea, diet drinks, satiety drinks, finished drinks, sports drinks, stamina drinks, powdered drink mixtures for dietary supplementation, bakery products, such as bread, cakes, cookies, biscuits, crackers, croissants, noodles and pasta, nutrition bars, energy bars, breakfast bars, snack products and cereals, such as extruded cereals, breakfast cereals, cereal chips, infant and baby food, soups, deep-frozen meals, ready-to-serve meals, and meal-replacements.

In a preferred embodiment, alternan according to the invention is used as a dietary fiber. In this connection it is particularly useful for fiber enrichment in the above mentioned foodstuffs.

In a further aspect, the present invention thus also relates to foodstuffs and dietary supplements which comprise alternan according to the invention as emulsifier, substitute for gum arabic, filler, bulking agent, decompacting agent, extender, prebiotic agent and/or dietary fiber, wherein the above-mentioned exemplary foodstuffs are highly preferred. More preferably the present invention relates to foodstuffs and dietary supplements which comprise alternan according to the invention as a dietary fiber, wherein the above-mentioned exemplary foodstuffs are most preferred.

In still another aspect, the present invention relates to the use of alternan according to the invention as addition to cosmetics or pharmaceuticals. In these products it can be used as an emulsifier, filler, decompacting agent, extender, and/or as an excipient for active ingredients.

DESCRIPTION OF THE SEQUENCES

SEQ ID NO 1: Nucleic acid sequence from *Leuconostoc mesenteroides*, coding for a protein with the enzymatic activity of an alternan sucrase SEQ ID NO 2: Amino acid sequence of a protein with the enzymatic activity of an alternan sucrase from *Leuconostoc mesenteroides*. The amino acid sequence shown can be derived from SEQ ID NO 1.

SEQ ID NO 3: Synthetic nucleic acid sequence codes for a protein with the enzymatic activity of an alternan sucrase. The synthesis of the codons of the sequence shown was carried out in such a way that it is adapted to the use of codons in plant cells. The nucleic acid sequence shown codes for a protein with the amino acid sequence shown in SEQ ID No 2.

SEQ ID NO 4: Synthetic primer GUS-ForwI
SEQ ID NO 5: Synthetic primer GUS-Rev
SEQ ID NO 6: Synthetic primer GUS-ForwII
SEQ ID NO 7: Synthetic linker sequence Linker1
SEQ ID NO 8: Synthetic linker sequence Linker2
SEQ ID NO 9: Synthetic primer Nos-Forw
SEQ ID NO 10: Synthetic primer Nos-Rev
SEQ ID NO 11: Synthetic oligonucleotide, 5' extension before nucleotide 118 of SEQ ID NO 3
SEQ ID NO 12: Synthetic oligonucleotide, 3' extension of SEQ ID NO 3
SEQ ID NO 13: Synthetic primer RLP3
SEQ ID NO 14: Synthetic primer RLP4
SEQ ID NO 15: Synthetic primer AlSuI-Forw
SEQ ID NO 16: Synthetic primer AlSuI-Rev SEQ ID NO 17: Synthetic primer AlSuII-Forw
SEQ ID NO 18: Synthetic primer AlSuII-Rev
SEQ ID NO 19: Synthetic primer SIP6
SEQ ID NO 20: Synthetic primer SIP7
SEQ ID NO 21: Synthetic primer SIP1a
SEQ ID NO 22: Synthetic primer SIP2
SEQ ID NO 23: Synthetic primer SIP3
SEQ ID NO 24: Synthetic primer SIP4
SEQ ID NO 25: Synthetic primer SIP5

The present invention is described hereinbelow with reference to use examples, which, however, are not intended to limit in any way the scope of protection as specified in the appended claims.

1. METHODS

1.1 Plasmid Construction

All molecular-biological methods were carried out by means of standard methods (Sambrook & Russell Molecular cloning: a laboratory manual (third edition) Cold Spring Harbor Laboratory Press, NY, USA (2001)). The restriction enzymes were obtained from New England Biolabs, Inc., Ipswitch, Mass., USA.

pUbiGusNos

The ubiquitin promoter of Zea mays (Gen-Bank Accession 94464, Christensen et al., Plant Mol. Biol. 18, 1992, 675)) from pML8 (WO 2006 066969) was cleaved with PstI and ligated into PstI-cleaved pUC18 (GenBank Accession number L09136) in an orientation such that the 5' end of the promoter was on the side of the HindIII site, which resulted in pUC18-Ubi. The beta-glucuronidase (GUS) coding sequence of E. coli (GenBank Accession number S69414) was amplified with the primers GUS-ForwI (SEQ ID NO 4; GAAAGCTTGGCTGCAGGTCAGTCCCT-TATGTTACGTCCTGTAG) and GUS-Rev (SEQ ID NO 5; CTGGTCCCGGGATTCATTGTTTGCCTCCCTGCT),
PCR conditions: 5 cycles of in each case 30 sec at 94° C., 30 sec at 60° C., 2 min at 72° C., and 25 cycles with in each case 30 sec at 94° C., 30 sec at 73° C., 2 min at 72° C., using Platinum Taq DNA polymerase High Fidelity (Invitrogen Corp, Carlsbad, Calif., USA) and proceeding under the conditions described by the manufacturer. The resulting fragment was reamplified with the primers GUS-ForwII (SEQ ID NO 6; TCGAGCTCGCGAAAGCTTGGCTGCAGGT) and GUS-Rev under the same conditions and cleaved with XmaI. pUC18-Ubi was cleaved with BamHI, the overhangs were filled up with T4 DNA polymerase (New England Biolabs, Inc., Ipswitch, Mass., USA), and the fragment was cleaved with XmaI. The XmaI-cleaved GUS PCR product was ligated into this vector, and the resulting plasmid was named pUC18-Ubi-GUS. pUC18-Ubi-GUS was cleaved with XmaI, and the overhangs were removed with mung bean nuclease (New England Biolabs, Inc., Ipswitch, Mass., USA), and the fragment was cleaved with EcoRI. The phosphorylated oligonucleotides Linker1 (SEQ ID NO 7; AACAACTCTCCTG-GCGCACCATCGTCGGCTACAGCCTCGGGAATTGCT-GCAGGTC GACGGATCCG) and Linker2 (SEQ ID NO 8; AATTCGGATCCGTCGACCTGCAGCAAT-TCCCGAGGCTGTAGCCGACGATGGTGCG CCAG-GAGAGTTGTT) were annealed, and the resulting linker was ligated into this XmaI/EcoRI-cleaved vector fragment, resulting in pUC18-Ubi-GUS-PL. The nos terminator from Agrobacterium tumefaciens (Depicker et al., 1982, Journal of Molecular and Applied Genetics 1, 561-573) was amplified from pML8 using the primers Nos-Forw (SEQ ID NO 9; CGGATCGGATCCGTCGACCTGCA-GATCGTTCAAACATTTGGCAAT) and Nos-Rev (SEQ ID NO 10; CCACGGAATTCGATCTAGTAACATAGAT-GACACCGCG). PCR conditions: 5 cycles with in each case 30 sec at 94° C., 30 sec at 58° C., 3 min at 72° C., and 25 cycles with in each case 30 sec at 94° C., 30 sec at 70° C., 3 min at 72° C., using Platinum Taq DNA polymerase High Fidelity (Invitrogen Corp, Carlsbad, Calif., USA) and proceeding under the conditions described by the manufacturer. The PCR product was cleaved with BamHI and EcoRI and ligated into BamHI/EcoRI-cleaved pUC18-Ubi-GUS-PL, which resulted in the vector pUbiGusNos.

pSM13

The alternan sucrase coding, codon-optimized sequence was synthesized at Entelechon (Regensburg, Germany). The predicted splicing sites and the poly(A) signals were removed.

Furthermore, no GC/AT stretches longer than 5, or 6, nucleotides, respectively, and no CAAT sequences exist in the codon-optimized sequence. Certain restriction cleavage sites were removed or added. The synthetic sequence comprises the nucleotides 118-6174 from SEQ ID NO 3, with the 5' extension GCGGCCGCGGCAGCC<u>ATG</u> [SEQ ID NO 11], so that an ATG translations start codon [underlined] is introduced upstream of nucleotide 118 of SEQ ID NO 3, and with the 3' extension ACCGGATATCGCGGCCGC [SEQ ID NO 12]). The synthetic sequence was cloned into pUC19 (New England Biolabs; GenBank accession number M77789) using EcoRI/HindIII and using the HindIII restriction cleavage site in the synthetic alternan sucrase coding sequence, which gave pRVL110. The stop codon (underlined in RLP3) was reintroduced by annealing the phosphorylated primers RLP3 (SEQ ID NO 13; AGCT<u>TGA</u>ACCGGATATCGCGGCCGC) and RLP4 (SEQ ID NO 14; AGCTGCGGCCGCGATATCCGGTTCA) and ligating the resulting linker into HindIII-cleaved pRVL110, with the orientation of the linker such that RLP3 was in sense orientation downstream of the alternan sucrase coding sequence. The resulting plasmid was named pSM12.

The 5' segment of the alternan sucrase from pSM12 was amplified with the primers AlSuI-Forw (SEQ ID NO 15; CAACTGAGCTCTGCAGAATTCGGCTTGT-TCGGGCAGCCATGGACACCAACTCC) and AlSuI-Rev (SEQ ID NO 16; GCCGGAGTTGTCGGTGCCGAAGC-CCTTGCG). PCR conditions: 5 cycles with in each case 30 sec at 94° C., 30 sec at 65° C., 3 min at 72° C., and 25 cycles with in each case 30 sec at 94° C., 30 sec at 72° C., 5 min at 72° C., using Platinum Taq DNA polymerase High Fidelity (Invitrogen Corp, Carlsbad, Calif., USA) under the conditions specified by the manufacturer. The product was cleaved with SacI. The resulting fragment was cloned into SacI-opened pUbiGusNos in an orientation such that the 5' end of the alternan sucrase was downstream of the ubiquitin promoter, which gave pUbiAlSuI. The 3' end of alternan sucrase was amplified on pSM12 using the primers AlSuII-Forw (SEQ ID NO 17; TCCTACGACAAGTCCTCCTTC-GAGAACGTG) and AlSuII-Rev (SEQ ID NO 18; CTTACG-GATCCACTAGTAACGGCCGCGATATCCGGTTC). PCR conditions: 5 cycles with in each case 30 sec at 94° C., 30 sec at 65° C., 3 min at 72° C., and 25 cycles with in each case 30 sec at 94° C., 30 sec at 72° C., 5 min at 72° C., using Platinum Taq DNA Polymerase High Fidelity (Invitrogen Corp, Carlsbad, Calif., USA) under the conditions specified by the manufacturer. The resulting fragment was cleaved with KpnI and BamHI and ligated into KpnI/BamHI-digested pUbiAlSuI, which gave pSM13.

pSI3

Alternan sucrase of pSM13 was amplified using the primers SIP6 (SEQ ID NO 19; GCCATCGAGCAGCAGATCTC- CCTCAAG) and SIP7 (SEQ ID NO 20; CATAGGATC-CCTACACGCCGGAGGCGTC). By doing so, a TAG stop codon (complementary sequence underlined in SIP7) was introduced after nucleotide 3945 of SEQ ID NO 3. PCR conditions: 30 cycles with in each case 10 sec at 95° C., 2 min at 71° C., 3 min+15 sec autoextension per cycle 68° C., followed by 5 min at 72° C., using Platinum Taq DNA Polymerase High Fidelity (Invitrogen Corp, Carlsbad, Calif., USA) and proceeding as specified by the manufacturer. The PCR product was cleaved with DraIII and BamHI and cloned into the DraIII/BamHI vector fragment pSM13. The resulting plasmid was named pSI3.

pSR16 pSR16 was generated by cleavage of pSM13 with XbaI and SalI, and ligating the fragment containing Alternansucrase in the XbaI-SalI vector fragment from pAlsu-pET24a (WO 00/47727). The protein encoded by pSR16 comprises the amino acids 40-2057 of SEQ ID NO 2 plus one methionine at the N terminus. This protein is called full length alternansucrase in the below examples.

pSR17 pSR17 was cloned by cleaving pSI3 with XbaI and SalI and ligating the fragment which comprises alternan sucrase into the XbaI-SalI vector fragment of pAlsu-pET24a (WO 00/47727). The protein encoded by pSR17 comprises the amino acids 40-1315 of SEQ ID NO 2 plus one methionine at the N terminus. This protein is called truncated alternansucrase in the below examples.

1.2 Expression of Alternan Sucrase in Wheat Germ Extract

In-vitro Transcription

Templates for the in-vitro transcription were generated by means of PCR. The PCR conditions were as follows: 35 cycles with in each case 10 sec at 94° C., 2 min at 71° C., 3 min at 68° C., followed by 5 min at 72° C. The polymerase used was Platinum Taq DNA polymerase High Fidelity (Invitrogen Corp, Carlsbad, Calif., USA) proceeding as specified by the manufacturer. The PCR was carried out on pSM13 using the following primers: SIP1a (SEQ ID NO 21; TAATACGACT-CACTATAGGCAGAATTCGGCTTGTTCGGGC) and SIP2 (SEQ ID NO 22; AGTAACGGCCGCGATATCCGGT-TCAAGC) (product codes for the amino acids 40-2057 of SEQ ID NO 2 plus one methionine at the N terminus); SIP1a-SIP3 (SEQ ID NO 23; CGAAGAGGCCGTC CTAGCGGAGGGAG), where a TAG stop codon was incorporated after nucleotide 4518 of SEQ ID NO 3 (complementary sequence underlined in SIP3) (product codes for the amino acids 40 to 1506 of SEQ ID NO 2 plus one methionine at the N terminus); SIP1a-SIP4 (SEQ ID NO 24; GGTGC-CGAAGCCCTAGCGGAGCTC), where a TAG stop codon was incorporated after nucleotide 4140 of SEQ ID NO 3 (complementary sequence underlined in SIP4) (product codes for the amino acids 40 to 1380 of SEQ ID NO 2 plus one methionine at the N terminus); SIP1a-SIP5 (SEQ ID NO 25; CCGGAGATGGAGTAGTACTACACGCCGGA), where a TAG stop codon was incorporated after nucleotide 3945 of SEQ ID NO 3 (complementary sequence underlined in SIP5) (product codes for amino acids 40 to 1315 of SEQ ID NO 2 plus one methionine at the N terminus).

The in-vitro transcription was carried out with the Ambion mMessage mMachine Kit (Ambion, Austin, Tex., USA) using T7 RNA polymerase and following the protocols provided by the manufacturer.

In-vitro Translation

The above-described mRNAs were translated in a wheat germ extract from Promega (Promega, Madison, Wis., USA), following the protocols provided by the manufacturer.

Determination of the Amount of Alternan Sucrase

The in-vitro translation was carried out as described above in the presence of 35S-labeled methionine. The proteins were separated on SDS/8% polyacrylamide gel and visualized by means of autoradiography.

1.3 Expression of Alternan Sucrase in Potato Protoplasts

Potato protoplasts were generated by incubating cut-off leaf material of in-vitro potato plants overnight in 0.5% cellulase and 0.2% Macerozyme in 0.6 M mannitol in the dark at room temperature. On the next day, the protoplasts were harvested by straining through a 125 µm and a 63 µm strainer. The protoplasts were washed with 0.6 M mannitol, counted, pelleted and suspended in MaMg medium [MaMg$_2$×6H$_2$O, 0.1% MES, pH 5.6] at a concentration of 2×10$^6$ protoplasts per ml. The protoplasts were incubated on ice for 30 minutes. For the transformation, a typical volume of 40 µl of DNA was incubated with 10$^6$ protoplasts and 1 ml [40% PEG 6000, 0.4 M mannitol, 0.1 M Ca(NO$_3$)$_2$×4H$_2$O, pH 7-9] for 20 minutes at room temperature. 10 ml of B5 SMX medium [Gamborg B5 salts and vitamins (Duchefa) supplemented with 1% sucrose, 0.4 M mannitol, 1.25 g/l xylose, 0.1 mg/l 2.4-D, 0.2 mg/l BAP, 1.0 mg/l NAA, pH 5.7] were added stepwise. The protoplasts were harvested by centrifugation, resuspended in 5 ml of B5 SMX medium per 10$^6$ transformed protoplasts and incubated overnight in the dark at 23° C. The protoplasts were harvested by centrifugation. To analyze the alternan sucrase activity, the pellet was resuspended in 100 µl [100 mM sodium citrate pH 6.5, 1 mM EDTA, 5 mM DTT], shock-frozen in liquid nitrogen to disrupt the cells, and centrifuged. The supernatant was used for the further analysis. To analyze the beta-glucuronidase (GUS) activity, the pellet was homogenized in GUS extraction buffer [50 mM NaP buffer pH 7, 10 mM EDTA, 0.1% SDS, 0.1% Triton X-100, 10 mM beta-mercaptoethanol] and centrifuged. The supernatant was used for the further analysis.

Determination of the Protoplast Transformation Efficiency

The transformation efficiency was determined by quantifying the amount of GUS synthetized. The amount of GUS was quantified by incubating 100 µg of the protein extract in 4-methylumbelliferyl glucuronide (4-MUG) at a final concentration of 1 mM. The reaction was stopped by adding 900 µl of 0.2 M Na$_2$CO$_3$ to 100 µl of reaction solution. Samples were taken at various points in time, and the amount of 4-methylumbelliferyl (MU) produced was determined in a fluorimeter with an absorption at 356 nm and an emission at 455 nm at various points in time as a measure for GUS activity. The relative transformation efficiency was expressed as the relative increase in the amount of MU formed per 100 µg of protein extract.

1.4 Determination of the Alternan Sucrase Activity

The alternan sucrase activity was determined as described in WO 00/47727, except that the polymer was stained with 0.5% Alcian Blue, 3% HAc solution.

1.5 Production of Recombinant Full Length and Truncated Alternan Sucrase and Alternans in E. coli The plasmid pSR16 (protein encoded by pSR16 comprises the amino acids 40-2057 of SEQ ID NO 2 plus methionine at N-terminus—full length alternansucrase) and pSR17 (protein encoded by pSR17 comprises the amino acids 40-1315 of SEQ ID NO 2—truncated alternansucrase) were transformed into E. coli BL21 (DE3) (Stratagene), following standard methods as described in Sambrook & Russell, Molecular cloning: a laboratory manual (third edition) Cold Spring Harbor Laboratory Press, NY, USA (2001). 50 ml of YT medium+50 µg/ml kanamycin were inoculated with 1 ml of preculture of these cells and grown at 37° C. until the OD$_{600}$ was 0.4. IPTG was added to a final concentration of 5 mM and glucose to a final concentration of 1%, and the culture was grown overnight at room temperature. The cells were harvested (15 min 4000 rpm, 4° C.), resuspended in 3 ml of extraction buffer (100 mM sodium citrate pH 5.2, 1 mM EDTA, 10 mM DTT) and disrupted twice using a French press. The crude extract was centrifuged for 10 min at 13 000 rpm, and the supernatant was sterilized (Sterivex GV 0.2 µM, Millipore) and then used for the further analysis.

Typically, 5 ml of protein extract of the truncated or full length alternan sucrase from Erlenmeyer shake flasks were incubated in a total volume of 1 liter (100 mM sodium acetate pH 5.3, 20% sucrose) for 48 hours at 37° C. without stirring. Alternan was obtained by adding EtOH to a final concentration of 50%, centrifugation for 10 minutes at 4000 rpm, washing the alternan pellets three times with 50% EtOH and drying the pellets at 37° C. The dried alternan was ground in a petal and mortar.

1.6 Determination of the Molecular Weight of Alternan

Alternan was dissolved in DMSO at a concentration of 0.1% (w/v). The solutions are incubated overnight at RT on a shaker (Eppendorf) at 300 rpm and then heated for 2 h at 95° C. in a thermal shaker (Eppendorf) at 300 rpm. The sample was filtered through a 5 µm PTFE Whatman Puradisc™ 13 mm syringe. The polymers were analyzed using a Dionex system (Dionex Corporation, Sunnyvale, USA) consisting of the following components: P680 HPLC pump, AS50 autosampler, thermostatted column compartment TCC-100. The detection is carried out using a DAWN-EOS light-scattering detector (Wyatt Technology, Santa Barbara, USA) with $\lambda_0$=690 nm and 15 detectors in the range of angles from 25.9 to 163.3° and K5 flow cell coupled to a Shodex RI-101 RI detector (Shodex Denko K.K., Kanagawa, Japan). The polymers are fractionated via the following columns: WATERS Styragel guard column, Styragel 7, Styragel 6E, and Styragel 2 (Waters Corp, Milford, Mass., USA). 50 µl of solution are injected. The fractionation takes place at a temperature of 60° C. and a flow rate of 0.5 ml/min with 90 mM $NaNO_3$ in DMSO as the eluent. The molecular weight distribution of the samples is analyzed via the Astra V 5.1.7.3 program, using the mass calculation program Berry 2nd order (Wyatt Technology, Santa Barbara, USA).

1.7 Determination of the Viscosity

The viscosity of alternan solutions was determined at 23° C. as a function of the concentration, using the Gemini Advanced Rheometer from BOHLIN at a constant shear rate of 39.6 s−1. The sample is transferred into the plate/cone measuring system CP4°/40 mm which had been prewarmed to 23° C. The measurement parameters are the following: viscosimetry mode with shear-rate setting: preshearing: 10 1/s, 60s, setting time 10s; constant shear rate 39.6 s−1; per 10 data, delay time and waiting time: 5s, integration time 10s; time per point 20s. The same sample is measured twice; in the case of unduly unsteady curves three times in order to obtain a larger number of data. Data which deviates clearly from the linear curve are disregarded for calculating the mean.

2. EXAMPLES

Example 1

Activity of C Terminal Alternan Sucrase Deletion Mutants in Wheat Germ Extract

Alternan sucrase deletion mutants for expression in wheat germ extract were generated as described in the methods. The activity and the amount of the alternan produced in the wheat germ extract were determined.

FIG. 1 shows the activity and amount of the alternan sucrase in wheat germ extract. FIG. 1A shows the alternan sucrase activity and that the alternan sucrase generated using the primers SIP1a and SIP5 (i.e. the protein comprises the amino acids 40 to 1315 of SEQ ID NO 2 plus one methionine at the N terminus) is active in wheat germ extract.

FIG. 1B shows the amount of the alternan sucrase and that the production efficiency in wheat germ extract increases with decreasing protein size. The control is the in-vitro translation in the absence of RNA. The primers used for generating templates for the in-vitro transcription are shown above the lines. The E. coli alternan sucrase is full-length alternan sucrase expressed in E. coli. The molecular weight of the marker proteins are indicated on the right of FIG. 1B.

Example 2

Activity of C Terminal Alternan Sucrase Deletion Mutants in Potato Protoplasts

To express full-length alternan sucrase in potato protoplasts, 30 µg of pSM13 together with 10 µg of pUbiGusNos were transformed per $10^6$ protoplasts. To express the C terminal truncated alternan sucrase, 30 µg of pSI3 together with 10 µg of pUbiGusNos were transformed per $10^6$ protoplasts. As a control, 30 µg of pBluescriptII KS(+) (Stratagene, La Jolla, Calif., USA; Genbank Accession number X52327) together with 10 µg of pUbiGusNos or 40 µg of pBluescriptII KS(+) was transformed per $10^6$ protoplasts. The activity of the proteins was determined as described in the methods. The amount of protein extract analyzed was corrected by the relative transformation efficiency. FIGS. 2A and 2B show the results of the two different experiments. pSI3-encoded alternan sucrase was applied to the gel at different concentrations and compared with alternan sucrase encoded by pSM13. pKS-GUS is the negative control in which no alternan sucrase-encoding sequences were transformed.

The experiment shown in FIG. 2A/B demonstrates that the activity of the protein encoded by pSI3 (protein comprises the amino acids 40 to 1315 of SEQ ID NO 2 plus one methionine at the N terminus) in potato protoplasts is 5 to 40 times higher than the activity of the pSM13-encoded alternan sucrase (protein comprises the amino acids 40 to 2057 of SEQ ID NO 2 plus one methionine at the N terminus).

Example 3

Molecular Weight Determination of Alternans

Alternans were produced with truncated alternansucrase and with full length alternansucrase (comparative example) as described in 1.5. The alternan produced with truncated alternansucrase is also abbreviated hereinafter as "SR17" and the alternan produced with full length alternansucrase is also abbreviated hereinafter as "SR16".

The molecular weights of the alternans were determined by GPC MALLS (see methods) and are shown in the following table. The weight average of the molecular weight Mw of the alternan produced with the truncated alternan sucrase was 21 200 000 g/mol (SR17) and the Mw of the alternan produced with the full length alternan sucrase (SR16) was 35 300 000 g/mol (both with 1% initial concentration).

| sample | Initial concentration | Mw (g/mol) *10$^7$ | Recovery (%) |
|---|---|---|---|
| alternan produced from full length alternansucrase | 1% | 3.53 | 79.0% |
| SR16-15 | 15% | 3.56 | 59.5% |
| SR16-13 | 13% | 3.64 | 45.0% |
| SR16-12 | 12% | 3.69 | 71.1% |
| SR16-11 | 11% | 3.69 | 66.1% |
| SR16-10 | 10% | 3.74 | 83.2% |
| SR16-9 | 9% | 3.74 | 80.9% |
| SR16-8 | 8% | 3.77 | 86.8% |
| SR16-7 | 7% | 3.77 | 87.1% |
| alternan produced from truncated alternansucrase (comparative ex.) | 1% | 2.12 | 86.4% |
| SR17-15 | 15% | 2.18 | 66.5% |
| SR17-13 | 13% | 2.18 | 67.8% |
| SR17-12 | 12% | 2.22 | 90.8% |
| SR17-11 | 11% | 2.21 | 95.2% |
| SR17-10 | 10% | 2.20 | 88.0% |
| SR17-9 | 9% | 2.19 | 87.4% |
| SR17-8 | 8% | 2.21 | 89.3% |
| SR17-7 | 7% | 2.23 | 91.2% |

Alternan produced form truncated alternan sucrase was measured using 13C NMR spectrometry. To this end, the sample material was dissolved in deuterated DMSO at 80° C. with intensive stirring and measured at a temperature of likewise 80° C. using a Unity INOVA 500 spectrometer (Varian Inc., USA) at a measurement frequency of 125.69 MHz under quantitative measurement conditions (inverse gate decoupling, relaxation delay 5s). The measuring time was approximately 18 hours. The chemical shifts were related to TMS (0 ppm). The intensities of the different signals of the C1, C3 and C6 carbon group of the 1,3- and 1,6-bonds in the NMR spectrum were used to estimate a mean ratio of alpha-1,3-bonds to alpha-1,6-bonds of this alternans of 0.41/0.59 (error 0.02).

Example 4

Solubility of Alternan

Alternans were produced with truncated alternansucrase and with full length alternansucrase (comparative example) as described in 1.5. The alternan produced with truncated alternansucrase is also abbreviated hereinafter as "SR17" and the alternan produced with full length alternansucrase is also abbreviated hereinafter as "SR16".

Alternans were dissolved overnight at 50° C. at concentrations of from 7% to 15% (w/v). The samples were filtered through a 5 µm PTFE Whatman Puradisc™ 13 mm filter syringe, and the dissolved alternan fraction was analyzed by means of GPC-MALLS. The dissolved alternan fraction at different concentrations is shown in table 1.

TABLE 1

Dissolved alternan fraction at different concentrations, determined by GPC-MALLS

| Concentration (w/v) | alternan produced from truncated alternansucrase (SR17) % dissolved | alternan produced from full length alternansucrase (SR16) (comparative ex.) % dissolved |
|---|---|---|
| 7% | 91.2% | 87.1% |
| 8% | 89.3% | 86.8% |
| 9% | 87.4% | 80.9% |
| 10% | 88.0% | 83.2% |
| 11% | 95.2% | 66.1% |
| 12% | 90.8% | 71.1% |
| 13% | 67.8% | 45.0% |
| 15% | 66.5% | 59.5% |

Example 5

Viscosity of Alternan

Alternans were produced with truncated alternansucrase and with full length alternansucrase (comparative example) as described in 1.5. The alternan produced with truncated alternansucrase is also abbreviated hereinafter as "SR17" and the alternan produced with full length alternansucrase is also abbreviated hereinafter as "SR16".

Alternans were dissolved overnight at 50° C. at concentrations of from 7% to 15% (w/v). The samples were filtered through a 5 µm PTFE Whatman Puradisc™ 13 mm filter syringe. The viscosity was determined as described in the methods. The viscosity is shown in table 2.

TABLE 2

Viscosity of alternan at different concentrations.

| Concentration (w/v) | alternan produced from truncated alternansucrase (SR17) Viscosity (mPa*S) | Standard dev. | alternan produced from full length alternansucrase (SR16) (comparative ex.) Viscosity (mPa*S) | Standard dev. |
|---|---|---|---|---|
| 8% | 9.4 | 1.9 | 17.7 | 1.8 |
| 9% | 13.9 | 2.1 | 39.3 | 2.0 |
| 10% | 29.9 | 3.2 | 120.6 | 3.8 |
| 11% | 60.7 | 2.5 | 367.9 | 11.1 |
| 12% | 240.3 | 9.3 | 927.2 | 7.4 |
| 13% | 702.0 | 14.1 | 1722.8 | 25.5 |
| 15% | 3605.7 | 94.5 | 6204.1 | 60.3 |

Example 6

Proof of Differences in Acceptor Reactions Concerning the Development of Alternan Relative to Alternan Oligosaccharides 6.1 Material and Methods:
Protein Expression:

Vector pAI-B-AlSu contains the full-length coding sequence of alternansucrase derived from *Leuconostoc mesenteroides* strain NRRL B-1355 lacking the N-terminal 39 amino acids from the signal peptide (protein comprising amino acids 40-2057 of SEQ ID NO 2), fused to an octapeptide strep-tag at the C-terminal end. The strep-tag is linked to the protein through a dipeptide linker Expression of alternansucrase is under the transcriptional control of the tetA promoter/operator and repressor. The tetA promoter is tightly regulated by the tet repressor which is encoded on the same plasmid and is constitutively expressed from the β-lactamase promoter. In this way, expression of alternansucrase is stringently repressed until efficient chemical induction by tetracycline or anhydrotetracycline, AHT.

For fermentation, vector pAI-B-AlSu was transformed in E. coli K12 DH5α and bacterial cells harbouring the vector were selectively grown for 28 h at 37° C. to an OD600 of 50 in mineral medium (Horn et al., 1996) supplemented with ampicillin (100 μg/ml). Expression of the alternansucrase was induced by the addition of anhydrotetracyclin (0.2 mg/l) and further cultivation for 22 h at 25° C. to an OD600 of 140. For purification of the enzyme, the bacterial cells were harvested by centrifugation (20000 rpm; 20 min) and solubilized in resuspension buffer (100 mM sodium acetate, pH 5.3).

The cells were disrupted using a high pressure homogenizer (two cycles, 1200 bar). Bacterial nucleic acid was degraded by DNase/RNase (3 mg/l) treatment and the resulting extract was centrifuged (9400 g for 15 min at 4° C.) to harvest the insoluble cell matter. The supernatant was filtrated through a 0.22 μm Sterivex-GV (Millipore) and is stored at −20° C. until use.

Vector pAN94 contains the C-terminally truncated version of the alternansucrase, lacking the C-terminal 742 amino acids (protein comprising amino acids 40-1315 of SEQ ID NO 2). The vector pAN94 derives from pAI-B vector and the expression occurs also under the transcriptional control of the tetA promoter/operator and repressor. For expression, vector pAN94 was transformed in E. coli K12 DH5α and bacterial cells harbouring the vector were selectively grown for 4 h at 37° C. to an OD600 of 0.73 in 400 ml YT medium (Sambroock, Fritsch, Maniatis) supplemented with ampicillin (100 μg/ml). Expression of truncated alternansucrase was induced by the addition of anhydrotetracyclin (0.2 mg/l). Also 5 mM IPTG and 1% Glucose were added. The further cultivation occurs for 25 h at 22° C. to an OD600 of 1.9. For purification of the enzyme, the bacterial cells were harvested by centrifugation (4000 rpm; 20 min) and solubilized in resuspension buffer (50 mM sodium acetate, pH 5.3, 2.5 mM DTT). The cells were disrupted using a French Press (3 cycles). The resulting extract was centrifuged (33000 g für 15 min at 4° C.) to harvest the insoluble cell matter. The supernatant was filtrated through a 0.22 μm Sterivex-GV (Millipore) and was stored at −20° C. until use.

Activity Assay:

Activity was assayed using a NADP-coupled photometric assay measuring the release of fructose. For alternansucrase variants, one unit is defined as the amount of enzyme that catalyzes the formation of 1 μmol fructose in one minute at 37° C. in 75 mM sodium acetate, pH 5.2 and 200 g/l Sucrose.

Acceptor Reactions

Acceptor reactions were performed in a total volume of 20 ml with 0.22 units/ml, at 20° C. in sodium acetate buffer 75 mM, pH 5.2 and 200 g/l Sucrose. As acceptor 80, 100, 120 g/l maltose monohydrate or isomaltulose was added respectively. Sucrose conversion was monitored after 2.5 h, 18.5 h, 26 h, 42.5 h, and 48 h by using a NADP-coupled photometric assay measuring the release of fructose and the remained sucrose, and reactions were stopped by 10 min of incubation at 95° C.

Glucan Analysis

After complete sucrose depletion (48 h) the acceptor reaction is analysed by SEC-MALLS-RI on WATERS Styragel columns (Styragel 7, Styragel 6E, Styragel 2, and Styragel guard). As Eluent 90 mM sodium nitrate in Dimethylsulfoxide (DMSO) at a flow rate of 0.5 ml/min was used. The columns were heated to 60° C. The samples were prepared as follows: 10 μl of sample were added to 990 μl DMSO. The diluted sample was incubated at room temperature while rotating overnight. After it the diluted sample was incubated for 2 hours at 95° C. while mixing at 1400 rpm in a thermomixer. After cooling the sample was centrifuged for 5 min at 13000 rpm and filtrated through 5 μm PTFE syringe filter (Whatman). 50 μl of the filtrated sample were injected. If possible the refractive index (RI) peak areas of alternan and acceptor products were determined and compared. In case of maltose the amount of alternan is too low and therefore only a comparison of the much more sensitive light scattering signals was possible.

6.2 Results

The amount of alternan produced by the full-length variant of alternansucrase is higher compared to the amount produced by the truncated alternansucrase.

Figure 3:
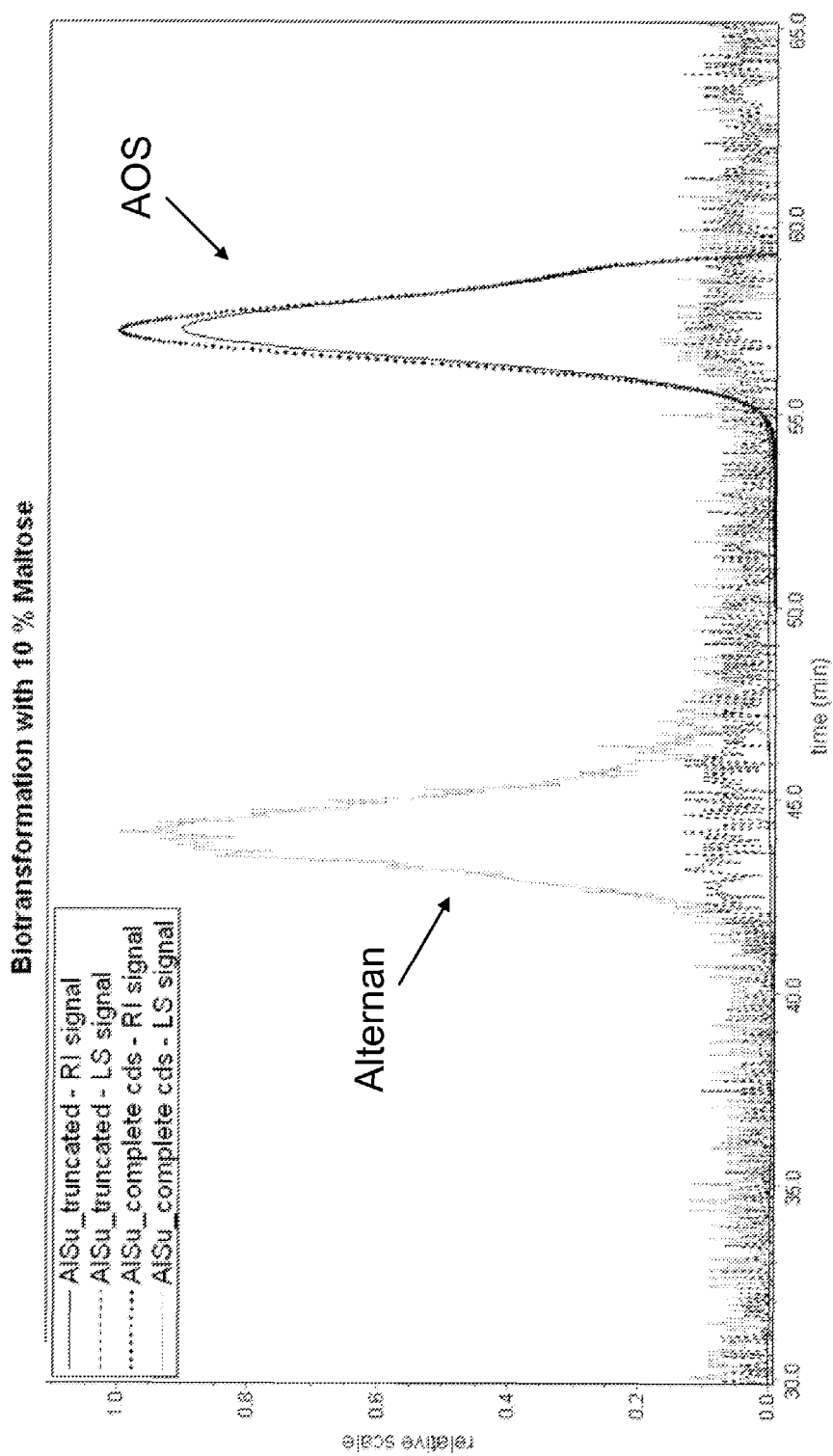
FIG. 3: Maltose elograms of SEC-MALLS-RI.

In the case of maltose the elugrams of SEC-MALLS-RI are shown in FIG. 3. FIG. 3 shows elugrams (RI and Light scattering—LS—signals) of samples coming from acceptor reactions with 10% maltose (AlSu_truncated=truncated alternansucrase, AlSu_complete=full length alternansucrase, AOS=alternan oligosaccharides).

Because of the high acceptor strength of maltose, there are no RI signals caused of alternan. But the difference in light scattering signals shows the different amounts of alternan. Using the truncated alternansucrase, the resulting light scattering signal is much lower compared to the use of the full-length variant of alternansucrase in the acceptor reaction.

In the case of isomaltulose both elugrams and RI peak areas are shown in FIG. 4 and table 3 respectively. FIG. 4 shows elugrams (RI and Light scattering—LS— signals) of samples coming from acceptor reactions with 10% isomaltulose (AlSu_truncated=truncated alternansucrase, AlSu_complete=full length alternansucrase, AOS=alternan oligosaccharides).

Because of the lower acceptor strength compared to maltose, measurable amounts of alternan can be detected. Using the truncated alternansucrase, the resulting RI peak area and light scattering signal is much lower compared to the use of the full-length variant of alternansucrase in the acceptor reaction.

TABLE 3

RI peak areas determined by SEC-MALLS-RI analysis.

| alternansucrase enzyme | Isomaltulose concentration | area μRIU*min alternan | area μRIU*min oligosaccharide | area μRIU*min total | rel. area (%) alternan |
|---|---|---|---|---|---|
| truncated | 8% | 0.10 | 31.93 | 32.03 | 0.30 |
| truncated | 10% | 0.04 | 37.25 | 37.29 | 0.11 |
| truncated | 12% | 0.03 | 43.59 | 43.61 | 0.06 |
| full-length | 8% | 0.35 | 31.52 | 31.88 | 1.10 |
| full-length | 10% | 0.22 | 33.37 | 33.60 | 0.67 |
| full-length | 12% | 0.24 | 38.80 | 39.04 | 0.60 |

The relative area of alternan was calculated by dividing area of alternan by the total area.

We claim:

1. An isolated nucleic acid molecule consisting of:
    a) a sequence from nucleotide position 118 up to and including nucleotide position 3945 of the nucleic acid sequence shown in SEQ ID NO 1 or SEQ ID NO 3;
    b) a sequence which codes for a protein whose amino acid sequence has at least 95% identity with the sequence from amino acid position 40 up to and including amino acid position 1315 of SEQ ID NO 2, wherein said protein has the same number of amino acids as the protein with the sequence from the amino acid at position 40 up to and including to the amino acid at position 1315 of SEQ ID NO 2;
    c) a sequence that has at least 95% identity with the sequence of a), where said sequence has the same number of nucleotides as the sequence of a), and encodes the protein of b);
    d) a sequence that, as the result of the degeneracy of the genetic code, deviates from the sequence of the nucleic acid molecules of a), b), or c); or
    e) a sequence that is complementary to the full-length sequence of one of the nucleic acid molecules of a), b), c), or d), where the complementary sequence has the same number of nucleotides as the nucleic acid molecules of a), b), c), or d);
wherein said nucleic acid molecule codes for a truncated protein lacking the C-terminal domain and having enzymatic activity of an alternan sucrase, and wherein said nucleic acid molecule has attached to its 3' end a nucleic acid triplet of TAA, TAG or TGA.

2. The nucleic acid molecule of claim 1, wherein said nucleic acid molecule has attached to its 5' end a nucleic acid triplet ATG.

3. A vector comprising the nucleic acid molecule of claim 1.

4. The vector of claim 3, wherein said vector is a plasmid.

5. An isolated host cell comprising the nucleic acid molecule of claim 1.

6. The host cell of claim 5, wherein said cell is a microorganism.

7. The host cell of claim 6, wherein said cell is an *E. coli* cell.

8. The host cell of claim 5, wherein said cell is a plant cell.

9. A plant comprising the plant cell of claim 8.

10. The plant of claim 9, wherein said plant is a sugar- or starch-storing plant.

11. The plant of claim 9, wherein said plant is potato, maize, sugar beet, sugar sorghum, or sugarcane.

12. A propagation material of a plant which comprises the plant cell of claim 8.

13. A harvestable plant part obtained from a plant which comprises the plant cell of claim 8.

14. A method of generating a plant, said method comprising:
    a) introducing, into a plant cell, the nucleic acid molecule of claim 1,
    b) regenerating a plant from the plant cell obtained in step a), and
    c) optionally, generating further plants with the aid of the plants obtained in step b).

15. A method of producing a protein having the enzymatic activity of an alternan sucrase, said method comprising:
    1) transforming a host cell with
        a) a nucleic acid molecule whose sequence codes for a protein consisting of
            i) an amino acid sequence which starts in the region from amino acid position 1 to amino acid position 350 of SEQ ID NO 2 and which ends at amino acid position 1315 of SEQ ID NO 2; or
            ii) an amino acid sequence which has at least 95% identity with an amino acid sequence from i),
        wherein the nucleic acid molecule is obtainable from a nucleic acid molecule with a sequence shown in SEQ ID NO 1 or 3, or
        b) a vector or plasmid comprising the nucleic acid molecule of a),
    2) culturing the host cell in culture medium, and
    3) isolating the protein from the cultured cell and/or the culture medium.

16. A method of producing a protein having enzymatic activity of an alternan sucrase, said method comprising:
    1) transforming a plant cell with
        a) a nucleic acid molecule whose sequence codes for a protein consisting of
            i) an amino acid sequence which starts in the region from amino acid position 1 to amino acid position 350 of SEQ ID NO 2 and which ends at amino acid 1315 of SEQ ID NO 2; or
            ii) an amino acid sequence which has at least 95% identity with an amino acid sequence from i),
        where the nucleic acid molecule is obtainable from a nucleic acid molecule with a sequence shown in SEQ ID NO 1 or 3, or
        b) a vector or plasmid comprising a nucleic acid molecule of a),
    2) regenerating a plant from the plant cell obtained in step 1),
    3) expressing the protein in the plant and subsequently extracting and isolating the protein.

17. An isolated host cell comprising the nucleic acid molecule of claim 2.

18. A host cell comprising the vector of claim 3.

19. A host cell comprising the plasmid of claim 4.

20. A method of generating a plant, said method comprising:
   a) introducing, into a plant cell, a vector of claim 3,
   b) regenerating a plant from the plant cell obtained in step a), and
   c) optionally, generating further plants with the aid of the plant obtained in step b).

21. A method of producing alternan, said method comprising the steps of extracting and isolating the alternan from the propagation material of claim 12.

22. A method of producing alternan, said method comprising the steps of extracting and isolating the alternan from the harvestable plant part of claim 13.

23. A host cell comprising a heterologous nucleic acid molecule consisting of:
   a) a sequence from nucleotide position 118 up to and including nucleotide position 3945 of the nucleic acid sequence shown in SEQ ID NO 1 or SEQ ID NO 3;
   b) a sequence which codes for a protein whose amino acid sequence has at least 95% identity with the sequence from amino acid position 40 up to and including amino acid position 1315 of SEQ ID NO 2, wherein said protein has the same number of amino acids as the protein with the sequence from the amino acid at position 40 up to and including to the amino acid at position 1315 of SEQ ID NO 2;
   c) a sequence that has at least 95% identity with the sequence of a), where said sequence has the same number of nucleotides as the sequence of a), and encodes the protein of b);
   d) a sequence that, as the result of the degeneracy of the genetic code, deviates from the sequence of the nucleic acid molecules of a), b), or c); or
   e) a sequence that is complementary to the full-length sequence of one of the nucleic acid molecules of a), b), c), or d), where the complementary sequence has the same number of nucleotides as the nucleic acid molecules of a), b), c), or d);
   wherein said nucleic acid molecule codes for a truncated protein lacking the C-terminal domain and having enzymatic activity of an alternan sucrase.

24. The method of claim 15, wherein the protein having the enzymatic activity of an alternan sucrase produces a modified alternan having decreased molecular weight, increased solubility, decreased viscosity, or combinations thereof when compared to alternan produced by full length alternan sucrase.

25. The method of claim 15, wherein the protein having the enzymatic activity of an alternan sucrase produces an alternan having a molecular weight in the range of 12,000,000 to 30,000,000.

26. The method of claim 25, wherein the alternan has a molecular weight of 21,200,000 grams/mol.

27. The isolated nucleic acid of claim 1, wherein the nucleic acid sequence is operable linked to a promoter.

\* \* \* \* \*

SEQUENCE LISTING

<160> NUMBER OF SEQ IDS NOS: 25

<210> SEQ ID NO 1
<211> LENGTH: 6174
<212> TYPE: DNA
<213> ORGANISM: Leuconostoc mesenteroides
<220> FEATURE:
<221> NAME/KEY: CDS
<222> LOCATION: (1)..(6171)

<400> SEQUENCE: 1

```
atg aaa caa caa gaa aca gtt acc cgt aaa aaa ctt tat aaa tcc ggt      48
Met Lys Gln Gln Glu Thr Val Thr Arg Lys Lys Leu Tyr Lys Ser Gly
 1               5                  10                  15 aag gtt tgg gtt gca gca gct act gca ttt gcg gta ttg ggg gtt tca      96
Lys Val Trp Val Ala Ala Ala Thr Ala Phe Ala Val Leu Gly Val Ser
             20                  25                  30 act gta aca aca gtc cat gcg gat aca aat tcg aat gtc gct gtt aag     144
Thr Val Thr Thr Val His Ala Asp Thr Asn Ser Asn Val Ala Val Lys
         35                  40                  45 caa ata aat aat aca gga acc aat gat tct ggc gaa aaa aag gta ccg     192
Gln Ile Asn Asn Thr Gly Thr Asn Asp Ser Gly Glu Lys Lys Val Pro
     50                  55                  60 gtt cca tca act aat aat gat agt ttg aag caa gga aca gat ggt ttt     240
Val Pro Ser Thr Asn Asn Asp Ser Leu Lys Gln Gly Thr Asp Gly Phe
 65                  70                  75                  80 tgg tat gat tca gac ggc aat cgt gtc gat cag aag acc aat cag att     288
Trp Tyr Asp Ser Asp Gly Asn Arg Val Asp Gln Lys Thr Asn Gln Ile
                 85                  90                  95 ctg ctt act gcg gaa caa ctt aaa aaa aat aac gaa aaa aat tta tca     336
Leu Leu Thr Ala Glu Gln Leu Lys Lys Asn Asn Glu Lys Asn Leu Ser
            100                 105                 110 gta atc agt gat gat aca tca aaa aaa gat gat gaa aat att tct aag     384
Val Ile Ser Asp Asp Thr Ser Lys Lys Asp Asp Glu Asn Ile Ser Lys
        115                 120                 125 cag acc aaa att gct aat caa caa aca gta gat act gct aaa ggc ctg     432
Gln Thr Lys Ile Ala Asn Gln Gln Thr Val Asp Thr Ala Lys Gly Leu
    130                 135                 140 act acc agt aat tta tct gat ccc atc act ggg ggt cac tat gaa aat     480
Thr Thr Ser Asn Leu Ser Asp Pro Ile Thr Gly Gly His Tyr Glu Asn
145                 150                 155                 160 cac aat ggc tac ttt gtt tat ata gat gct tca gga aaa caa gta aca     528
His Asn Gly Tyr Phe Val Tyr Ile Asp Ala Ser Gly Lys Gln Val Thr
                165                 170                 175 ggt ttg caa aat att gat ggt aat tta caa tat ttt gat gac aat gga     576
Gly Leu Gln Asn Ile Asp Gly Asn Leu Gln Tyr Phe Asp Asp Asn Gly
            180                 185                 190 tat caa gtc aag gga tcc ttc cga gat gtc aac ggc aag cat atc tat     624
Tyr Gln Val Lys Gly Ser Phe Arg Asp Val Asn Gly Lys His Ile Tyr
        195                 200                 205 ttt gat tca gta aca ggg aaa gct agt tca aat gtt gat att gtt aac     672
Phe Asp Ser Val Thr Gly Lys Ala Ser Ser Asn Val Asp Ile Val Asn
    210                 215                 220 ggt aaa gct caa gga tat gat gcg caa ggc aac caa tta aag aaa agt     720
Gly Lys Ala Gln Gly Tyr Asp Ala Gln Gly Asn Gln Leu Lys Lys Ser
225                 230                 235                 240 tat gtc gcc gat agt tct ggg caa act tac tat ttt gat ggt aat ggc     768
Tyr Val Ala Asp Ser Ser Gly Gln Thr Tyr Tyr Phe Asp Gly Asn Gly
                245                 250                 255 caa ccg tta atc ggc ttg caa aca att gat ggg aac cta caa tat ttt     816
Gln Pro Leu Ile Gly Leu Gln Thr Ile Asp Gly Asn Leu Gln Tyr Phe
```

```
                        260                   265                   270
aac caa caa ggg gtt caa ata aag ggt ggt ttc caa gat gtt aac aat          864
Asn Gln Gln Gly Val Gln Ile Lys Gly Gly Phe Gln Asp Val Asn Asn
            275                   280                   285 aaa cgt att tat ttt gca cca aac aca ggt aat gcc gtt gcc aat act          912
Lys Arg Ile Tyr Phe Ala Pro Asn Thr Gly Asn Ala Val Ala Asn Thr
290                   295                   300 gaa ata att aac ggt aaa tta cag ggg cgt gac gca aat ggt aac cag          960
Glu Ile Ile Asn Gly Lys Leu Gln Gly Arg Asp Ala Asn Gly Asn Gln
305                   310                   315                   320 gta aag aat gca ttt agt aaa gat gtt gca gga aat aca ttt tat ttt         1008
Val Lys Asn Ala Phe Ser Lys Asp Val Ala Gly Asn Thr Phe Tyr Phe
            325                   330                   335 gac gca aac ggt gtg atg tta aca ggg ttg caa act att tca gga aag         1056
Asp Ala Asn Gly Val Met Leu Thr Gly Leu Gln Thr Ile Ser Gly Lys
            340                   345                   350 aca tat tat ctt gat gaa caa gga cac ctg aga aaa aat tac gcg gga         1104
Thr Tyr Tyr Leu Asp Glu Gln Gly His Leu Arg Lys Asn Tyr Ala Gly
            355                   360                   365 aca ttc aat aat cag ttt atg tac ttc gat gct gat aca ggt gcg ggt         1152
Thr Phe Asn Asn Gln Phe Met Tyr Phe Asp Ala Asp Thr Gly Ala Gly
370                   375                   380 aaa aca gcg att gaa tat caa ttt gat caa gga ttg gta tca caa agt         1200
Lys Thr Ala Ile Glu Tyr Gln Phe Asp Gln Gly Leu Val Ser Gln Ser
385                   390                   395                   400 aat gaa aat act cct cac aat gcc gca aag tct tat gat aaa agt agt         1248
Asn Glu Asn Thr Pro His Asn Ala Ala Lys Ser Tyr Asp Lys Ser Ser
            405                   410                   415 ttt gaa aat gtt gat ggt tac tta aca gca gat aca tgg tat cgt cca         1296
Phe Glu Asn Val Asp Gly Tyr Leu Thr Ala Asp Thr Trp Tyr Arg Pro
            420                   425                   430 acc gat att tta aaa aat gga gat act tgg acg gca tct acc gaa act         1344
Thr Asp Ile Leu Lys Asn Gly Asp Thr Trp Thr Ala Ser Thr Glu Thr
            435                   440                   445 gat atg cgt ccg ctt tta atg aca tgg tgg cct gac aaa caa aca caa         1392
Asp Met Arg Pro Leu Leu Met Thr Trp Trp Pro Asp Lys Gln Thr Gln
450                   455                   460 gca aat tac ttg aat ttt atg tct agt aaa gga ctt ggt ata acg acc         1440
Ala Asn Tyr Leu Asn Phe Met Ser Ser Lys Gly Leu Gly Ile Thr Thr
465                   470                   475                   480 act tat aca gca gct acg tca caa aaa aca cta aat gac gca gcc ttt         1488
Thr Tyr Thr Ala Ala Thr Ser Gln Lys Thr Leu Asn Asp Ala Ala Phe
            485                   490                   495 gtt att caa aca gca att gaa caa caa ata tct ttg aaa aaa agt act         1536
Val Ile Gln Thr Ala Ile Glu Gln Gln Ile Ser Leu Lys Lys Ser Thr
            500                   505                   510 gag tgg tta cgt gat gca att gat agt ttt gtg aag acg caa gct aat         1584
Glu Trp Leu Arg Asp Ala Ile Asp Ser Phe Val Lys Thr Gln Ala Asn
            515                   520                   525 tgg aat aag caa aca gaa gat gaa gct ttc gat ggt ttg cag tgg ctt         1632
Trp Asn Lys Gln Thr Glu Asp Glu Ala Phe Asp Gly Leu Gln Trp Leu
530                   535                   540 caa ggg gga ttc cta gct tat caa gat gat tca cat cgg acg ccg aat         1680
Gln Gly Gly Phe Leu Ala Tyr Gln Asp Asp Ser His Arg Thr Pro Asn
545                   550                   555                   560 act gat tca gga aat aac aga aaa cta gga cgt caa cca att aat atc         1728
Thr Asp Ser Gly Asn Asn Arg Lys Leu Gly Arg Gln Pro Ile Asn Ile
            565                   570                   575 gat ggt tcg aaa gat aca act gat ggt aaa ggc tct gaa ttc tta tta         1776
```

-continued

| | | |
|---|---|---|
| Asp Gly Ser Lys Asp Thr Thr Asp Gly Lys Gly Ser Glu Phe Leu Leu<br>580                   585                   590 | | |
| gct aac gat att gac aac tca aat ccg att gtt caa gct gag caa tta<br>Ala Asn Asp Ile Asp Asn Ser Asn Pro Ile Val Gln Ala Glu Gln Leu<br>      595                   600                   605 | | 1824 |
| aac tgg cta cac tat tta atg aat ttt ggt agt att aca ggt aat aat<br>Asn Trp Leu His Tyr Leu Met Asn Phe Gly Ser Ile Thr Gly Asn Asn<br>610                   615                   620 | | 1872 |
| gac aat gcg aat ttt gat ggc att cgt gta gat gct gtt gat aat gtt<br>Asp Asn Ala Asn Phe Asp Gly Ile Arg Val Asp Ala Val Asp Asn Val<br>625                   630                   635                   640 | | 1920 |
| gat gct gat tta cta aaa ata gct ggc gat tat ttt aaa gct cta tat<br>Asp Ala Asp Leu Leu Lys Ile Ala Gly Asp Tyr Phe Lys Ala Leu Tyr<br>            645                   650                   655 | | 1968 |
| ggt aca gat aaa agc gac gcc aat gcc aat aag cat ttg tct att tta<br>Gly Thr Asp Lys Ser Asp Ala Asn Ala Asn Lys His Leu Ser Ile Leu<br>            660                   665                   670 | | 2016 |
| gaa gac tgg aac ggt aaa gat cct cag tat gtt aat caa cag ggc aat<br>Glu Asp Trp Asn Gly Lys Asp Pro Gln Tyr Val Asn Gln Gln Gly Asn<br>            675                   680                   685 | | 2064 |
| gcg caa tta aca atg gat tac aca gtt act tca cag ttt ggc aat tct<br>Ala Gln Leu Thr Met Asp Tyr Thr Val Thr Ser Gln Phe Gly Asn Ser<br>690                   695                   700 | | 2112 |
| cta aca cat ggc gcc aac aac agg agt aac atg tgg tat ttc tta gat<br>Leu Thr His Gly Ala Asn Asn Arg Ser Asn Met Trp Tyr Phe Leu Asp<br>705                   710                   715                   720 | | 2160 |
| act ggc tat tat ctt aat gga gat ctt aat aag aag ata gta gat aag<br>Thr Gly Tyr Tyr Leu Asn Gly Asp Leu Asn Lys Lys Ile Val Asp Lys<br>            725                   730                   735 | | 2208 |
| aac cgt cca aat tct ggc act ttg gtt aac aga att gct aat tca ggt<br>Asn Arg Pro Asn Ser Gly Thr Leu Val Asn Arg Ile Ala Asn Ser Gly<br>            740                   745                   750 | | 2256 |
| gat aca aaa gtt att cca aat tat agt ttt gtt aga gca cat gat tac<br>Asp Thr Lys Val Ile Pro Asn Tyr Ser Phe Val Arg Ala His Asp Tyr<br>            755                   760                   765 | | 2304 |
| gat gct caa gat cca att aga aaa gcc atg att gat cat ggt att att<br>Asp Ala Gln Asp Pro Ile Arg Lys Ala Met Ile Asp His Gly Ile Ile<br>770                   775                   780 | | 2352 |
| aaa aac atg cag gat act ttc act ttt gac caa ctg gct cag gga atg<br>Lys Asn Met Gln Asp Thr Phe Thr Phe Asp Gln Leu Ala Gln Gly Met<br>785                   790                   795                   800 | | 2400 |
| gaa ttc tac tat aaa gat caa gag aat ccg tct ggt ttc aaa aag tat<br>Glu Phe Tyr Tyr Lys Asp Gln Glu Asn Pro Ser Gly Phe Lys Lys Tyr<br>            805                   810                   815 | | 2448 |
| aac gat tat aac tta cct agt gct tat gca atg ttg ttg act aat aag<br>Asn Asp Tyr Asn Leu Pro Ser Ala Tyr Ala Met Leu Leu Thr Asn Lys<br>            820                   825                   830 | | 2496 |
| gat act gta cct cgt gtc tat tat gga gat atg tac ctc gaa ggc ggg<br>Asp Thr Val Pro Arg Val Tyr Tyr Gly Asp Met Tyr Leu Glu Gly Gly<br>            835                   840                   845 | | 2544 |
| caa tat atg gaa aaa ggg acg att tac aat cct gtc att tca gcg ttg<br>Gln Tyr Met Glu Lys Gly Thr Ile Tyr Asn Pro Val Ile Ser Ala Leu<br>850                   855                   860 | | 2592 |
| ctc aaa gct aga ata aaa tat gtt tct ggt ggg caa aca atg gct acc<br>Leu Lys Ala Arg Ile Lys Tyr Val Ser Gly Gly Gln Thr Met Ala Thr<br>865                   870                   875                   880 | | 2640 |
| gat agt tct gga aaa gac ctt aaa gat ggc gaa act gat ttg tta aca<br>Asp Ser Ser Gly Lys Asp Leu Lys Asp Gly Glu Thr Asp Leu Leu Thr<br>            885                   890                   895 | | 2688 |

-continued

| | | |
|---|---|---|
| agt gtt cga ttt ggt aaa gga att atg aca tca gat caa acc aca aca<br>Ser Val Arg Phe Gly Lys Gly Ile Met Thr Ser Asp Gln Thr Thr Thr<br>                      900                        905                    910 | 2736 |
| caa gac aat agc caa gat tat aaa aat caa ggc atc ggt gtc att gtt<br>Gln Asp Asn Ser Gln Asp Tyr Lys Asn Gln Gly Ile Gly Val Ile Val<br>              915                      920                  925 | 2784 |
| ggt aat aac cct gac ctt aag ttg aac aat gat aag acc att acc ttg<br>Gly Asn Asn Pro Asp Leu Lys Leu Asn Asn Asp Lys Thr Ile Thr Leu<br>930                        935                      940 | 2832 |
| cat atg gga aag gcg cat aag aat caa ctt tac cgt gcc tta gta tta<br>His Met Gly Lys Ala His Lys Asn Gln Leu Tyr Arg Ala Leu Val Leu<br>945                        950                      955                  960 | 2880 |
| tca aat gac tca gga att gat gtt tat gat agt gat gat aaa gca cca<br>Ser Asn Asp Ser Gly Ile Asp Val Tyr Asp Ser Asp Asp Lys Ala Pro<br>                        965                      970                  975 | 2928 |
| act ttg aga aca aat gac aac ggt gac ttg att ttc cat aag aca aat<br>Thr Leu Arg Thr Asn Asp Asn Gly Asp Leu Ile Phe His Lys Thr Asn<br>              980                      985                      990 | 2976 |
| acg ttt gtg aag caa gat gga act att ata aat tac gaa atg aag gga<br>Thr Phe Val Lys Gln Asp Gly Thr Ile Ile Asn Tyr Glu Met Lys Gly<br>            995                     1000                  1005 | 3024 |
| tca tta aat gct tta att tca ggt tat tta ggt gtc tgg gtg cca<br>Ser Leu Asn Ala Leu Ile Ser Gly Tyr Leu Gly Val Trp Val Pro<br>1010                       1015                    1020 | 3069 |
| gtt gga gct agt gat tca caa gat gct cgt aca gtg gca act gag<br>Val Gly Ala Ser Asp Ser Gln Asp Ala Arg Thr Val Ala Thr Glu<br>            1025                    1030                    1035 | 3114 |
| tca tca tca agt aat gat ggt tct gta ttc cat tca aat gct gca<br>Ser Ser Ser Ser Asn Asp Gly Ser Val Phe His Ser Asn Ala Ala<br>1040                       1045                    1050 | 3159 |
| tta gat tct aat gtt ata tat gaa ggc ttt tca aac ttt caa gcg<br>Leu Asp Ser Asn Val Ile Tyr Glu Gly Phe Ser Asn Phe Gln Ala<br>            1055                    1060                    1065 | 3204 |
| atg ccg act tct cct gag caa agt aca aat gtt gtt att gca aca<br>Met Pro Thr Ser Pro Glu Gln Ser Thr Asn Val Val Ile Ala Thr<br>1070                       1075                    1080 | 3249 |
| aag gct aac tta ttt aaa gaa tta ggt att act agt ttt gag tta<br>Lys Ala Asn Leu Phe Lys Glu Leu Gly Ile Thr Ser Phe Glu Leu<br>            1085                    1090                    1095 | 3294 |
| gca cct caa tat agg tct agt ggt gac act aat tac ggt ggc atg<br>Ala Pro Gln Tyr Arg Ser Ser Gly Asp Thr Asn Tyr Gly Gly Met<br>1100                       1105                    1110 | 3339 |
| tca ttc tta gat tct ttc tta aat aat ggt tat gca ttt acc gat<br>Ser Phe Leu Asp Ser Phe Leu Asn Asn Gly Tyr Ala Phe Thr Asp<br>            1115                    1120                    1125 | 3384 |
| aga tat gat tta ggc ttt aac aaa gca gac ggg aat cct aac cca<br>Arg Tyr Asp Leu Gly Phe Asn Lys Ala Asp Gly Asn Pro Asn Pro<br>1130                       1135                    1140 | 3429 |
| aca aag tat gga aca gat caa gat tta cgt aat gca ata gag gca<br>Thr Lys Tyr Gly Thr Asp Gln Asp Leu Arg Asn Ala Ile Glu Ala<br>            1145                    1150                    1155 | 3474 |
| tta cac aaa aac ggc atg cag gct ata gct gat tgg gtt cct gac<br>Leu His Lys Asn Gly Met Gln Ala Ile Ala Asp Trp Val Pro Asp<br>1160                       1165                    1170 | 3519 |
| caa ata tat gct tta cca gga aag gaa gtt gtt acc gct act aga<br>Gln Ile Tyr Ala Leu Pro Gly Lys Glu Val Val Thr Ala Thr Arg<br>            1175                    1180                    1185 | 3564 |
| gta gac gaa cgg gga aat caa cta aaa gac aca gat ttt gtc aac<br>Val Asp Glu Arg Gly Asn Gln Leu Lys Asp Thr Asp Phe Val Asn<br>1190                       1195                    1200 | 3609 |

```
tta ctc tat gtt gct aat act aaa agt agt ggt gtg gat tat cag      3654
Leu Leu Tyr Val Ala Asn Thr Lys Ser Ser Gly Val Asp Tyr Gln
    1205                1210                1215 gca aag tat ggc ggc gaa ttt tta gat aaa tta aga gaa gag tac      3699
Ala Lys Tyr Gly Gly Glu Phe Leu Asp Lys Leu Arg Glu Glu Tyr
    1220                1225                1230 cca tcg tta ttc aaa cag aac caa gta tcg aca ggt cag cca att      3744
Pro Ser Leu Phe Lys Gln Asn Gln Val Ser Thr Gly Gln Pro Ile
    1235                1240                1245 gat gct tct aca aaa att aag caa tgg tca gct aaa tat atg aat      3789
Asp Ala Ser Thr Lys Ile Lys Gln Trp Ser Ala Lys Tyr Met Asn
    1250                1255                1260 ggg acc aat att tta cat cga ggt gct tat tat gtt ttg aaa gac      3834
Gly Thr Asn Ile Leu His Arg Gly Ala Tyr Tyr Val Leu Lys Asp
    1265                1270                1275 tgg gct act aac cag tat ttt aac att gca aaa acg aat gaa gta      3879
Trp Ala Thr Asn Gln Tyr Phe Asn Ile Ala Lys Thr Asn Glu Val
    1280                1285                1290 ttt ttg cca cta cag ttg cag aat aaa gat gcg caa act ggt ttc      3924
Phe Leu Pro Leu Gln Leu Gln Asn Lys Asp Ala Gln Thr Gly Phe
    1295                1300                1305 att agt gat gcc tcc ggt gta aaa tat tac tca att agt ggt tat      3969
Ile Ser Asp Ala Ser Gly Val Lys Tyr Tyr Ser Ile Ser Gly Tyr
    1310                1315                1320 caa gca aaa gat act ttt att gaa gat ggt aat ggg aat tgg tat      4014
Gln Ala Lys Asp Thr Phe Ile Glu Asp Gly Asn Gly Asn Trp Tyr
    1325                1330                1335 tac ttt gat aaa gat ggt tac atg gtg cgt tcg cag caa gga gaa      4059
Tyr Phe Asp Lys Asp Gly Tyr Met Val Arg Ser Gln Gln Gly Glu
    1340                1345                1350 aat cct ata aga aca gtc gaa act agt gtc aac aca cga aac ggt      4104
Asn Pro Ile Arg Thr Val Glu Thr Ser Val Asn Thr Arg Asn Gly
    1355                1360                1365 aat tat tac ttt atg cca aat ggt gtc gag ttg cgc aaa ggc ttt      4149
Asn Tyr Tyr Phe Met Pro Asn Gly Val Glu Leu Arg Lys Gly Phe
    1370                1375                1380 gga acg gat aat agt ggt aat gtc tat tat ttt gat gat caa ggt      4194
Gly Thr Asp Asn Ser Gly Asn Val Tyr Tyr Phe Asp Asp Gln Gly
    1385                1390                1395 aag atg gtg aga gat aaa tac att aac gat gat gct aat aat ttt      4239
Lys Met Val Arg Asp Lys Tyr Ile Asn Asp Asp Ala Asn Asn Phe
    1400                1405                1410 tat cac tta aat gtt gat ggg act atg tct cga gga cta ttt aaa      4284
Tyr His Leu Asn Val Asp Gly Thr Met Ser Arg Gly Leu Phe Lys
    1415                1420                1425 ttt gat tct gat act cta cag tat ttt gct agt aat ggt gtc caa      4329
Phe Asp Ser Asp Thr Leu Gln Tyr Phe Ala Ser Asn Gly Val Gln
    1430                1435                1440 ata aaa gat agt tat gcg aag gat agt aaa ggc aat aaa tat tat      4374
Ile Lys Asp Ser Tyr Ala Lys Asp Ser Lys Gly Asn Lys Tyr Tyr
    1445                1450                1455 ttt gac tca gct aca gga aat aac gat act ggg aaa gcc caa act      4419
Phe Asp Ser Ala Thr Gly Asn Asn Asp Thr Gly Lys Ala Gln Thr
    1460                1465                1470 tgg gat ggt aat ggc tac tat att act att gat tct gat gcg aac      4464
Trp Asp Gly Asn Gly Tyr Tyr Ile Thr Ile Asp Ser Asp Ala Asn
    1475                1480                1485 aat aca att ggg gtt aac aca gac tac act gcc tac atc act agc      4509
Asn Thr Ile Gly Val Asn Thr Asp Tyr Thr Ala Tyr Ile Thr Ser
```

-continued

|  |  |  |  |  |
|---|---|---|---|---|
| 1490 | 1495 | 1500 | | |
| tcg ctg cgc gaa gat ggc tta ttt gct aac gca cct tac ggt gtt | | | | 4554 |
| Ser Leu Arg Glu Asp Gly Leu Phe Ala Asn Ala Pro Tyr Gly Val | | | | |
| 1505 | 1510 | 1515 | | |
| gta aca aaa gac caa aat ggt aac gat ctt aag tgg cag tat att | | | | 4599 |
| Val Thr Lys Asp Gln Asn Gly Asn Asp Leu Lys Trp Gln Tyr Ile | | | | |
| 1520 | 1525 | 1530 | | |
| aac cat acg aaa cag tac gaa ggg caa caa gtg caa gtc acg cgt | | | | 4644 |
| Asn His Thr Lys Gln Tyr Glu Gly Gln Gln Val Gln Val Thr Arg | | | | |
| 1535 | 1540 | 1545 | | |
| caa tac aca gac agt aag gga gtc agc tgg aac tta att acc ttt | | | | 4689 |
| Gln Tyr Thr Asp Ser Lys Gly Val Ser Trp Asn Leu Ile Thr Phe | | | | |
| 1550 | 1555 | 1560 | | |
| gct ggt ggt gat tta caa gga caa agg ctt tgg gtg gat agt cgt | | | | 4734 |
| Ala Gly Gly Asp Leu Gln Gly Gln Arg Leu Trp Val Asp Ser Arg | | | | |
| 1565 | 1570 | 1575 | | |
| gcg tta act atg aca cca ttt aaa acg atg aac caa ata agc ttc | | | | 4779 |
| Ala Leu Thr Met Thr Pro Phe Lys Thr Met Asn Gln Ile Ser Phe | | | | |
| 1580 | 1585 | 1590 | | |
| att agt tat gct aac cgc aat gat ggg ttg ttt ttg aat gcg cca | | | | 4824 |
| Ile Ser Tyr Ala Asn Arg Asn Asp Gly Leu Phe Leu Asn Ala Pro | | | | |
| 1595 | 1600 | 1605 | | |
| tac caa gtc aag ggg tat caa tta gct ggg atg tcc aac caa tac | | | | 4869 |
| Tyr Gln Val Lys Gly Tyr Gln Leu Ala Gly Met Ser Asn Gln Tyr | | | | |
| 1610 | 1615 | 1620 | | |
| aag ggc caa caa gtg acc att gct ggg gtg gcg aac gtt tct gga | | | | 4914 |
| Lys Gly Gln Gln Val Thr Ile Ala Gly Val Ala Asn Val Ser Gly | | | | |
| 1625 | 1630 | 1635 | | |
| aaa gac tgg agt ctg att agt ttt aat ggg aca cag tac tgg att | | | | 4959 |
| Lys Asp Trp Ser Leu Ile Ser Phe Asn Gly Thr Gln Tyr Trp Ile | | | | |
| 1640 | 1645 | 1650 | | |
| gat agt cag gca ttg aat acc aat ttc aca cat gac atg aac caa | | | | 5004 |
| Asp Ser Gln Ala Leu Asn Thr Asn Phe Thr His Asp Met Asn Gln | | | | |
| 1655 | 1660 | 1665 | | |
| aag gtc ttt gtc aat aca act agt aat ctt gat ggg tta ttc tta | | | | 5049 |
| Lys Val Phe Val Asn Thr Thr Ser Asn Leu Asp Gly Leu Phe Leu | | | | |
| 1670 | 1675 | 1680 | | |
| aat gcg cca tac cgt caa ccg ggt tat aag tta gcc ggt ttg gct | | | | 5094 |
| Asn Ala Pro Tyr Arg Gln Pro Gly Tyr Lys Leu Ala Gly Leu Ala | | | | |
| 1685 | 1690 | 1695 | | |
| aaa aat tac aac aac caa acg gtt act gtt agt caa cag tac ttt | | | | 5139 |
| Lys Asn Tyr Asn Asn Gln Thr Val Thr Val Ser Gln Gln Tyr Phe | | | | |
| 1700 | 1705 | 1710 | | |
| gat gat caa ggc acg gtc tgg agt cag gtt gtc ctt ggg ggt cag | | | | 5184 |
| Asp Asp Gln Gly Thr Val Trp Ser Gln Val Val Leu Gly Gly Gln | | | | |
| 1715 | 1720 | 1725 | | |
| acg gtc tgg gtt gat aac cat gca ttg gca cag atg caa gtt agt | | | | 5229 |
| Thr Val Trp Val Asp Asn His Ala Leu Ala Gln Met Gln Val Ser | | | | |
| 1730 | 1735 | 1740 | | |
| gat aca gac caa cag ctc tat gtg aat agc aat ggt cgg aat gat | | | | 5274 |
| Asp Thr Asp Gln Gln Leu Tyr Val Asn Ser Asn Gly Arg Asn Asp | | | | |
| 1745 | 1750 | 1755 | | |
| ggg tta ttc ttg aat gcg cca tat cgt ggt caa ggg tca caa ctg | | | | 5319 |
| Gly Leu Phe Leu Asn Ala Pro Tyr Arg Gly Gln Gly Ser Gln Leu | | | | |
| 1760 | 1765 | 1770 | | |
| ata ggc atg acg gca gat tat aat ggg caa cat gta caa gtg acc | | | | 5364 |
| Ile Gly Met Thr Ala Asp Tyr Asn Gly Gln His Val Gln Val Thr | | | | |
| 1775 | 1780 | 1785 | | |
| aag caa ggg caa gat gcc tat ggt gca caa tgg cgt ctt att acg | | | | 5409 |
| Lys Gln Gly Gln Asp Ala Tyr Gly Ala Gln Trp Arg Leu Ile Thr | | | | |

| | | | | | | | | | | | | |
|---|---|---|---|---|---|---|---|---|---|---|---|---|
| Lys | Gln | Gly | Gln | Asp | Ala | Tyr | Gly | Ala | Gln | Trp | Arg | Leu Ile Thr |
| | 1790 | | | | 1795 | | | | 1800 | | | |

```
cta aat aat caa cag gtc tgg gtt gat agt cgc gct ttg agc aca    5454
Leu Asn Asn Gln Gln Val Trp Val Asp Ser Arg Ala Leu Ser Thr
    1805                1810                1815 aca atc atg caa gcc atg aat gat aat atg tat gta aat agc agc    5499
Thr Ile Met Gln Ala Met Asn Asp Asn Met Tyr Val Asn Ser Ser
1820                1825                1830 caa cgg aca gat ggc ttg tgg tta aac gca cct tat acg atg agt    5544
Gln Arg Thr Asp Gly Leu Trp Leu Asn Ala Pro Tyr Thr Met Ser
    1835                1840                1845 ggg gct aaa tgg gct ggt gat aca cgt tca gct aat ggg cgc tat    5589
Gly Ala Lys Trp Ala Gly Asp Thr Arg Ser Ala Asn Gly Arg Tyr
1850                1855                1860 gtc cat att tca aaa gct tat tca aac gaa gtc ggc aat aca tat    5634
Val His Ile Ser Lys Ala Tyr Ser Asn Glu Val Gly Asn Thr Tyr
    1865                1870                1875 tac ttg acg aat ttg aat ggt caa agc aca tgg att gac aag cgg    5679
Tyr Leu Thr Asn Leu Asn Gly Gln Ser Thr Trp Ile Asp Lys Arg
1880                1885                1890 gcg ttt act gtg acc ttc gat cag gtg gtg gca tta aat gca acg    5724
Ala Phe Thr Val Thr Phe Asp Gln Val Val Ala Leu Asn Ala Thr
    1895                1900                1905 att gtg gca cgc caa cga cca gat ggg atg ttt aag aca gca cca    5769
Ile Val Ala Arg Gln Arg Pro Asp Gly Met Phe Lys Thr Ala Pro
1910                1915                1920 tat ggt gaa gcg ggg gcg cag ttt gtc gat tat gtg aca aac tat    5814
Tyr Gly Glu Ala Gly Ala Gln Phe Val Asp Tyr Val Thr Asn Tyr
    1925                1930                1935 aac cag caa acc gtg cca gta aca aag caa cat tca gat gct cag    5859
Asn Gln Gln Thr Val Pro Val Thr Lys Gln His Ser Asp Ala Gln
1940                1945                1950 ggg aat caa tgg tac tta gcg aca gtg aat ggg aca caa tac tgg    5904
Gly Asn Gln Trp Tyr Leu Ala Thr Val Asn Gly Thr Gln Tyr Trp
    1955                1960                1965 att gat caa cgg tca ttt tca cca gta gta acg aag gtg gtt gat    5949
Ile Asp Gln Arg Ser Phe Ser Pro Val Val Thr Lys Val Val Asp
1970                1975                1980 tat caa gct aag att gtg cca cgg aca aca cgt gat ggt gtg ttt    5994
Tyr Gln Ala Lys Ile Val Pro Arg Thr Thr Arg Asp Gly Val Phe
    1985                1990                1995 agt ggc gca ccc tat ggg gaa gtg aat gct aag cta gtt aac atg    6039
Ser Gly Ala Pro Tyr Gly Glu Val Asn Ala Lys Leu Val Asn Met
2000                2005                2010 gca act gcg tat caa aat caa gtt gtc cat gcg aca ggg gaa tat    6084
Ala Thr Ala Tyr Gln Asn Gln Val Val His Ala Thr Gly Glu Tyr
    2015                2020                2025 acg aat gct tca ggg atc aca tgg agt cag ttc gcg tta agc ggg    6129
Thr Asn Ala Ser Gly Ile Thr Trp Ser Gln Phe Ala Leu Ser Gly
2030                2035                2040 caa gaa gac aag cta tgg att gat aag cgt gct ttg caa gct taa    6174
Gln Glu Asp Lys Leu Trp Ile Asp Lys Arg Ala Leu Gln Ala
    2045                2050                2055
```

<210> SEQ ID NO 2
<211> LENGTH: 2057
<212> TYPE: PRT
<213> ORGANISM: Leuconostoc mesenteroides

<400> SEQUENCE: 2

```
Met Lys Gln Gln Glu Thr Val Thr Arg Lys Lys Leu Tyr Lys Ser Gly
1               5                   10                  15

Lys Val Trp Val Ala Ala Thr Ala Phe Ala Val Leu Gly Val Ser
            20                  25                  30

Thr Val Thr Thr Val His Ala Asp Thr Asn Ser Asn Val Ala Val Lys
        35                  40                  45

Gln Ile Asn Asn Thr Gly Thr Asn Asp Ser Gly Glu Lys Lys Val Pro
    50                  55                  60

Val Pro Ser Thr Asn Asn Asp Ser Leu Lys Gln Gly Thr Asp Gly Phe
65                  70                  75                  80

Trp Tyr Asp Ser Asp Gly Asn Arg Val Asp Gln Lys Thr Asn Gln Ile
                85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Asp Glu Asn Ile Ser Lys
        115                 120                 125

Gln Thr Lys Ile Ala Asn Gln Gln Thr Val Asp Thr Ala Lys Gly Leu
    130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
    210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
        275                 280                 285

Lys Arg Ile Tyr Phe Ala Pro Asn Thr Gly Asn Ala Val Ala Asn Thr
    290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365

Thr Phe Asn Asn Gln Phe Met Tyr Phe Asp Ala Asp Thr Gly Ala Gly
    370                 375                 380

Lys Thr Ala Ile Glu Tyr Gln Phe Asp Gln Gly Leu Val Ser Gln Ser
385                 390                 395                 400

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
```

-continued

```
                420             425             430
Thr Asp Ile Leu Lys Asn Gly Asp Thr Trp Thr Ala Ser Thr Glu Thr
                435             440             445
Asp Met Arg Pro Leu Leu Met Thr Trp Trp Pro Asp Lys Gln Thr Gln
450             455             460
Ala Asn Tyr Leu Asn Phe Met Ser Ser Lys Gly Leu Gly Ile Thr Thr
465             470             475             480
Thr Tyr Thr Ala Ala Thr Ser Gln Lys Thr Leu Asn Asp Ala Ala Phe
                485             490             495
Val Ile Gln Thr Ala Ile Glu Gln Gln Ile Ser Leu Lys Lys Ser Thr
                500             505             510
Glu Trp Leu Arg Asp Ala Ile Asp Ser Phe Val Lys Thr Gln Ala Asn
                515             520             525
Trp Asn Lys Gln Thr Glu Asp Glu Ala Phe Asp Gly Leu Gln Trp Leu
                530             535             540
Gln Gly Gly Phe Leu Ala Tyr Gln Asp Asp Ser His Arg Thr Pro Asn
545             550             555             560
Thr Asp Ser Gly Asn Asn Arg Lys Leu Gly Arg Gln Pro Ile Asn Ile
                565             570             575
Asp Gly Ser Lys Asp Thr Thr Asp Gly Lys Gly Ser Glu Phe Leu Leu
                580             585             590
Ala Asn Asp Ile Asp Asn Ser Asn Pro Ile Val Gln Ala Glu Gln Leu
                595             600             605
Asn Trp Leu His Tyr Leu Met Asn Phe Gly Ser Ile Thr Gly Asn Asn
                610             615             620
Asp Asn Ala Asn Phe Asp Gly Ile Arg Val Asp Ala Val Asp Asn Val
625             630             635             640
Asp Ala Asp Leu Leu Lys Ile Ala Gly Asp Tyr Phe Lys Ala Leu Tyr
                645             650             655
Gly Thr Asp Lys Ser Asp Ala Asn Ala Asn Lys His Leu Ser Ile Leu
                660             665             670
Glu Asp Trp Asn Gly Lys Asp Pro Gln Tyr Val Asn Gln Gln Gly Asn
                675             680             685
Ala Gln Leu Thr Met Asp Tyr Thr Val Thr Ser Gln Phe Gly Asn Ser
                690             695             700
Leu Thr His Gly Ala Asn Asn Arg Ser Asn Met Trp Tyr Phe Leu Asp
705             710             715             720
Thr Gly Tyr Tyr Leu Asn Gly Asp Leu Asn Lys Lys Ile Val Asp Lys
                725             730             735
Asn Arg Pro Asn Ser Gly Thr Leu Val Asn Arg Ile Ala Asn Ser Gly
                740             745             750
Asp Thr Lys Val Ile Pro Asn Tyr Ser Phe Val Arg Ala His Asp Tyr
                755             760             765
Asp Ala Gln Asp Pro Ile Arg Lys Ala Met Ile Asp His Gly Ile Ile
                770             775             780
Lys Asn Met Gln Asp Thr Phe Thr Phe Asp Gln Leu Ala Gln Gly Met
785             790             795             800
Glu Phe Tyr Tyr Lys Asp Gln Glu Asn Pro Ser Gly Phe Lys Lys Tyr
                805             810             815
Asn Asp Tyr Asn Leu Pro Ser Ala Tyr Ala Met Leu Leu Thr Asn Lys
                820             825             830
Asp Thr Val Pro Arg Val Tyr Tyr Gly Asp Met Tyr Leu Glu Gly Gly
                835             840             845
```

-continued

Gln Tyr Met Glu Lys Gly Thr Ile Tyr Asn Pro Val Ile Ser Ala Leu
    850                 855                 860

Leu Lys Ala Arg Ile Lys Tyr Val Ser Gly Gln Thr Met Ala Thr
865                 870                 875                 880

Asp Ser Ser Gly Lys Asp Leu Lys Asp Gly Glu Thr Asp Leu Leu Thr
                    885                 890                 895

Ser Val Arg Phe Gly Lys Gly Ile Met Thr Ser Asp Gln Thr Thr Thr
                900                 905                 910

Gln Asp Asn Ser Gln Asp Tyr Lys Asn Gln Gly Ile Gly Val Ile Val
                915                 920                 925

Gly Asn Asn Pro Asp Leu Lys Leu Asn Asn Asp Lys Thr Ile Thr Leu
930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Asp Lys Ala Pro
                965                 970                 975

Thr Leu Arg Thr Asn Asp Asn Gly Asp Leu Ile Phe His Lys Thr Asn
                980                 985                 990

Thr Phe Val Lys Gln Asp Gly Thr Ile Ile Asn Tyr Glu Met Lys Gly
            995                 1000                1005

Ser Leu Asn Ala Leu Ile Ser Gly Tyr Leu Gly Val Trp Val Pro
    1010                1015                1020

Val Gly Ala Ser Asp Ser Gln Asp Ala Arg Thr Val Ala Thr Glu
    1025                1030                1035

Ser Ser Ser Ser Asn Asp Gly Ser Val Phe His Ser Asn Ala Ala
    1040                1045                1050

Leu Asp Ser Asn Val Ile Tyr Glu Gly Phe Ser Asn Phe Gln Ala
    1055                1060                1065

Met Pro Thr Ser Pro Glu Gln Ser Thr Asn Val Val Ile Ala Thr
    1070                1075                1080

Lys Ala Asn Leu Phe Lys Glu Leu Gly Ile Thr Ser Phe Glu Leu
    1085                1090                1095

Ala Pro Gln Tyr Arg Ser Ser Gly Asp Thr Asn Tyr Gly Gly Met
    1100                1105                1110

Ser Phe Leu Asp Ser Phe Leu Asn Asn Gly Tyr Ala Phe Thr Asp
    1115                1120                1125

Arg Tyr Asp Leu Gly Phe Asn Lys Ala Asp Gly Asn Pro Asn Pro
    1130                1135                1140

Thr Lys Tyr Gly Thr Asp Gln Asp Leu Arg Asn Ala Ile Glu Ala
    1145                1150                1155

Leu His Lys Asn Gly Met Gln Ala Ile Ala Asp Trp Val Pro Asp
    1160                1165                1170

Gln Ile Tyr Ala Leu Pro Gly Lys Glu Val Val Thr Ala Thr Arg
    1175                1180                1185

Val Asp Glu Arg Gly Asn Gln Leu Lys Asp Thr Asp Phe Val Asn
    1190                1195                1200

Leu Leu Tyr Val Ala Asn Thr Lys Ser Ser Gly Val Asp Tyr Gln
    1205                1210                1215

Ala Lys Tyr Gly Gly Glu Phe Leu Asp Lys Leu Arg Glu Glu Tyr
    1220                1225                1230

Pro Ser Leu Phe Lys Gln Asn Gln Val Ser Thr Gly Gln Pro Ile
    1235                1240                1245

-continued

```
Asp Ala Ser Thr Lys Ile Lys Gln Trp Ser Ala Lys Tyr Met Asn
    1250                1255                1260
Gly Thr Asn Ile Leu His Arg Gly Ala Tyr Tyr Val Leu Lys Asp
    1265                1270                1275
Trp Ala Thr Asn Gln Tyr Phe Asn Ile Ala Lys Thr Asn Glu Val
    1280                1285                1290
Phe Leu Pro Leu Gln Leu Gln Asn Lys Asp Ala Gln Thr Gly Phe
    1295                1300                1305
Ile Ser Asp Ala Ser Gly Val Lys Tyr Tyr Ser Ile Ser Gly Tyr
    1310                1315                1320
Gln Ala Lys Asp Thr Phe Ile Glu Asp Gly Asn Gly Asn Trp Tyr
    1325                1330                1335
Tyr Phe Asp Lys Asp Gly Tyr Met Val Arg Ser Gln Gln Gly Glu
    1340                1345                1350
Asn Pro Ile Arg Thr Val Glu Thr Ser Val Asn Thr Arg Asn Gly
    1355                1360                1365
Asn Tyr Tyr Phe Met Pro Asn Gly Val Glu Leu Arg Lys Gly Phe
    1370                1375                1380
Gly Thr Asp Asn Ser Gly Asn Val Tyr Tyr Phe Asp Asp Gln Gly
    1385                1390                1395
Lys Met Val Arg Asp Lys Tyr Ile Asn Asp Asp Ala Asn Asn Phe
    1400                1405                1410
Tyr His Leu Asn Val Asp Gly Thr Met Ser Arg Gly Leu Phe Lys
    1415                1420                1425
Phe Asp Ser Asp Thr Leu Gln Tyr Phe Ala Ser Asn Gly Val Gln
    1430                1435                1440
Ile Lys Asp Ser Tyr Ala Lys Asp Ser Lys Gly Asn Lys Tyr Tyr
    1445                1450                1455
Phe Asp Ser Ala Thr Gly Asn Asn Asp Thr Gly Lys Ala Gln Thr
    1460                1465                1470
Trp Asp Gly Asn Gly Tyr Tyr Ile Thr Ile Asp Ser Asp Ala Asn
    1475                1480                1485
Asn Thr Ile Gly Val Asn Thr Asp Tyr Thr Ala Tyr Ile Thr Ser
    1490                1495                1500
Ser Leu Arg Glu Asp Gly Leu Phe Ala Asn Ala Pro Tyr Gly Val
    1505                1510                1515
Val Thr Lys Asp Gln Asn Gly Asn Asp Leu Lys Trp Gln Tyr Ile
    1520                1525                1530
Asn His Thr Lys Gln Tyr Glu Gly Gln Gln Val Gln Val Thr Arg
    1535                1540                1545
Gln Tyr Thr Asp Ser Lys Gly Val Ser Trp Asn Leu Ile Thr Phe
    1550                1555                1560
Ala Gly Gly Asp Leu Gln Gly Gln Arg Leu Trp Val Asp Ser Arg
    1565                1570                1575
Ala Leu Thr Met Thr Pro Phe Lys Thr Met Asn Gln Ile Ser Phe
    1580                1585                1590
Ile Ser Tyr Ala Asn Arg Asn Asp Gly Leu Phe Leu Asn Ala Pro
    1595                1600                1605
Tyr Gln Val Lys Gly Tyr Gln Leu Ala Gly Met Ser Asn Gln Tyr
    1610                1615                1620
Lys Gly Gln Gln Val Thr Ile Ala Gly Val Ala Asn Val Ser Gly
    1625                1630                1635
Lys Asp Trp Ser Leu Ile Ser Phe Asn Gly Thr Gln Tyr Trp Ile
```

-continued

```
            1640                1645                1650
Asp Ser Gln Ala Leu Asn Thr Asn Phe Thr His Asp Met Asn Gln
    1655                1660                1665

Lys Val Phe Val Asn Thr Thr Ser Asn Leu Asp Gly Leu Phe Leu
    1670                1675                1680

Asn Ala Pro Tyr Arg Gln Pro Gly Tyr Lys Leu Ala Gly Leu Ala
    1685                1690                1695

Lys Asn Tyr Asn Asn Gln Thr Val Thr Val Ser Gln Gln Tyr Phe
    1700                1705                1710

Asp Asp Gln Gly Thr Val Trp Ser Gln Val Val Leu Gly Gly Gln
    1715                1720                1725

Thr Val Trp Val Asp Asn His Ala Leu Ala Gln Met Gln Val Ser
    1730                1735                1740

Asp Thr Asp Gln Gln Leu Tyr Val Asn Ser Asn Gly Arg Asn Asp
    1745                1750                1755

Gly Leu Phe Leu Asn Ala Pro Tyr Arg Gly Gln Gly Ser Gln Leu
    1760                1765                1770

Ile Gly Met Thr Ala Asp Tyr Asn Gly Gln His Val Gln Val Thr
    1775                1780                1785

Lys Gln Gly Gln Asp Ala Tyr Gly Ala Gln Trp Arg Leu Ile Thr
    1790                1795                1800

Leu Asn Asn Gln Gln Val Trp Val Asp Ser Arg Ala Leu Ser Thr
    1805                1810                1815

Thr Ile Met Gln Ala Met Asn Asp Asn Met Tyr Val Asn Ser Ser
    1820                1825                1830

Gln Arg Thr Asp Gly Leu Trp Leu Asn Ala Pro Tyr Thr Met Ser
    1835                1840                1845

Gly Ala Lys Trp Ala Gly Asp Thr Arg Ser Ala Asn Gly Arg Tyr
    1850                1855                1860

Val His Ile Ser Lys Ala Tyr Ser Asn Glu Val Gly Asn Thr Tyr
    1865                1870                1875

Tyr Leu Thr Asn Leu Asn Gly Gln Ser Thr Trp Ile Asp Lys Arg
    1880                1885                1890

Ala Phe Thr Val Thr Phe Asp Gln Val Val Ala Leu Asn Ala Thr
    1895                1900                1905

Ile Val Ala Arg Gln Arg Pro Asp Gly Met Phe Lys Thr Ala Pro
    1910                1915                1920

Tyr Gly Glu Ala Gly Ala Gln Phe Val Asp Tyr Val Thr Asn Tyr
    1925                1930                1935

Asn Gln Gln Thr Val Pro Val Thr Lys Gln His Ser Asp Ala Gln
    1940                1945                1950

Gly Asn Gln Trp Tyr Leu Ala Thr Val Asn Gly Thr Gln Tyr Trp
    1955                1960                1965

Ile Asp Gln Arg Ser Phe Ser Pro Val Thr Lys Val Val Asp
    1970                1975                1980

Tyr Gln Ala Lys Ile Val Pro Arg Thr Thr Arg Asp Gly Val Phe
    1985                1990                1995

Ser Gly Ala Pro Tyr Gly Glu Val Asn Ala Lys Leu Val Asn Met
    2000                2005                2010

Ala Thr Ala Tyr Gln Asn Gln Val Val His Ala Thr Gly Glu Tyr
    2015                2020                2025

Thr Asn Ala Ser Gly Ile Thr Trp Ser Gln Phe Ala Leu Ser Gly
    2030                2035                2040
```

| Gln | Glu | Asp | Lys | Leu | Trp | Ile | Asp | Lys | Arg | Ala | Leu | Gln | Ala |
| --- | --- | --- | --- | --- | --- | --- | --- | --- | --- | --- | --- | --- | --- |
| 2045 | | | | 2050 | | | | | 2055 | | | | |

<210> SEQ ID NO 3
<211> LENGTH: 6174
<212> TYPE: DNA
<213> ORGANISM: Artificial
<220> FEATURE:
<223> OTHER INFORMATION: synthethic sequence encoding a protein with the activity of alternansucrase

<400> SEQUENCE: 3

```
atgaaacaac aagaaacagt tacccgtaaa aaactttata aatccggtaa ggtttgggtt      60
gcagcagcta ctgcatttgc ggtattgggg gtttcaactg taacaacagt ccatgcggac     120
accaactcca acgtggccgt gaagcagatc aacaacaccg gcaccaacga ctccggcgag     180
aagaaggtgc cagtgccatc caccaacaac gactccctca gcagggcac cgacggcttc     240
tggtacgact ccgacggcaa ccgcgtggac cagaagacca ccagatcct cctcaccgcc     300
gagcagctca agaagaacaa cgagaagaac ctctccgtga tctccgacga cacctccaag     360
aaggacgacg agaacatctc caagcagacc aagatcgcca accagcagac cgtggacacc     420
gccaagggcc tcaccacctc caacctctcc gaccccatca ccggtggcca ctacgagaac     480
cacaacggct acttcgtgta catcgacgcc tccggcaagc aggtgaccgg cctccagaac     540
atcgacggca acctccagta cttcgacgac aacggctacc aggtgaaggg ctccttccgc     600
gacgtgaacg gcaagcacat ctacttcgac tccgtgaccg gcaaggcctc ctccaacgtg     660
gacatcgtga acggcaaggc ccagggctac gacgcccagg gcaaccagct caagaagtcc     720
tacgtggccg actcctccgg ccagacctac tacttcgacg gcaacggcca gccactcatc     780
ggcctccaga ccatcgacgg caacctccag tacttcaacc agcagggcgt gcagatcaag     840
ggtggcttcc aggacgtgaa caacaagcgc atctacttcg ctcccaacac cggcaacgcc     900
gtggccaaca ccgagatcat caacggcaag ctccagggca gggacgccaa cggcaaccag     960
gtgaagaacg ccttctccaa ggacgtggct ggcaacacct tctacttcga cgccaacggc    1020
gtgatgctca ccggcctcca gaccatctcc ggcaagacct actacctcga cgagcagggc    1080
cacctccgca gaactacgc cggcaccttc aacaaccagt tcatgtactt cgacgccgac    1140
actggcgctg gcaagaccgc catcgagtac cagttcgacc agggcctcgt gtcccagtcc    1200
aacgagaaca ccccacacaa cgctgccaag tcctacgaca gtcctccctt cgagaacgtg    1260
gacggctacc tcaccgccga cacctggtac cgcccaaccg acatcctcaa gaacggcgac    1320
acctggaccg cctccaccga gaccgacatg aggccactcc tcatgacctg gtggccagac    1380
aagcagaccc aggccaacta cctcaacttc atgtcctcca agggcctcgg catcaccacc    1440
acctacaccg ctgccaccctc ccagaagacc ctcaacgacg ctgccttcgt gatccagacc    1500
gccatcgagc agcagatctc cctcaagaag tccaccgagt ggctccgcga cgccatcgac    1560
tccttcgtga agacccaggc caactggaac aagcagaccg aggacgaggc cttcgacggc    1620
ctccagtggc tccagggtgg cttcctcgcc taccaggacg actcccaccg caccccctaac    1680
accgactccg gcaacaaccg caagctcggc aggcagccca tcaacatcga cggctccaag    1740
gacaccaccg acggcaaggg ctccgagttc ctcctcgcca cgacatcga caactccaac    1800
ccgatcgtgc aggccgagca gctcaactgg ctccactacc tcatgaactt cggctccatc    1860
accggcaaca cgacaacgc caacttcgac ggcatccgcg tggacgccgt ggacaacgtg    1920
```

```
gacgccgacc tcctcaagat cgctggcgac tacttcaagg ccctctacgg caccgacaag   1980
tccgacgcca acgccaacaa gcacctctcc atcctcgagg actggaacgg caaggaccca   2040
cagtacgtga accagcaggg caacgcccag ctcactatgg actacaccgt gacctcccag   2100
ttcggcaact ccctcaccca cggcgccaac aaccgctcca acatgtggta cttcctcgac   2160
accggctact acctcaacgg cgacctcaac aagaagatcg tggacaagaa caggcctaac   2220
tccggcaccc tcgtgaaccg catcgccaac tccggcgaca ccaaggtgat ccccaactac   2280
tccttcgtga gggcccacga ctacgacgcc caggacccga tccgcaaggc catgatcgac   2340
cacggcatca tcaagaacat gcaggacacc ttcaccttcg accagctcgc ccagggcatg   2400
gagttctact acaaggacca ggagaacccg tccggcttca agaagtacaa cgactacaac   2460
ctcccatccg cctacgccat gctcctcacc aacaaggaca ccgtgcccag ggtgtactac   2520
ggcgacatgt acctcgaggg tggccagtac atggagaagg gcaccatcta caacccggtg   2580
atctccgccc tcctcaaggc ccgcatcaag tacgtgtccg gtggccagac tatggccacc   2640
gactcctccg gcaaggacct caaggacggc gagaccgacc tcctcacctc cgtgcgcttc   2700
ggcaagggca tcatgacctc cgaccagacc accacccagg acaactccca ggactacaag   2760
aaccagggca tcggcgtgat cgtgggcaac aacccagacc tcaagctcaa caacgacaag   2820
accatcaccc tccacatggg caaggcccac aagaaccagc tctacagggc cctcgtgctc   2880
tccaacgact ccggcatcga cgtgtacgac tccgacgaca aggccccgac cctccgcacc   2940
aacgacaacg gcgacctcat cttccacaag accaacacct tcgtgaagca ggacggcacc   3000
atcatcaact acgagatgaa gggctccctc aacgccctca tctccggcta cctcggcgtg   3060
tgggtgccag tgggcgcctc cgactcccag gacgcccgca ccgtggccac cgagtcctcc   3120
tcctccaacg acggctccgt gttccactcc aacgctgccc tcgactccaa cgtgatctac   3180
gagggcttct ccaacttcca ggccatgccc acctcccgg agcagtccac caacgtggtg   3240
atcgccacca aggccaacct cttcaaggag ctgggcatca cctccttcga gctgccccca   3300
cagtaccgct cctccggcga caccaactac ggtggcatgt ccttcctcga ctccttcctc   3360
aacaacggct acgccttcac cgaccgctac gacctcggct tcaacaaggc cgacggcaac   3420
ccgaacccaa ctaagtacgg caccgaccag gacctccgca acgccatcga ggccctccac   3480
aagaacggca tgcaggccat cgccgactgg gtgccggacc agatctacgc cctcccaggc   3540
aaggaggtgg tgaccgccac ccgcgtggac gagcgcggca accagctcaa ggacaccgac   3600
ttcgtgaacc tcctctacgt ggccaacacc aagtcctccg cgtggactac caggccaag   3660 tacggtggcg agttcctcga caagctccgc gaggagtacc catccctctt caagcagaac   3720
caggtgtcca ccgccagcc tatcgacgcc tccaccaaga tcaagcagtg gtccgccaag   3780
tacatgaacg gcaccaacat cctccacagg ggtgcctact acgtgctcaa ggactgggcc   3840
accaaccagt acttcaacat cgccaagacc aacgaggtgt cctcccact ccagctccag   3900 aacaaggacg cccagaccgg cttcatctcc gacgcctccg gcgtgaagta ctactccatc   3960
tccggctacc aggccaagga caccttcatc gaggacggca acggcaactg gactacttc   4020 gacaaggacg gctacatggt gcgctcccag caggcgaga acccgatccg caccgtggag   4080
acctccgtga cacccgcaa cggcaactac tacttcatgc ctaacggcgt ggagctccgc   4140
aagggcttcg gcaccgacaa ctccggcaac gtgtactact tcgacgacca gggcaagatg   4200
gtgcgcgaca agtacatcaa cgacgacgcc aacaacttct accacctcaa cgtggacggc   4260
accatgtcca ggggcctctt caagttcgac tccgacaccc tccagtactt cgcctccaac   4320
```

```
ggcgtgcaga tcaaggactc ctacgccaag gactccaagg caacaagta ctacttcgac      4380 tccgccaccg gcaacaacga caccggcaag gcccagacct gggacggcaa cggctactac      4440
atcaccatcg actccgacgc caacaacacc atcggcgtga acaccgacta caccgcctac      4500
atcacctcct ccctccgcga ggacggcctc ttcgccaacg cccccctacgg cgtggtgacc     4560 aaggaccaga acggcaacga cctcaagtgg cagtacatca accacaccaa gcagtacgag      4620
ggccagcagg tgcaggtgac cgccagtac accgactcca agggcgtgtc ctggaacctc       4680
atcaccttcg ccggtggcga cctgcagggc cagcgcctct gggtggactc cagggccctc      4740
accatgaccc ccttcaagac catgaaccag atctccttca tctcctacgc caaccgcaac      4800
gacggcctct tcctcaacgc cccataccag gtgaagggct accagctcgc cggcatgtcc      4860
aaccagtaca agggccagca ggtgaccatc gctggcgtgg ccaacgtgtc cggcaaggac      4920
tggtccctca tctccttcaa cggcacccag tactggatcg actcccaggc cctcaacacc      4980
aacttcaccc acgacatgaa ccagaaggtg ttcgtgaaca ccacctccaa cctcgacggc      5040
ctcttcctca acgctcccta ccgccagccg ggctacaagc tcgctggcct cgccaagaac      5100
tacaacaacc agaccgtgac cgtgtcccag cagtacttcg acgaccaggg caccgtgtgg      5160
tcccaggtgg tgctcggtgg ccagaccgtg tgggtggaca ccacgccct cgcccagatg        5220 caggtgtccg acaccgacca gcagctctac gtgaactcca acggtcgcaa cgacggcctc      5280
ttcctcaacg ctccgtacag gggccagggc tcccagctca tcggcatgac cgccgactac      5340
aacggccagc acgtgcaggt gaccaagcag ggccaggacg cctacggtgc ccagtggcgc      5400
ctcatcaccc tcaacaacca gcaggtgtgg gtggactcca gggctctctc caccaccatc      5460
atgcaggcca tgaacgacaa catgtacgtg aactcctccc agcgcaccga cggcctctgg      5520
ctcaacgctc cctacaccat gtctggcgcc aagtgggctg gcgacacccg ctccgccaac      5580
ggcaggtacg tgcacatctc caaggcctac tccaacgagg tgggcaacac ctactacctc      5640
accaacctca acgccagtc cacctggatc gacaagcgcg ctttcaccgt gaccttcgac       5700
caggtggtgg ccctcaacgc caccatcgtg gccaggcaga ggccagacgg catgttcaag      5760
accgctccct acggcgaggc cggcgcccag ttcgtggact acgtgaccaa ctacaaccag      5820
cagaccgtgc cggtgaccaa gcagcactcc gacgcccagg gcaaccagtg gtacttggcc      5880
accgtgaacg gcacccagta ctggatcgac cagcgctcct tctccccggt ggtgaccaag      5940
gtggtggact accaggccaa gatcgtgcca aggaccaccc gcgacggcgt gttctccggt      6000
gccccgtacg gcgaggtgaa cgccaagctc gtgaacatgg ccaccgccta ccagaaccag      6060
gtggtgcacg ccaccggcga gtacaccaac gcctccggca tcacctggtc ccagttcgcc      6120
ctctccggcc aggaggacaa gctctggatc gacaagcgcg ctctccaagc ttga            6174
```

<210> SEQ ID NO 4
<211> LENGTH: 43
<212> TYPE: DNA
<213> ORGANISM: Artificial
<220> FEATURE:
<223> OTHER INFORMATION: Primer

<400> SEQUENCE: 4
gaaagcttgg ctgcaggtca gtcccttatg ttacgtcctg tag                        43

<210> SEQ ID NO 5
<211> LENGTH: 33
<212> TYPE: DNA

```
<213> ORGANISM: Artificial
<220> FEATURE:
<223> OTHER INFORMATION: Primer

<400> SEQUENCE: 5
ctggtcccgg gattcattgt ttgcctccct gct                                    33

<210> SEQ ID NO 6
<211> LENGTH: 28
<212> TYPE: DNA
<213> ORGANISM: Artificial
<220> FEATURE:
<223> OTHER INFORMATION: Primer

<400> SEQUENCE: 6
tcgagctcgc gaaagcttgg ctgcaggt                                          28

<210> SEQ ID NO 7
<211> LENGTH: 65
<212> TYPE: DNA
<213> ORGANISM: Artificial
<220> FEATURE:
<223> OTHER INFORMATION: synthethic linker sequence

<400> SEQUENCE: 7
aacaactctc ctggcgcacc atcgtcggct acagcctcgg gaattgctgc aggtcgacgg       60
atccg                                                                  65

<210> SEQ ID NO 8
<211> LENGTH: 69
<212> TYPE: DNA
<213> ORGANISM: Artificial
<220> FEATURE:
<223> OTHER INFORMATION: synthethic linker sequence

<400> SEQUENCE: 8
aattcggatc cgtcgacctg cagcaattcc cgaggctgta gccgacgatg gtgcgccagg       60
agagttgtt                                                              69

<210> SEQ ID NO 9
<211> LENGTH: 45
<212> TYPE: DNA
<213> ORGANISM: Artificial
<220> FEATURE:
<223> OTHER INFORMATION: Primer

<400> SEQUENCE: 9
cggatcggat ccgtcgacct gcagatcgtt caaacatttg gcaat                       45

<210> SEQ ID NO 10
<211> LENGTH: 37
<212> TYPE: DNA
<213> ORGANISM: Artificial
<220> FEATURE:
<223> OTHER INFORMATION: Primer

<400> SEQUENCE: 10
ccacggaatt cgatctagta acatagatga caccgcg                                37

<210> SEQ ID NO 11
<211> LENGTH: 18
<212> TYPE: DNA
<213> ORGANISM: Artificial
<220> FEATURE:
<223> OTHER INFORMATION: synthethic oligonucleotide
```

```
<400> SEQUENCE: 11
gcggccgcgg cagccatg                                                   18

<210> SEQ ID NO 12
<211> LENGTH: 18
<212> TYPE: DNA
<213> ORGANISM: Artificial
<220> FEATURE:
<223> OTHER INFORMATION: synthethic oligonucleotide

<400> SEQUENCE: 12
accggatatc gcggccgc                                                   18

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
agcttgaacc ggatatcgcg gccgc                                           25

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
agctgcggcc gcgatatccg gttca                                           25

<210> SEQ ID NO 15
<211> LENGTH: 53
<212> TYPE: DNA
<213> ORGANISM: Artificial
<220> FEATURE:
<223> OTHER INFORMATION: Primer

<400> SEQUENCE: 15
caactgagct ctgcagaatt cggcttgttc gggcagccat ggacaccaac tcc            53

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
gccggagttg tcggtgccga agcccttgcg                                      30

<210> SEQ ID NO 17
<211> LENGTH: 30
<212> TYPE: DNA
<213> ORGANISM: Artificial
<220> FEATURE:
<223> OTHER INFORMATION: Primer

<400> SEQUENCE: 17
tcctacgaca agtcctcctt cgagaacgtg                                      30

<210> SEQ ID NO 18
```

```
<211> LENGTH: 38
<212> TYPE: DNA
<213> ORGANISM: Artificial
<220> FEATURE:
<223> OTHER INFORMATION: Primer

<400> SEQUENCE: 18
cttacggatc cactagtaac ggccgcgata tccggttc                              38

<210> SEQ ID NO 19
<211> LENGTH: 27
<212> TYPE: DNA
<213> ORGANISM: Artificial
<220> FEATURE:
<223> OTHER INFORMATION: Primer

<400> SEQUENCE: 19
gccatcgagc agcagatctc cctcaag                                         27

<210> SEQ ID NO 20
<211> LENGTH: 28
<212> TYPE: DNA
<213> ORGANISM: Artificial
<220> FEATURE:
<223> OTHER INFORMATION: Primer

<400> SEQUENCE: 20
cataggatcc ctacacgccg gaggcgtc                                        28

<210> SEQ ID NO 21
<211> LENGTH: 40
<212> TYPE: DNA
<213> ORGANISM: Artificial
<220> FEATURE:
<223> OTHER INFORMATION: Primer

<400> SEQUENCE: 21
taatacgact cactataggc agaattcggc ttgttcgggc                           40

<210> SEQ ID NO 22
<211> LENGTH: 28
<212> TYPE: DNA
<213> ORGANISM: Artificial
<220> FEATURE:
<223> OTHER INFORMATION: Primer

<400> SEQUENCE: 22
agtaacggcc gcgatatccg gttcaagc                                        28

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
cgaagaggcc gtcctagcgg agggag                                          26

<210> SEQ ID NO 24
<211> LENGTH: 24
<212> TYPE: DNA
<213> ORGANISM: Artificial
<220> FEATURE:
<223> OTHER INFORMATION: Primer

<400> SEQUENCE: 24
```

```
ggtgccgaag ccctagcgga gctc                                          24

<210> SEQ ID NO 25
<211> LENGTH: 29
<212> TYPE: DNA
<213> ORGANISM: Artificial
<220> FEATURE:
<223> OTHER INFORMATION: Primer

<400> SEQUENCE: 25
ccggagatgg agtagtacta cacgccgga                                     29
```